US010912783B2

(12) United States Patent
Thorsteinsson et al.

(10) Patent No.: US 10,912,783 B2
(45) Date of Patent: *Feb. 9, 2021

(54) FORMULATIONS FOR SOLUBILIZING HORMONES

(71) Applicant: TherapeuticsMD, Inc., Boca Raton, FL (US)

(72) Inventors: Thorsteinn Thorsteinsson, Boynton Beach, FL (US); Frederick D. Sancilio, Palm Beach Gardens, FL (US); Brian A. Bernick, Boca Raton, FL (US); Julia M. Amadio, Boca Raton, FL (US)

(73) Assignee: THERAPEUTICSMD, INC., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/401,884

(22) Filed: May 2, 2019

(65) Prior Publication Data
US 2019/0321376 A1 Oct. 24, 2019

Related U.S. Application Data

(62) Division of application No. 15/217,301, filed on Jul. 22, 2016, now Pat. No. 10,328,087.

(60) Provisional application No. 62/196,021, filed on Jul. 23, 2015.

(51) Int. Cl.
| | |
|---|---|
| A61K 31/57 | (2006.01) |
| A61K 31/565 | (2006.01) |
| A61K 9/48 | (2006.01) |
| A61K 47/06 | (2006.01) |
| A61K 31/573 | (2006.01) |
| A61K 9/00 | (2006.01) |
| A61K 47/14 | (2017.01) |
| A61K 9/06 | (2006.01) |
| A61K 31/015 | (2006.01) |

(52) U.S. Cl.
CPC .......... A61K 31/573 (2013.01); A61K 9/0014 (2013.01); A61K 9/06 (2013.01); A61K 9/4825 (2013.01); A61K 9/4858 (2013.01); A61K 31/015 (2013.01); A61K 31/565 (2013.01); A61K 47/06 (2013.01); A61K 47/14 (2013.01)

(58) Field of Classification Search
CPC ...... A61K 31/56; A61K 31/57; A61K 31/573; A61K 31/565; A61K 9/4825; A61K 9/4858

See application file for complete search history.

(56) References Cited

U.S. PATENT DOCUMENTS

| | | |
|---|---|---|
| 1,967,351 A | 7/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Reinhardt et al. |
| 3,526,648 A | 9/1970 | Daniel et al. |
| 3,710,795 A | 1/1973 | Higuchi et al. |
| 3,729,560 A | 4/1973 | Hagerman |
| 3,729,566 A | 4/1973 | Youngdale et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | Van Der Vies |
| 4,093,709 A | 6/1978 | Choi et al. |
| 4,154,820 A | 5/1979 | Simoons |
| 4,155,991 A | 5/1979 | Hartmann et al. |
| 4,196,188 A | 4/1980 | Besins |
| 4,215,691 A | 8/1980 | Wong |
| 4,237,885 A | 12/1980 | Pharriss et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |

(Continued)

FOREIGN PATENT DOCUMENTS

| | | |
|---|---|---|
| BR | PI1001367 A2 | 7/2012 |
| CN | 102258455 A | 11/2011 |

(Continued)

OTHER PUBLICATIONS

US 6,214,374 B1, 04/2001, Schmirler et al. (withdrawn)

(Continued)

Primary Examiner — Irina Neagu
(74) Attorney, Agent, or Firm — Sterne, Kessler, Goldstein & Fox P.L.L.C.

(57) ABSTRACT

Compositions and methods for the solubilization of steroid hormones are disclosed.

6 Claims, 12 Drawing Sheets

(56) References Cited

U.S. PATENT DOCUMENTS

| | | |
|---|---|---|
| 4,449,980 A | 5/1984 | Millar et al. |
| 4,572,915 A | 2/1986 | Crooks |
| 4,610,687 A | 9/1986 | Fogwell |
| 4,629,449 A | 12/1986 | Wong |
| 4,719,239 A | 1/1988 | Muller et al. |
| 4,727,109 A | 2/1988 | Schmidt et al. |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,944,949 A | 7/1990 | Story et al. |
| 4,961,931 A | 10/1990 | Wong |
| 5,030,629 A | 7/1991 | Rajadhyaksha |
| 5,064,654 A | 11/1991 | Berner et al. |
| 5,071,643 A | 12/1991 | Yu et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,364,632 A | 11/1994 | Benita et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Hoffmann et al. |
| 5,543,150 A | 8/1996 | Bologna et al. |
| 5,547,948 A | 8/1996 | Barcomb |
| 5,556,635 A | 9/1996 | Istin et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Mikler et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Teillaud et al. |
| 5,607,691 A | 3/1997 | Hale et al. |
| 5,607,693 A | 3/1997 | Bonte et al. |
| 5,609,617 A | 3/1997 | Shealy et al. |
| 5,620,705 A | 4/1997 | Dong et al. |
| 5,626,866 A | 5/1997 | Ebert et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,645,856 A | 7/1997 | Lacy et al. |
| 5,653,983 A | 8/1997 | Meybeck et al. |
| 5,656,286 A | 8/1997 | Miranda et al. |
| 5,656,289 A | 8/1997 | Cho et al. |
| 5,660,839 A | 8/1997 | Allec et al. |
| 5,662,927 A | 9/1997 | Ehrlich et al. |
| 5,663,160 A | 9/1997 | Meybeck et al. |
| 5,676,968 A | 10/1997 | Lipp et al. |
| 5,677,292 A | 10/1997 | Li et al. |
| 5,686,097 A | 11/1997 | Taskovich et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Kanios et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Yewey et al. |
| 5,780,050 A | 7/1998 | Jain et al. |
| 5,785,976 A | 7/1998 | Westesen et al. |
| 5,788,980 A | 8/1998 | Nabahi |
| 5,788,984 A | 8/1998 | Guenther et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Hirano et al. |
| 5,827,200 A | 10/1998 | Caillouette |
| 5,840,327 A | 11/1998 | Gale et al. |
| 5,843,468 A | 12/1998 | Burkoth et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,882,676 A | 3/1999 | Lee et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,952,000 A | 9/1999 | Venkateshwaran et al. |
| 5,958,446 A | 9/1999 | Miranda et al. |
| 5,962,445 A | 10/1999 | Stewart |
| 5,968,919 A | 10/1999 | Samour et al. |
| 5,972,372 A | 10/1999 | Saleh et al. |
| 5,980,945 A | 11/1999 | Ruiz |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon-Lapillonne et al. |
| 6,010,715 A | 1/2000 | Wick et al. |
| 6,013,276 A | 1/2000 | Math et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Chwalisz et al. |
| 6,056,972 A | 5/2000 | Hermsmeyer |
| 6,060,077 A | 5/2000 | Meignant |
| 6,068,853 A | 5/2000 | Giannos et al. |
| 6,074,625 A | 6/2000 | Hawthorne et al. |
| 6,077,531 A | 6/2000 | Salin-Drouin |
| 6,080,118 A | 6/2000 | Blythe |

(56) References Cited

U.S. PATENT DOCUMENTS

| | | |
|---|---|---|
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Preuilh et al. |
| 6,107,276 A | 8/2000 | Carli et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Chiang et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | De et al. |
| 6,190,331 B1 | 2/2001 | Caillouette |
| 6,201,072 B1 | 3/2001 | Rathi et al. |
| 6,217,886 B1 | 4/2001 | Önyüksel et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Berger et al. |
| 6,245,811 B1 | 6/2001 | Horrobin et al. |
| 6,248,363 B1 | 6/2001 | Patel et al. |
| 6,262,115 B1 | 7/2001 | Guittard et al. |
| 6,264,980 B1 | 7/2001 | Hille |
| 6,267,984 B1 | 7/2001 | Beste et al. |
| 6,267,985 B1 | 7/2001 | Chen et al. |
| 6,274,165 B1 | 8/2001 | Meconi et al. |
| 6,277,418 B1 | 8/2001 | Markaverich et al. |
| 6,283,927 B1 | 9/2001 | Caillouette |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | De et al. |
| 6,309,663 B1 | 10/2001 | Patel et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Bowman et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,740 B1 | 7/2002 | Unger |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Dunlop et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Rossi-Montero et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Meconi et al. |
| 6,526,980 B1 | 3/2003 | Tracy et al. |
| 6,528,094 B1 | 3/2003 | Savoir et al. |
| 6,531,139 B1 | 3/2003 | Gao et al. |
| 6,531,149 B1 | 3/2003 | Kirstgen et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Stewart et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein et al. |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | De et al. |
| 6,599,519 B1 | 7/2003 | Seo et al. |
| 6,599,962 B2 | 7/2003 | McCleskey et al. |
| 6,610,652 B2 | 8/2003 | Heaton et al. |
| 6,610,670 B2 | 8/2003 | Backensfeld et al. |
| 6,610,674 B1 | 8/2003 | Schreiber |
| 6,623,761 B2 | 9/2003 | Hassan |
| 6,635,274 B1 | 10/2003 | Masiz et al. |
| 6,635,283 B2 | 10/2003 | Edwards et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,682,757 B1 | 1/2004 | Wright |
| 6,692,763 B1 | 2/2004 | Cummings et al. |
| 6,708,822 B1 | 3/2004 | Muni |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Huebner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Eini et al. |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |

(56) References Cited

U.S. PATENT DOCUMENTS

| | | |
|---|---|---|
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Daniels et al. |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Dunlop et al. |
| 6,977,250 B2 | 12/2005 | Rodriguez |
| 6,978,945 B2 | 12/2005 | Wong et al. |
| 6,994,862 B2 | 2/2006 | Jeong et al. |
| 6,995,149 B1 | 2/2006 | Endrikat et al. |
| 7,004,321 B1 | 2/2006 | Palm et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Gray et al. |
| 7,030,157 B2 | 4/2006 | Huazhu et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf et al. |
| 7,094,228 B2 | 8/2006 | Zhang et al. |
| 7,097,853 B1 | 8/2006 | Garbe et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B1 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich et al. |
| 7,470,433 B2 | 12/2008 | Carrara et al. |
| 7,485,666 B2 | 2/2009 | Villanueva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Wyrwa et al. |
| 7,550,142 B2 | 6/2009 | Giles-Komar et al. |
| 7,563,565 B1 | 7/2009 | Matsuo et al. |
| 7,569,274 B2 | 8/2009 | Besse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,615,547 B2 | 11/2009 | Reiner |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Griswold et al. |
| RE42,012 E | 12/2010 | Deaver et al. |
| 7,850,992 B2 | 12/2010 | Kim et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh et al. |
| 7,945,459 B2 | 5/2011 | Grace et al. |
| 7,960,368 B2 | 6/2011 | Nickisch et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Coelingh et al. |
| 8,071,729 B2 | 12/2011 | Giles-Komar et al. |
| 8,075,916 B2 | 12/2011 | Song et al. |
| 8,075,917 B2 | 12/2011 | Chung et al. |
| 8,076,317 B2 | 12/2011 | Kulmann |
| 8,076,319 B2 | 12/2011 | Leonard |
| 8,080,553 B2 | 12/2011 | Keith et al. |
| 8,088,605 B2 | 1/2012 | Beaudet et al. |
| 8,096,940 B2 | 1/2012 | Josephson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernas et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Bayly et al. |
| 8,182,833 B2 | 5/2012 | Hermsmeyer |
| 8,187,615 B2 | 5/2012 | Friedman |
| 8,195,403 B2 | 6/2012 | Ishikawa et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Theone et al. |
| 8,222,237 B2 | 7/2012 | Nickisch et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,273,730 B2 | 9/2012 | Fernandez et al. |
| 8,287,888 B2 | 10/2012 | Song et al. |
| 8,288,366 B2 | 10/2012 | Chochinov et al. |
| 8,318,898 B2 | 11/2012 | Fasel et al. |
| 8,324,193 B2 | 12/2012 | Lee-Sepsick et al. |
| 8,329,680 B2 | 12/2012 | Evans et al. |

(56) References Cited

U.S. PATENT DOCUMENTS

| | | | |
|---|---|---|---|
| 8,337,814 B2 | 12/2012 | Osbakken et al. | |
| 8,344,007 B2 | 1/2013 | Tang et al. | |
| 8,349,820 B2 | 1/2013 | Zeun et al. | |
| 8,353,863 B2 | 1/2013 | Imran | |
| 8,357,723 B2 | 1/2013 | Satyam | |
| 8,361,995 B2 | 1/2013 | Schramm | |
| 8,362,091 B2 | 1/2013 | Tamarkin et al. | |
| 8,372,424 B2 | 2/2013 | Berry et al. | |
| 8,372,806 B2 | 2/2013 | Bohler et al. | |
| 8,377,482 B2 | 2/2013 | Laurie et al. | |
| 8,377,994 B2 | 2/2013 | Gray et al. | |
| 8,394,759 B2 | 3/2013 | Barathur et al. | |
| 8,415,332 B2 | 4/2013 | Diliberti et al. | |
| 8,420,111 B2 | 4/2013 | Hermsmeyer | |
| 8,435,561 B2 | 5/2013 | Besins et al. | |
| 8,435,972 B2 | 5/2013 | Stein et al. | |
| 8,449,879 B2 | 5/2013 | Laurent-Applegate et al. | |
| 8,450,108 B2 | 5/2013 | Boyce | |
| 8,454,945 B2 | 6/2013 | McCook et al. | |
| 8,455,468 B2 | 6/2013 | Hoffman et al. | |
| 8,461,138 B2 | 6/2013 | Boissonneault | |
| 8,476,252 B2 | 7/2013 | Achleitner et al. | |
| 8,481,488 B2 | 7/2013 | Carter | |
| 8,486,374 B2 | 7/2013 | Tamarkin et al. | |
| 8,486,442 B2 | 7/2013 | Matsushita et al. | |
| 8,492,368 B2 | 7/2013 | Vanlandingham et al. | |
| 8,507,467 B2 | 8/2013 | Matsui et al. | |
| 8,512,693 B2 | 8/2013 | Capito et al. | |
| 8,512,754 B2 | 8/2013 | Needham | |
| 8,518,376 B2 | 8/2013 | Tamarkin et al. | |
| 8,536,159 B2 | 9/2013 | Li et al. | |
| 8,540,967 B2 | 9/2013 | Barrett et al. | |
| 8,541,400 B2 | 9/2013 | Johnsson et al. | |
| 8,551,462 B2 | 10/2013 | Goldstein et al. | |
| 8,557,281 B2 | 10/2013 | Halliday et al. | |
| 8,568,374 B2 | 10/2013 | De et al. | |
| 8,591,951 B2 | 11/2013 | Kohn et al. | |
| 8,592,490 B2 | 11/2013 | Legen et al. | |
| 8,613,951 B2 | 12/2013 | Zale et al. | |
| 8,633,178 B2 | 1/2014 | Bernick et al. | |
| 8,633,180 B2 | 1/2014 | Li et al. | |
| 8,636,787 B2 | 1/2014 | Sabaria | |
| 8,636,982 B2 | 1/2014 | Tamarkin et al. | |
| 8,653,129 B2 | 2/2014 | Fein et al. | |
| 8,658,627 B2 | 2/2014 | Voskuhl | |
| 8,658,628 B2 | 2/2014 | Baucom | |
| 8,663,681 B2 | 3/2014 | Ahmed et al. | |
| 8,663,692 B1 | 3/2014 | Mueller et al. | |
| 8,663,703 B2 | 3/2014 | Lerner et al. | |
| 8,664,207 B2 | 3/2014 | Li et al. | |
| 8,669,293 B2 | 3/2014 | Levy et al. | |
| 8,679,552 B2 | 3/2014 | Guthery | |
| 8,694,358 B2 | 4/2014 | Tryfon | |
| 8,697,127 B2 | 4/2014 | Sah | |
| 8,697,710 B2 | 4/2014 | Li et al. | |
| 8,703,105 B2 | 4/2014 | Tamarkin et al. | |
| 8,703,179 B2 | 4/2014 | Boga et al. | |
| 8,709,385 B2 | 4/2014 | Tamarkin et al. | |
| 8,709,451 B2 | 4/2014 | Rapoport et al. | |
| 8,715,735 B2 | 5/2014 | Funke et al. | |
| 8,721,331 B2 | 5/2014 | Raghuprasad | |
| 8,722,021 B2 | 5/2014 | Friedman et al. | |
| 8,734,846 B2 | 5/2014 | Ali et al. | |
| 8,735,381 B2 | 5/2014 | Podolski | |
| 8,741,336 B2 | 6/2014 | Dipierro et al. | |
| 8,741,373 B2 | 6/2014 | Bromley et al. | |
| 8,753,661 B2 | 6/2014 | Steinmuller-Nethl et al. | |
| 8,784,882 B2 | 7/2014 | Mattern | |
| 8,815,261 B2 | 8/2014 | Hanma | |
| 8,846,077 B2 | 9/2014 | Dewitt | |
| 8,846,648 B2 | 9/2014 | Bernick et al. | |
| 8,846,649 B2 | 9/2014 | Bernick et al. | |
| 8,933,059 B2 | 1/2015 | Bernick et al. | |
| 8,987,237 B2 | 3/2015 | Bernick et al. | |
| 8,987,238 B2 | 3/2015 | Bernick et al. | |
| 8,993,548 B2 | 3/2015 | Bernick et al. | |
| 8,993,549 B2 | 3/2015 | Bernick et al. | |
| 9,006,222 B2 | 4/2015 | Bernick et al. | |
| 9,012,434 B2 | 4/2015 | Bernick et al. | |
| 9,248,136 B2 | 2/2016 | Bernick et al. | |
| 9,931,349 B2 * | 4/2018 | Shadiack | A61K 9/0053 |
| 10,098,894 B2 * | 10/2018 | Amadio | A61K 31/57 |
| 2001/0005728 A1 | 6/2001 | Guittard et al. | |
| 2001/0009673 A1 | 7/2001 | Lipp et al. | |
| 2001/0018072 A1 | 8/2001 | Unger | |
| 2001/0021816 A1 | 9/2001 | Caillouette | |
| 2001/0023261 A1 | 9/2001 | Ryoo et al. | |
| 2001/0027189 A1 | 10/2001 | Bennink et al. | |
| 2001/0029357 A1 | 10/2001 | Bunt et al. | |
| 2001/0031747 A1 | 10/2001 | Deziegler et al. | |
| 2001/0032125 A1 | 10/2001 | Bhan et al. | |
| 2001/0034340 A1 | 10/2001 | Pickar | |
| 2001/0053383 A1 | 12/2001 | Miranda et al. | |
| 2001/0056068 A1 | 12/2001 | Chwalisz et al. | |
| 2002/0012710 A1 | 1/2002 | Lansky | |
| 2002/0026158 A1 | 2/2002 | Rathbone et al. | |
| 2002/0028788 A1 | 3/2002 | Bunt et al. | |
| 2002/0035070 A1 | 3/2002 | Gardlik et al. | |
| 2002/0039594 A1 | 4/2002 | Unger | |
| 2002/0058648 A1 | 5/2002 | Hammerly | |
| 2002/0058926 A1 | 5/2002 | Rathbone et al. | |
| 2002/0064541 A1 | 5/2002 | Lapidot et al. | |
| 2002/0076441 A1 | 6/2002 | Shih et al. | |
| 2002/0102308 A1 | 8/2002 | Wei et al. | |
| 2002/0107230 A1 | 8/2002 | Waldon et al. | |
| 2002/0114803 A1 | 8/2002 | Deaver et al. | |
| 2002/0119174 A1 | 8/2002 | Gardlik et al. | |
| 2002/0119198 A1 | 8/2002 | Gao et al. | |
| 2002/0132801 A1 | 9/2002 | Heil et al. | |
| 2002/0137749 A1 | 9/2002 | Levinson et al. | |
| 2002/0142017 A1 | 10/2002 | Simonnet | |
| 2002/0151530 A1 | 10/2002 | Leonard et al. | |
| 2002/0156394 A1 | 10/2002 | Mehrotra et al. | |
| 2002/0169150 A1 | 11/2002 | Pickar | |
| 2002/0169205 A1 | 11/2002 | Chwalisz et al. | |
| 2002/0173510 A1 | 11/2002 | Levinson et al. | |
| 2002/0193356 A1 | 12/2002 | Van et al. | |
| 2002/0193758 A1 | 12/2002 | Sandberg | |
| 2002/0197286 A1 | 12/2002 | Brandman et al. | |
| 2003/0003139 A1 | 1/2003 | Lipp et al. | |
| 2003/0004145 A1 | 1/2003 | Leonard | |
| 2003/0007994 A1 | 1/2003 | Bunt et al. | |
| 2003/0027772 A1 | 2/2003 | Breton | |
| 2003/0044434 A1 | 3/2003 | Gao et al. | |
| 2003/0044453 A1 | 3/2003 | Dittgen et al. | |
| 2003/0049307 A1 | 3/2003 | Gyurik | |
| 2003/0064097 A1 | 4/2003 | Patel et al. | |
| 2003/0064975 A1 | 4/2003 | Koch et al. | |
| 2003/0072760 A1 | 4/2003 | Sirbasku | |
| 2003/0073248 A1 | 4/2003 | Roth et al. | |
| 2003/0073673 A1 | 4/2003 | Hesch | |
| 2003/0077297 A1 | 4/2003 | Chen et al. | |
| 2003/0078245 A1 | 4/2003 | Bennink et al. | |
| 2003/0091620 A1 | 5/2003 | Fikstad et al. | |
| 2003/0091640 A1 | 5/2003 | Ramanathan et al. | |
| 2003/0092691 A1 | 5/2003 | Besse et al. | |
| 2003/0096012 A1 | 5/2003 | Besse et al. | |
| 2003/0104048 A1 | 6/2003 | Patel et al. | |
| 2003/0109507 A1 | 6/2003 | Franke et al. | |
| 2003/0113268 A1 | 6/2003 | Buenafae et al. | |
| 2003/0114420 A1 | 6/2003 | Salvati et al. | |
| 2003/0114430 A1 | 6/2003 | MacLeod et al. | |
| 2003/0124182 A1 | 7/2003 | Shojaei et al. | |
| 2003/0124191 A1 | 7/2003 | Besse et al. | |
| 2003/0125283 A1 | 7/2003 | Gatenby | |
| 2003/0130558 A1 | 7/2003 | Massara et al. | |
| 2003/0144258 A1 | 7/2003 | Heil et al. | |
| 2003/0157157 A1 | 8/2003 | Luo et al. | |
| 2003/0166509 A1 | 9/2003 | Edwards et al. | |
| 2003/0170295 A1 | 9/2003 | Kim et al. | |
| 2003/0175329 A1 | 9/2003 | Azarnoff et al. | |
| 2003/0175333 A1 | 9/2003 | Shefer et al. | |
| 2003/0180352 A1 | 9/2003 | Patel et al. | |
| 2003/0181353 A1 | 9/2003 | Nyce | |

(56) References Cited

U.S. PATENT DOCUMENTS

| | | |
|---|---|---|
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Caubel et al. |
| 2003/0225048 A1 | 12/2003 | Caubel et al. |
| 2003/0225050 A1 | 12/2003 | Grawe et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou et al. |
| 2004/0073024 A1 | 4/2004 | Metcalf et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0091541 A1 | 5/2004 | Unger |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini-Eteve et al. |
| 2004/0115226 A1 | 6/2004 | Li et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Fernandez et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Basu et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Morris et al. |
| 2005/0020552 A1 | 1/2005 | Aschkenasy et al. |
| 2005/0021009 A1 | 1/2005 | Massara et al. |
| 2005/0025833 A1 | 2/2005 | Aschkenasy et al. |
| 2005/0031651 A1 | 2/2005 | Gervais et al. |
| 2005/0042173 A1 | 2/2005 | Besse et al. |
| 2005/0042268 A1 | 2/2005 | Aschkenasy et al. |
| 2005/0048116 A1 | 3/2005 | Straub et al. |
| 2005/0054991 A1 | 3/2005 | Tobyn et al. |
| 2005/0079138 A1 | 4/2005 | Chickering et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky et al. |
| 2005/0147659 A1 | 7/2005 | Carli et al. |
| 2005/0152956 A1 | 7/2005 | Dudley |
| 2005/0153946 A1 | 7/2005 | Hirsh et al. |
| 2005/0164977 A1 | 7/2005 | Coelingh |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Popp et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0238675 A1 | 10/2005 | Li et al. |
| 2005/0239747 A1 | 10/2005 | Yang et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0266088 A1 | 12/2005 | Hinrichs et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0013873 A1 | 1/2006 | Yang et al. |
| 2006/0014728 A1 | 1/2006 | Chwalisz et al. |
| 2006/0018937 A1 | 1/2006 | Friedman et al. |
| 2006/0019978 A1 | 1/2006 | Balog et al. |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0073203 A1 | 4/2006 | Ljusberg-Wahren et al. |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Meconi et al. |
| 2006/0089337 A1 | 4/2006 | Casper et al. |
| 2006/0093557 A1 | 5/2006 | Dickinson et al. |
| 2006/0093678 A1 | 5/2006 | Chickering et al. |
| 2006/0100180 A1 | 5/2006 | Nubbemeyer et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich et al. |
| 2006/0134188 A1 | 6/2006 | Podhaisky et al. |
| 2006/0135619 A1 | 6/2006 | Kick et al. |
| 2006/0165744 A1 | 7/2006 | Jamil et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Brodbeck et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |

(56) References Cited

U.S. PATENT DOCUMENTS

| | | |
|---|---|---|
| 2006/0247221 A1 | 11/2006 | Coelingh et al. |
| 2006/0251581 A1 | 11/2006 | McIntyre et al. |
| 2006/0252049 A1 | 11/2006 | Shuler et al. |
| 2006/0252738 A1 | 11/2006 | Avelino et al. |
| 2006/0257472 A1 | 11/2006 | Nielsen |
| 2006/0275218 A1 | 12/2006 | Tamarkin et al. |
| 2006/0275360 A1 | 12/2006 | Ahmed et al. |
| 2006/0276414 A1 | 12/2006 | Coelingh et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0287301 A1 | 12/2006 | McNair |
| 2006/0292223 A1 | 12/2006 | Woolfson et al. |
| 2007/0004693 A1 | 1/2007 | Woolfson et al. |
| 2007/0004694 A1 | 1/2007 | Woolfson et al. |
| 2007/0009559 A1 | 1/2007 | Li et al. |
| 2007/0009594 A1 | 1/2007 | Grubb et al. |
| 2007/0010550 A1 | 1/2007 | Mckenzie |
| 2007/0014839 A1 | 1/2007 | Bracht |
| 2007/0015698 A1 | 1/2007 | Kleinman et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0036831 A1 | 2/2007 | Baker |
| 2007/0037780 A1 | 2/2007 | Ebert et al. |
| 2007/0037782 A1 | 2/2007 | Hibino et al. |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Gargiulo et al. |
| 2007/0148194 A1 | 6/2007 | Amiji et al. |
| 2007/0154533 A1 | 7/2007 | Dudley |
| 2007/0167418 A1 | 7/2007 | Ferguson |
| 2007/0178051 A1 | 8/2007 | Pruitt et al. |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Bacopoulos et al. |
| 2007/0191319 A1 | 8/2007 | Ke et al. |
| 2007/0191599 A1 | 8/2007 | Hill et al. |
| 2007/0196415 A1 | 8/2007 | Chen et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Galey et al. |
| 2007/0238713 A1 | 10/2007 | Gast et al. |
| 2007/0243229 A1 | 10/2007 | Smith et al. |
| 2007/0248658 A1 | 10/2007 | Zurdo et al. |
| 2007/0254858 A1 | 11/2007 | Cronk |
| 2007/0255197 A1 | 11/2007 | Humberstone et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | Devries et al. |
| 2007/0287688 A1 | 12/2007 | Chan et al. |
| 2007/0287789 A1 | 12/2007 | Jones et al. |
| 2007/0292359 A1 | 12/2007 | Friedman et al. |
| 2007/0292387 A1 | 12/2007 | Jon et al. |
| 2007/0292461 A1 | 12/2007 | Tamarkin et al. |
| 2007/0292493 A1 | 12/2007 | Brierre |
| 2007/0298089 A1 | 12/2007 | Saeki et al. |
| 2008/0026035 A1 | 1/2008 | Chollet et al. |
| 2008/0026040 A1 | 1/2008 | Farr et al. |
| 2008/0026062 A1 | 1/2008 | Farr et al. |
| 2008/0038219 A1 | 2/2008 | Mosbaugh et al. |
| 2008/0038350 A1 | 2/2008 | Gerecke et al. |
| 2008/0039405 A1 | 2/2008 | Langley et al. |
| 2008/0050317 A1 | 2/2008 | Tamarkin et al. |
| 2008/0051351 A1 | 2/2008 | Ghisalberti |
| 2008/0063607 A1 | 3/2008 | Tamarkin et al. |
| 2008/0069779 A1 | 3/2008 | Tamarkin et al. |
| 2008/0069791 A1 | 3/2008 | Beissert |
| 2008/0085877 A1 | 4/2008 | Bortz |
| 2008/0095831 A1 | 4/2008 | Mc |
| 2008/0095838 A1 | 4/2008 | Abou |
| 2008/0102127 A1 | 5/2008 | Gao et al. |
| 2008/0113953 A1 | 5/2008 | De et al. |
| 2008/0114050 A1 | 5/2008 | Fensome et al. |
| 2008/0119537 A1 | 5/2008 | Zhang et al. |
| 2008/0125402 A1 | 5/2008 | Diliberti et al. |
| 2008/0138379 A1 | 6/2008 | Jennings-Spring |
| 2008/0138390 A1 | 6/2008 | Hsu et al. |
| 2008/0139392 A1 | 6/2008 | Acosta-Zara et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Liu et al. |
| 2008/0175908 A1 | 7/2008 | Liu et al. |
| 2008/0188829 A1 | 8/2008 | Creasy et al. |
| 2008/0206156 A1 | 8/2008 | Cronk |
| 2008/0206159 A1 | 8/2008 | Tamarkin et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Tang et al. |
| 2008/0227763 A1 | 9/2008 | Lanquetin et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Hedner et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Allart et al. |
| 2009/0011041 A1 | 1/2009 | Musaeva et al. |
| 2009/0017120 A1 | 1/2009 | Trimble et al. |
| 2009/0022683 A1 | 1/2009 | Song et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De et al. |
| 2009/0081303 A1 | 3/2009 | Savoir et al. |
| 2009/0088393 A1 | 4/2009 | Spilburg |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Liu et al. |
| 2009/0130029 A1 | 5/2009 | Tamarkin et al. |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Holm et al. |
| 2009/0197843 A1 | 8/2009 | Notelovitz et al. |
| 2009/0203658 A1 | 8/2009 | Marx et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy et al. |
| 2009/0269403 A1 | 10/2009 | Snaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |

(56) References Cited

U.S. PATENT DOCUMENTS

| | | |
|---|---|---|
| 2009/0324714 A1 | 12/2009 | Liu et al. |
| 2009/0325916 A1 | 12/2009 | Zhang et al. |
| 2010/0008985 A1 | 1/2010 | Pellikaan et al. |
| 2010/0028360 A1 | 2/2010 | Atwood |
| 2010/0034838 A1 | 2/2010 | Staniforth et al. |
| 2010/0034880 A1 | 2/2010 | Sintov et al. |
| 2010/0040671 A1 | 2/2010 | Ahmed et al. |
| 2010/0048523 A1 | 2/2010 | Bachman et al. |
| 2010/0055138 A1 | 3/2010 | Margulies et al. |
| 2010/0062067 A1 | 3/2010 | Tonge et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Shenoy et al. |
| 2010/0143481 A1 | 6/2010 | Shenoy et al. |
| 2010/0150993 A1 | 6/2010 | Theobald et al. |
| 2010/0151010 A1 | 6/2010 | Petereit et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh et al. |
| 2010/0190758 A1 | 7/2010 | Fauser et al. |
| 2010/0204326 A1 | 8/2010 | D'Souza |
| 2010/0210994 A1 | 8/2010 | Zarif |
| 2010/0221195 A1 | 9/2010 | Tamarkin et al. |
| 2010/0227797 A1 | 9/2010 | Axelson et al. |
| 2010/0240626 A1 | 9/2010 | Kulkarni et al. |
| 2010/0247482 A1 | 9/2010 | Cui et al. |
| 2010/0247632 A1 | 9/2010 | Dong et al. |
| 2010/0247635 A1 | 9/2010 | Rosenberg et al. |
| 2010/0255085 A1 | 10/2010 | Liu et al. |
| 2010/0272779 A1 | 10/2010 | Jackson |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Shoichet et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Dipietro et al. |
| 2010/0330168 A1 | 12/2010 | Gicquel et al. |
| 2011/0014296 A1 | 1/2011 | Chen et al. |
| 2011/0028439 A1 | 2/2011 | Witt-Enderby et al. |
| 2011/0039814 A1 | 2/2011 | Huatan et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De et al. |
| 2011/0098258 A1 | 4/2011 | Masini-Eteve et al. |
| 2011/0098631 A1 | 4/2011 | McIntyre et al. |
| 2011/0104268 A1 | 5/2011 | Pachot et al. |
| 2011/0104289 A1 | 5/2011 | Savoir et al. |
| 2011/0130372 A1 | 6/2011 | Agostinacchio et al. |
| 2011/0135719 A1 | 6/2011 | Besins et al. |
| 2011/0137057 A1 | 6/2011 | Frincke |
| 2011/0142914 A1 | 6/2011 | Persaud et al. |
| 2011/0142945 A1 | 6/2011 | Chen et al. |
| 2011/0152840 A1 | 6/2011 | Lee et al. |
| 2011/0158920 A1 | 6/2011 | Morley et al. |
| 2011/0171140 A1 | 7/2011 | Illum et al. |
| 2011/0182997 A1 | 7/2011 | Lewis et al. |
| 2011/0190201 A1 | 8/2011 | Hyde et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Bruno-Raimondi et al. |
| 2011/0244043 A1 | 10/2011 | Xu et al. |
| 2011/0250256 A1 | 10/2011 | Hyun-Oh et al. |
| 2011/0250259 A1 | 10/2011 | Buckman |
| 2011/0250274 A1 | 10/2011 | Snaked et al. |
| 2011/0256092 A1 | 10/2011 | Phiasivongsa et al. |
| 2011/0262373 A1 | 10/2011 | Umbert |
| 2011/0262494 A1 | 10/2011 | Achleitner et al. |
| 2011/0268665 A1 | 11/2011 | Tamarkin et al. |
| 2011/0275584 A1 | 11/2011 | Wilckens et al. |
| 2011/0281832 A1 | 11/2011 | Li et al. |
| 2011/0287094 A1 | 11/2011 | Penhasi et al. |
| 2011/0293720 A1 | 12/2011 | General et al. |
| 2011/0294738 A1 | 12/2011 | Ren et al. |
| 2011/0300167 A1 | 12/2011 | McMurry et al. |
| 2011/0301087 A1 | 12/2011 | McBride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Combal et al. |
| 2012/0028936 A1 | 2/2012 | Gloger et al. |
| 2012/0045532 A1 | 2/2012 | Cohen |
| 2012/0046264 A1 | 2/2012 | Simes et al. |
| 2012/0046518 A1 | 2/2012 | Yoakum et al. |
| 2012/0052077 A1 | 3/2012 | Truitt, III et al. |
| 2012/0058171 A1 | 3/2012 | De et al. |
| 2012/0058962 A1 | 3/2012 | Cumming et al. |
| 2012/0058979 A1 | 3/2012 | Keith et al. |
| 2012/0064135 A1 | 3/2012 | Levin et al. |
| 2012/0065179 A1 | 3/2012 | Andersson |
| 2012/0065221 A1 | 3/2012 | Babul |
| 2012/0087872 A1 | 4/2012 | Tamarkin et al. |
| 2012/0101073 A1 | 4/2012 | Mannion et al. |
| 2012/0121517 A1 | 5/2012 | Song et al. |
| 2012/0121692 A1 | 5/2012 | Xu et al. |
| 2012/0122829 A1 | 5/2012 | Taravella et al. |
| 2012/0128625 A1 | 5/2012 | Shalwitz et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Li et al. |
| 2012/0142645 A1 | 6/2012 | Marx |
| 2012/0148670 A1 | 6/2012 | Kim et al. |
| 2012/0149748 A1 | 6/2012 | Shanler et al. |
| 2012/0172343 A1 | 7/2012 | Lindenthal et al. |
| 2012/0184515 A1 | 7/2012 | Klar et al. |
| 2012/0231052 A1 | 9/2012 | Sitruk-Ware et al. |
| 2012/0232011 A1 | 9/2012 | Kneissel et al. |
| 2012/0232042 A1 | 9/2012 | Klar et al. |
| 2012/0263679 A1 | 10/2012 | Marlow et al. |
| 2012/0269721 A1 | 10/2012 | Weng et al. |
| 2012/0269878 A2 | 10/2012 | Cantor et al. |
| 2012/0277249 A1 | 11/2012 | Andersson et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Zhang et al. |
| 2012/0301538 A1 | 11/2012 | Gordon-Beresford et al. |
| 2012/0302535 A1 | 11/2012 | Caufriez et al. |
| 2012/0316130 A1 | 12/2012 | Hendrix |
| 2012/0316496 A1 | 12/2012 | Hoffmann et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0328701 A1 | 12/2012 | Edelson et al. |
| 2012/0329738 A1 | 12/2012 | Liu |
| 2013/0004619 A1 | 1/2013 | Chow et al. |

(56) References Cited

U.S. PATENT DOCUMENTS

| | | |
|---|---|---|
| 2013/0011342 A1 | 1/2013 | Tamarkin et al. |
| 2013/0017239 A1 | 1/2013 | Viladot et al. |
| 2013/0022674 A1 | 1/2013 | Dudley et al. |
| 2013/0023505 A1 | 1/2013 | Garfield et al. |
| 2013/0023823 A1 | 1/2013 | Simpson et al. |
| 2013/0028850 A1 | 1/2013 | Tamarkin et al. |
| 2013/0029947 A1 | 1/2013 | Nachaegari et al. |
| 2013/0029957 A1 | 1/2013 | Giliyar et al. |
| 2013/0045266 A1 | 2/2013 | Choi et al. |
| 2013/0045953 A1 | 2/2013 | Sitruk-Ware et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Li et al. |
| 2013/0089574 A1 | 4/2013 | Schmidt-Gollwitzer et al. |
| 2013/0090318 A1 | 4/2013 | Ulmann et al. |
| 2013/0102781 A1 | 4/2013 | Bevill et al. |
| 2013/0108551 A1 | 5/2013 | Langereis et al. |
| 2013/0116215 A1 | 5/2013 | Coma et al. |
| 2013/0116222 A1 | 5/2013 | Arnold et al. |
| 2013/0122051 A1 | 5/2013 | Abidi et al. |
| 2013/0123175 A1 | 5/2013 | Hill et al. |
| 2013/0123220 A1 | 5/2013 | Queiroz |
| 2013/0123351 A1 | 5/2013 | Dewitt |
| 2013/0129818 A1* | 5/2013 | Bernick .................. A61K 9/16 424/451 |
| 2013/0131027 A1 | 5/2013 | Pakkalin et al. |
| 2013/0131028 A1 | 5/2013 | Snyder et al. |
| 2013/0131029 A1 | 5/2013 | Bakker et al. |
| 2013/0149314 A1 | 6/2013 | Bullerdiek et al. |
| 2013/0164225 A1 | 6/2013 | Tamarkin et al. |
| 2013/0164346 A1 | 6/2013 | Lee et al. |
| 2013/0165744 A1 | 6/2013 | Carson et al. |
| 2013/0178452 A1 | 7/2013 | King |
| 2013/0183254 A1 | 7/2013 | Zhou et al. |
| 2013/0183325 A1 | 7/2013 | Bottoni et al. |
| 2013/0189193 A1 | 7/2013 | Tamarkin et al. |
| 2013/0189196 A1 | 7/2013 | Tamarkin et al. |
| 2013/0189230 A1 | 7/2013 | Shoichet et al. |
| 2013/0189368 A1 | 7/2013 | Mosqueira et al. |
| 2013/0209539 A1 | 8/2013 | Loxley et al. |
| 2013/0210709 A1 | 8/2013 | McMurry et al. |
| 2013/0216550 A1 | 8/2013 | Penninger et al. |
| 2013/0216596 A1 | 8/2013 | Viladot et al. |
| 2013/0224177 A1 | 8/2013 | Kim et al. |
| 2013/0224257 A1 | 8/2013 | Sah et al. |
| 2013/0224268 A1 | 8/2013 | Alam et al. |
| 2013/0224300 A1 | 8/2013 | Maggio |
| 2013/0225412 A1 | 8/2013 | Sardari et al. |
| 2013/0225542 A1 | 8/2013 | Poegh et al. |
| 2013/0226113 A1 | 8/2013 | Schumacher et al. |
| 2013/0243696 A1 | 9/2013 | Wang et al. |
| 2013/0245253 A1 | 9/2013 | Marx et al. |
| 2013/0245570 A1 | 9/2013 | Jackson |
| 2013/0261096 A1 | 10/2013 | Merian et al. |
| 2013/0266645 A1 | 10/2013 | Becker et al. |
| 2013/0267485 A1 | 10/2013 | Da |
| 2013/0273167 A1 | 10/2013 | Lee et al. |
| 2013/0274211 A1 | 10/2013 | Burman et al. |
| 2013/0280213 A1 | 10/2013 | Voskuhl |
| 2013/0316374 A1 | 11/2013 | Penninger et al. |
| 2013/0317065 A1 | 11/2013 | Tatani et al. |
| 2013/0317315 A1 | 11/2013 | Lu et al. |
| 2013/0324565 A1 | 12/2013 | Li et al. |
| 2013/0331363 A1 | 12/2013 | Li et al. |
| 2013/0338122 A1 | 12/2013 | Bernick et al. |
| 2013/0338123 A1 | 12/2013 | Bernick et al. |
| 2013/0338124 A1 | 12/2013 | Li et al. |
| 2013/0345187 A1 | 12/2013 | Rodriguez |
| 2014/0018335 A1 | 1/2014 | Tatani et al. |
| 2014/0024590 A1 | 1/2014 | Weidhaas et al. |
| 2014/0031289 A1 | 1/2014 | Song et al. |
| 2014/0031323 A1 | 1/2014 | Perez |
| 2014/0066416 A1 | 3/2014 | Leunis et al. |
| 2014/0072531 A1 | 3/2014 | Kim et al. |
| 2014/0079686 A1 | 3/2014 | Barman et al. |
| 2014/0088051 A1 | 3/2014 | Bernick et al. |
| 2014/0088058 A1 | 3/2014 | Maurizio |
| 2014/0088059 A1 | 3/2014 | Perumal et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Bernick et al. |
| 2014/0113889 A1 | 4/2014 | Connor et al. |
| 2014/0127185 A1 | 5/2014 | Stein et al. |
| 2014/0127280 A1 | 5/2014 | Duesterberg et al. |
| 2014/0127308 A1 | 5/2014 | Opara et al. |
| 2014/0128798 A1 | 5/2014 | Janson et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Li et al. |
| 2014/0206616 A1 | 7/2014 | Ko et al. |
| 2014/0213565 A1 | 7/2014 | Bernick et al. |
| 2014/0234428 A1 | 8/2014 | Barathur et al. |
| 2014/0271884 A1 | 9/2014 | Prud'Homme et al. |
| 2014/0287027 A1 | 9/2014 | Schiffelers et al. |
| 2014/0288035 A1 | 9/2014 | Hübner et al. |
| 2014/0329783 A1 | 11/2014 | Bernick et al. |
| 2014/0335193 A1 | 11/2014 | Rintoul et al. |
| 2014/0335194 A1 | 11/2014 | Lee et al. |
| 2014/0370084 A1 | 12/2014 | Bernick et al. |
| 2014/0370110 A1 | 12/2014 | Perumal et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0118164 A1 | 4/2015 | Tamarkin et al. |
| 2015/0133421 A1 | 5/2015 | Bernick et al. |
| 2015/0148323 A1 | 5/2015 | Cacace et al. |
| 2015/0164812 A1 | 6/2015 | Holm et al. |
| 2015/0202211 A1 | 7/2015 | Amadio et al. |
| 2016/0030449 A1* | 2/2016 | Persicaner ............ A61K 31/57 514/170 |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |
| 2017/0281776 A1 | 10/2017 | Shadiack et al. |
| 2017/0340739 A1 | 11/2017 | Cacace et al. |
| 2018/0280411 A1* | 10/2018 | Shadiack ............. A61K 9/0053 |
| 2019/0070197 A1* | 3/2019 | Amadio ................ A61K 31/57 |

FOREIGN PATENT DOCUMENTS

| | | |
|---|---|---|
| EP | 0275716 A1 | 7/1988 |
| EP | 0622075 A1 | 11/1994 |
| EP | 0785211 A1 | 7/1997 |
| EP | 0785212 A1 | 7/1997 |
| EP | 0811381 A1 | 12/1997 |
| EP | 1043973 A1 | 10/2000 |
| EP | 0904064 B1 | 10/2001 |
| EP | 0750495 B1 | 12/2002 |
| EP | 1283674 A2 | 2/2003 |
| EP | 0811381 B1 | 5/2003 |
| EP | 0999826 B1 | 5/2004 |
| EP | 1094781 B1 | 7/2008 |
| EP | 2191833 A1 | 6/2010 |
| EP | 2101729 B1 | 3/2011 |
| EP | 1778187 B1 | 5/2012 |
| EP | 2191833 B1 | 2/2013 |
| EP | 2172497 B1 | 5/2013 |
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |

(56) References Cited

FOREIGN PATENT DOCUMENTS

| | | |
|---|---|---|
| GB | 2098865 B | 12/1985 |
| IN | 216026 | 3/2008 |
| IN | 53/KOL/2005 | 9/2009 |
| IN | 244217 | 11/2010 |
| WO | WO-9011064 A1 | 10/1990 |
| WO | WO-9317686 A1 | 9/1993 |
| WO | WO-9422426 A1 | 10/1994 |
| WO | WO-9524893 A1 | 9/1995 |
| WO | WO-9530409 A1 | 11/1995 |
| WO | WO-9609826 A2 | 4/1996 |
| WO | WO-9619975 A1 | 7/1996 |
| WO | WO-9630000 A1 | 10/1996 |
| WO | WO-9705491 A1 | 2/1997 |
| WO | WO-9740823 A1 | 11/1997 |
| WO | WO-9743989 A1 | 11/1997 |
| WO | WO-9810293 A1 | 3/1998 |
| WO | WO-9832465 A1 | 7/1998 |
| WO | WO-9851280 A1 | 11/1998 |
| WO | WO-9932072 A1 | 7/1999 |
| WO | WO-9932089 A1 | 7/1999 |
| WO | WO-9939700 A1 | 8/1999 |
| WO | WO-9942109 A1 | 8/1999 |
| WO | WO-9943304 A1 | 9/1999 |
| WO | WO-9948477 A1 | 9/1999 |
| WO | WO-9953910 A2 | 10/1999 |
| WO | WO-9963974 A2 | 12/1999 |
| WO | WO-0001351 A1 | 1/2000 |
| WO | WO-0006120 A1 | 2/2000 |
| WO | WO-0006175 A1 | 2/2000 |
| WO | WO-0038659 A1 | 7/2000 |
| WO | WO-0045795 A2 | 8/2000 |
| WO | WO-0050007 A1 | 8/2000 |
| WO | WO-0059577 A1 | 10/2000 |
| WO | WO-0076522 A1 | 12/2000 |
| WO | WO-0137808 A1 | 5/2001 |
| WO | WO-0154699 A1 | 8/2001 |
| WO | WO-0160325 A1 | 8/2001 |
| WO | WO-0207700 A2 | 1/2002 |
| WO | WO-0211768 A1 | 2/2002 |
| WO | WO-0222132 A2 | 3/2002 |
| WO | WO-0240008 A2 | 5/2002 |
| WO | WO-0241878 A2 | 5/2002 |
| WO | WO-02053131 A1 | 7/2002 |
| WO | WO-02078604 A2 | 10/2002 |
| WO | WO-02078602 A3 | 2/2003 |
| WO | WO-03028667 A2 | 4/2003 |
| WO | WO-03041718 A1 | 5/2003 |
| WO | WO-03041741 A1 | 5/2003 |
| WO | WO-03068186 A1 | 8/2003 |
| WO | WO-03077923 A1 | 9/2003 |
| WO | WO-03082254 A1 | 10/2003 |
| WO | WO-03092588 A2 | 11/2003 |
| WO | WO-2004014397 A1 | 2/2004 |
| WO | WO-2004014432 A1 | 2/2004 |
| WO | WO-2004017983 A1 | 3/2004 |
| WO | WO-2004032897 A2 | 4/2004 |
| WO | WO-2004052336 A2 | 6/2004 |
| WO | WO-2004054540 A2 | 7/2004 |
| WO | WO-2004080413 A2 | 9/2004 |
| WO | WO-2005004917 A2 | 1/2005 |
| WO | WO-2005027911 A1 | 3/2005 |
| WO | WO-2005030175 A1 | 4/2005 |
| WO | WO-2005081825 A2 | 9/2005 |
| WO | WO-2005087194 A1 | 9/2005 |
| WO | WO-2005087199 A2 | 9/2005 |
| WO | WO-2005105040 A2 | 11/2005 |
| WO | WO-2005105059 A1 | 11/2005 |
| WO | WO-2005115335 A1 | 12/2005 |
| WO | WO-2005120470 A1 | 12/2005 |
| WO | WO-2005120517 A1 | 12/2005 |
| WO | WO-2006013369 A2 | 2/2006 |
| WO | WO-2006034090 A1 | 3/2006 |
| WO | WO-2006036899 A2 | 4/2006 |
| WO | WO-2006053172 A2 | 5/2006 |
| WO | WO-2006105615 A1 | 10/2006 |
| WO | WO-2006113505 A2 | 10/2006 |
| WO | WO-2006138686 A1 | 12/2006 |
| WO | WO-2006138735 A2 | 12/2006 |
| WO | WO-2007045027 A1 | 4/2007 |
| WO | WO-2007103294 A2 | 9/2007 |
| WO | WO-2006138735 A3 | 10/2007 |
| WO | WO-2007120868 A2 | 10/2007 |
| WO | WO-2007123790 A1 | 11/2007 |
| WO | WO-2007124250 A2 | 11/2007 |
| WO | WO-2007124250 A3 | 12/2007 |
| WO | WO-2007144151 A1 | 12/2007 |
| WO | WO-2007103294 A3 | 4/2008 |
| WO | WO-2008049516 A3 | 6/2008 |
| WO | WO-2008077823 A1 | 7/2008 |
| WO | WO-2008152444 A2 | 12/2008 |
| WO | WO-2009002542 A1 | 12/2008 |
| WO | WO-2009036311 A1 | 3/2009 |
| WO | WO-2009040818 A1 | 4/2009 |
| WO | WO-2008152444 A3 | 6/2009 |
| WO | WO-2009069006 A2 | 6/2009 |
| WO | WO-2009098072 A2 | 8/2009 |
| WO | WO-2009098072 A3 | 10/2009 |
| WO | WO-2009069006 A3 | 11/2009 |
| WO | WO-2009133352 A2 | 11/2009 |
| WO | WO-2010033188 A2 | 3/2010 |
| WO | WO-2009133352 A3 | 10/2010 |
| WO | WO-2010146872 A1 | 12/2010 |
| WO | WO-2011000210 A1 | 1/2011 |
| WO | WO-2011073995 A2 | 6/2011 |
| WO | WO-2011073995 A3 | 8/2011 |
| WO | WO-2010033188 A3 | 9/2011 |
| WO | WO-2011120084 A1 | 10/2011 |
| WO | WO-2011128336 A1 | 10/2011 |
| WO | WO-2012009778 A2 | 1/2012 |
| WO | WO-2012024361 A1 | 2/2012 |
| WO | WO-2012055814 A1 | 5/2012 |
| WO | WO-2012055840 A1 | 5/2012 |
| WO | WO-2012065740 A1 | 5/2012 |
| WO | WO-2012098090 A1 | 7/2012 |
| WO | WO-2012116277 A1 | 8/2012 |
| WO | WO-2012118563 A2 | 9/2012 |
| WO | WO-2012120365 A1 | 9/2012 |
| WO | WO-2012127501 A2 | 9/2012 |
| WO | WO-2012156561 A1 | 11/2012 |
| WO | WO-2012156822 A1 | 11/2012 |
| WO | WO-2012158483 A2 | 11/2012 |
| WO | WO-2012166909 A1 | 12/2012 |
| WO | WO-2012170578 A1 | 12/2012 |
| WO | WO-2013011501 A1 | 1/2013 |
| WO | WO-2012009778 A3 | 2/2013 |
| WO | WO-2013025449 A1 | 2/2013 |
| WO | WO-2013028639 A1 | 2/2013 |
| WO | WO-2013035101 A1 | 3/2013 |
| WO | WO-2013044067 A1 | 3/2013 |
| WO | WO-2013045404 A2 | 4/2013 |
| WO | WO-2013059285 A1 | 4/2013 |
| WO | WO 2013/078422 A2 | 5/2013 |
| WO | WO-2013063279 A1 | 5/2013 |
| WO | WO-2013064620 A1 | 5/2013 |
| WO | WO-2013071281 A1 | 5/2013 |
| WO | WO-2013088254 A1 | 6/2013 |
| WO | WO-2013102665 A1 | 7/2013 |
| WO | WO-2013106437 A1 | 7/2013 |
| WO | WO-2013113690 A1 | 8/2013 |
| WO | WO-2013124415 A1 | 8/2013 |
| WO | WO-2013127727 A1 | 9/2013 |
| WO | WO-2013127728 A1 | 9/2013 |
| WO | WO-2013144356 A1 | 10/2013 |
| WO | WO-2013149258 A2 | 10/2013 |
| WO | WO-2013158454 A2 | 10/2013 |
| WO | WO-2013170052 A1 | 11/2013 |
| WO | WO-2013178587 A1 | 12/2013 |
| WO | WO-2013181449 A1 | 12/2013 |
| WO | WO-2013192248 A1 | 12/2013 |
| WO | WO-2013192249 A1 | 12/2013 |
| WO | WO-2013192250 A1 | 12/2013 |
| WO | WO-2013192251 A1 | 12/2013 |
| WO | WO-2014001904 A1 | 1/2014 |
| WO | WO-2014004424 A1 | 1/2014 |

(56) References Cited

FOREIGN PATENT DOCUMENTS

| | | |
|---|---|---|
| WO | WO-2014009434 A1 | 1/2014 |
| WO | WO-2014018569 A1 | 1/2014 |
| WO | WO-2014018570 A1 | 1/2014 |
| WO | WO-2014018571 A2 | 1/2014 |
| WO | WO-2014018856 A1 | 1/2014 |
| WO | WO-2014018932 A2 | 1/2014 |
| WO | WO-2014031958 A1 | 2/2014 |
| WO | WO-2014041120 A1 | 3/2014 |
| WO | WO-2014052792 A1 | 4/2014 |
| WO | WO-2014056897 A1 | 4/2014 |
| WO | WO-2014066442 A2 | 5/2014 |
| WO | WO-2014074846 A1 | 5/2014 |
| WO | WO-2014076231 A1 | 5/2014 |
| WO | WO-2014076569 A2 | 5/2014 |
| WO | WO-2014081598 A1 | 5/2014 |
| WO | WO-2014086739 A1 | 6/2014 |
| WO | WO-2014093114 A1 | 6/2014 |
| WO | WO-2014104784 A1 | 7/2014 |
| WO | WO-2014197008 A1 | 12/2014 |

OTHER PUBLICATIONS

Williams et al. International Journal of Pharmaceutics 1991, 74, 157-168.*
Monti et al. Drug Delivery 2009, 16 (5), 237-242.*
Sun Alternative Medicine Review 2007, 12 (3), 259-264.*
Fingerova et al. Ceska Gynekol. 2003, 68 (2), 117-121, English Abstract.*
D-Limonene IARC 1993, 56, 135.*
Degenhardt, J., "Monoterpene and Sesquiterpene Synthases and the Origin of Terpene Skeletal Diversity in Plants," *Phytochemistry* e70(15-16):1621-1637, Elsevier, England (2009).
Hanson, J.R., "13. Terpenoids and Steroids," *Annual Reports Section B (Organic Chemistry)* 82:353-375, Royal Society of Chemistry, England (1985).
Lauer, A.C., et al., "Evaluation of the Hairless Rat as a Model for in Vivo Percutaneous Absorption," *Journal of Pharmaceutical Sciences* 86(1):13-18, American Chemical Society and American Pharmaceutical Association, United States (1997).
Palamakula, A., et al., "Preparation and In Vitro Characterization of Self-Nanoemulsified Drug Delivery Systems of Coenzyme Q10 Using Chiral Essential Oil Components," Pharmaceutical Technology pp. 74-88, accessed at http://images.alfresco.advanstar.com/alfresco_images/pharma/2014/08/22/97292023-0e75-4736-82d1-df2e08ffd626/article-128365.pdf, accessed on Apr. 25, 2017 (2004).
Tuleu, C., et al., "Comparative Bioavailability Study in Dogs of a Self-Emulsifying Formulation of Progesterone Presented in a Pellet and Liquid Form Compared with an Aqueous Suspension of Progesterone," *Journal of Pharmaceutical Sciences* 93(6):1495-1502, Wiley-Liss, Inc., United States (2004).
Cremer Oleo, "Cremer Care, IMWITOR® 988, INCI: Glyceryl Caprylate," accessed at http://s3.amazonaws.com/petercremeerna/products/spec_sheets/448/773/262/original/TDSC_IMWITOR_988_e.pdf?1385268551, accessed on May 23, 2017, 4 pages.
Doren, M., et al., "Effects of Specific Post-menopausal Hormone Therapies on Bone Mineral Density in Post-Menopausal Women: A Meta-Analysis," *Human Reproduction* 18(8):1737-1746, European Society of Human Reproduction and Embryology, England (2003).
International Search Report and Written Opinion for International Application No. PCT/US17/24955, ISA/US, Alexandria, dated Jun. 12, 2017, 11 pages.
Williams, A.C. and Barry, B.W., "The Enhancement Index Concept Applied to Terpene Penetration Enhancers for Human Skin and Model Lipophilic (oestradiol) and Hydrophilic (5-fluorouracil) Drugs," *International Journal of Pharmaceutics* 74(2-3):157-168, Elsevier Science Publishers B.V., Netherlands (1991).
Abbas, M.A., et al., "Regression of Endometrial Implants Treated with Vitamin D3 in a Rat Model of Endometriosis," European Journal of Pharmacology 715(1-3):72-75, Elsevier Science, Netherlands (2013).

Abitec, CapmuiMCM, EP, Technical Data Sheet, version 10, 2014, Columbus, OH.
Abitec, CapmuiMCM, NF, Technical Data Sheet, version 6, 2014, Columbus, OH.
Abitec, CapmuiMCM, Safety Data Sheet, 2011, Janesville, WI.
Abitec, CapmuiMCM, Technical Data Sheet, version 17, 2014, Columbus, OH.
Abitec, CapmuiPG8, CAS No. 31565-12-5, version 11,2006, Columbus, OH.
Abitec Corporation Excipients for the Pharmaceutical Industry—Regulatory and Product Information, 2 pages (2013).
Acarturk, F., "Mucoadhesive Vaginal Drug Delivery Systems," Recent patents on drug delivery & formulation 3(3):193-205, Bentham Science Publishers, United Arab Emirates (2009).
Acog, Mckinlay, et al., "Practice Bulletin, Clinical Management Guidelines for Obstetrician-Gynecologists," , Obstetrics & Gynecology Agog, No. 141, vol. 123(1), 202-216, (2014).
Advisory Action dated Jan. 29, 2007 for U.S. Appl. No. 12/561,515, filed Sep. 17, 2009.
Alabi, K. A., et al., "Analysis of Fatty Acid Composition ofThevetia peruviana and Hura crepitans Seed oils using GC-FID," Fountain Journal of Natural and Applied Sciences 2(2):32-7, Osogbo (2013).
Alexander, KS, Corn Oil, CAS No. 8001-30-7, (2009).
Alvarez, P., et al., "Ectopic Uterine Tissue as a Chronic Pain Generator," Neuroscience 225:269-282, Elsevier Science, United States (2012).
Application Note JASCO CD Spectra of Pharmaceuticals Substances Steroids, 2 pages.
Araya-Sibaja, A.M., et al., "Morphology Study of Progesterone Polymorphs Prepared by Polymer-induced Heteronucleation (Pihn)," Scanning 35(4):213-221, John Wiley & Sons, United States (2013).
Araya-Sibaja, Andrea Manela, et al., "Chemical Properties of Progesterone Selected Refer," SciFinder, American Chemical Society & US National. Library. of Med, (2014).
Araya-Sibaja, Andrea Manela, et al., "Polymorphism in Progesterone," SciFinder, pp. 1-46, American Chemical Society & US National. Library. of Med, (2014).
Araya-Sibaja, Andrea Manela, et al., "Polymorphism in Progesterone Selected References," SciFinder, pp. 1-12, American Chemical Society & US National. Library. of Med, (2014).
Araya-Sibaja., et al., "Crystallization of progesterone polymorphs using polymer-induced heteronucleation (PIHn) method," Drug Development and Industrial Pharmacy, Early Online, pp. 1-8, Informa Healthcare (2014).
Archer, D.F., et al., "Effects of Ospemifene on the Female Reproductive and Urinary Tracts : Translation From Preclinical Models into Clinical Evidence," Menopause, Lippincott-Raven Publishers, United States (2014).
Archer, F., et al., "Estrace® vs Premarin® for Treatment of Menopausal Symptoms: Dosage Comparison Study 9(1):21-31, (1992).
Ashburn, A.D., et al., "Cardiovascular , Hepatic and Renal Lesions in Mice Receiving Cortisone , Estrone and Progesterone," The Yale Journal of Biology and Medicine 35:329-340, Yale Journal of Biology and Medicine, United States (1963).
Azeem, A., et al., "Microemulsions as a Surrogate Carrier for Dermal Drug Delivery," Drug development and industrial pharmacy 35(5):525-547, Informa Healthcare, England (2009).
Azure Pharma, Inc., "ELESTRIN—estradiol gel" Drug Info, http://dailymed.nlm.nih.gov/dailymed/archives/ fdaDrugInfo.cfm?archiveid=11885, 26 pages, (2009).
Bakhmutova-Albert, Ekaterina, et al.,"Enhancing Aqueous Dissolution Rates of Progesterone via Cocrystallization," SSCI, Division of Aptuit, Poster No. R6247, West Lafayette.
Banerjee, S., et al., "On the Stability of Salivary Progesterone Under Various Conditions of Storage," Steroids 46(6):967-974, Elsevier, United States (1985).
Barnett. and Steven, M., "Pressure-tuning infared and solution Raman spectroscopic studies of 17B-estradiol and several A-ring," Vibrational Spectroscopy, vol. 8, pp. 263, (1995).
Bartosova, L. and Bajgar, J., "Transdermal Drug Delivery in Vitro Using Diffusion Cells," Current Medicinal Chemistry 19(27):4671-4677, Bentham Science Publishers, Netherlands (2012).

(56) References Cited

OTHER PUBLICATIONS

Benbow, A.L. and Waddell, B.J., "Distribution and Metabolism of Maternal Progesterone in the Uterus, Placenta, and Fetus During Rat Pregnancy," Biology of Reproduction 52(6):1327-1333, Society for the Study of Reproduction, United States (1995).
Bernabei, M.T., et al., "[Release of Polymorphic forms of Progesterone From Dimethylpolysiloxane Matrices]," Bollettino chimico farmaceutico 122(1):20-26, Societa Editoriale Farmaceutica, Italy (1983).
Busetta, P.B., et al., "Structure Cristalline et Moleculaire du Complexe Oestradiol-Propanol," Acta Crystallographica B28:1349-1351 (1972).
Busetta, P.B. and Hospital, M., "Structure Cristalline et Moleculair de l'Oestradiol Hemihydrate," Acta Crystallographica B28:560-567, (1972).
Bhavnani, B.R. and Stanczyk, F.Z., "Misconception and Concerns About Bioidentical Hormones Used for Custom-Compounded Hormone Therapy," The Journal of clinical endocrinology and metabolism 97(3):756-759, Endocrine Society, United States (2012).
Bhavnani, B.R. and Stanczyk, F.Z., "Pharmacology of Conjugated Equine Estrogens: Efficacy, Safety and Mechanism of Action," The Journal of steroid biochemistry and molecular biology 142:16-29, Pergamon, England (2014).
Bhavnani, B.R., et al., "Structure Activity Relationships and Differential interactions and Functional Activity of Various Equine Estrogens Mediated via Estrogen Receptors (Ers) Eralpha and Erbeta," Endocrinology 149(10):4857-4870, Endocrine Society, United States (2008).
BioMed Centrai,Solubility of Progesterone in Organic Solvents, Online PDF, http://www.biomedcentral.com/content/ supplementary/1475-2859-11-106-S2.pdf.
Blake, E.J., et al., "Single and Multidose Pharmacokinetic Study of a Vaginal Micronized Progesterone insert (Endometrin ) Compared with Vaginal Gel in Healthy Reproductive-Aged Female Subjects," Fertility and Sterility 94(4):1296-1301, Elsevier for the American Society for Reproductive Medicine, United States (2010).
Borka. and Laszlo., Crystal Polymorphism of Pharmaceuticals, Acta Pharmaceutica Jugoslavia 40:71-94, (1990).
Brandstatter-Kuhnert, M., Kofler A., "Zur mikroskopischen Identitatsprufung and zur Polymorphie der Sexualhormone," Microchimica Acta 6:847-853, Springer-Verlag, Germany (1959).
Christensson, J.B., et al., "Positive Patch Test Reactions to Oxidized Limonene: Exposure and Relevance," Contact Dermatitis 71(5):264-272, Wiley, England (2014).
Brinton, L.A. and Felix, A.S., "Menopausal Hormone Therapy and Risk of Endometrial Cancer," The Journal of steroid biochemistry and molecular biology 142:83-89, Pergamon, England (2014).
"British Pharmacopoeia 2014 Online, Refined Maize Oil, Ph. Eur. Monograph 1342, voll & II, Monographs: Medicinal and Pharmaceutical Substances, accessed at http:/www.pharmacopoeia.co.uklbp2014/ixbin/bp.egi?a=print&id=7400&tab=a-z%20index[Feb. 3, 2014 1:37:50 PM]".
Burry, K.A., et al., "Percutaneous Absorption of Progesterone in Postmenopausal Women Treated with Transdermal Estrogen," American journal of obstetrics and gynecology 180(6Pt1):1504-1511, Elsevier, United States (1999).
Campsteyn, H., et al., "Structure Cristalline et Molcculaire de la Progesterone C21H3002," Acta Crystallographica B28 :3032-3042, (1972).
Cendejas-Santana, G., et al., "Growth and characterization of progesterone crystallites," Revista Mexicana de Fisica 50 S(1) : 1-3, (2004).
ChemPro, Top-Notch Technology in Production of Oils and Fats, Chempro-Edible-Oii-Refining-ISO-TUV-Austria.
Christen, R.D., et al., "Phase I/Pharmacokinetic Study of High-Dose Progesterone and Doxorubicin," Journal of Clinical Oncology : Official Journal of the American Society of Clinical Oncology 11(12):2417-2426, American Society of Clinical Oncology, United States (1993).

Christensson, J.B., et al., "Limonene Hydroperoxide Analogues Differ in Allergenic Activity," Contact Dermatitis 59(6):344-352, Wiley, England (2008).
Christensson, J.B., et al., "Limonene Hydroperoxide Analogues Show Specific Patch Test Reactions," Contact Dermatitis 70(5):291-299, Wiley, England (2014).
Chun et al., "Transdermal Delivery of Estradiol and Norethindrone Acetate: Effect of Vehicles and Pressure Sensitive Adhesive Matrix," Journal of Korean Pharmaceutical Sciences 35(3):173-177, (2005).
Cicinelli, E., et al., "Direct Transport of Progesterone From Vagina to Uterus," Obstetrics and Gynecology 95(3):403-406, Lippincott Williams & Wilkins, United States (2000).
Committee of Obstetric Practice, Committee Opinion—No. 522, Obstetrics & Gynecology, 119(4):879-882, (2012).
Commodari, F., et al., "Comparison of 17Beta-Estradiol Structures From X-Ray Diffraction and Solution Nmr," Magnetic resonance in chemistry : MRC 43(6):444-450, Wiley Heyden, England (2005).
Cooper, A., et al., "Systemic Absorption of Progesterone From Progest Cream in Postmenopausal Women," Lancet 351(9111):1255-1256, Lancet Publishing Group, England (1998).
International Search Report and written opinion for International Application No. PCT/US13/46442, dated Nov. 1, 2013.
International Search Report and written opinion for International Application No. PCT/US13/46443, dated Oct. 31, 2013.
International Search Report and written opinion for International Application No. PCT/US13/46444, dated Oct. 31, 2013.
International Search Report and written opinion for International Application No. PCT/US13/46445, dated Nov. 1, 2013.
International Search Report and Written Opinion for related International Application No. PCT/US13/023309, dated Apr. 9, 2013.
International Search report for corresponding International Application No. PCT/US12/66406, dated Jan. 24, 2013.
Corbett, S.H., et al., "Trends in Pharmacy Compounding for Women'S Health in North Carolina : Focus on Vulvodynia," Southern Medical Journal 107(7):433-436, Southern Medical Association, United States (2014).
Corn Refiners Assoc. Com Oil, Edition 5, United States (2006).
Critchley, H.O., et al., "Estrogen Receptor Beta, but Not Estrogen Receptor Alpha, Is Present in the Vascular Endothelium of the Human and Nonhuman Primate Endometrium," The Journal of Clinical Endocrinology and Metabolism 86(3):1370-1378, Endocrine Society, United States (2001).
Dauqan, Eqbal M.A., et al., "Fatty Acids Composition of Four Different Vegetable Oils (Red Palm Olein, Palm Olein, Corn Oil," IPCBEE, 14, IACSIT Press, Singapore (2011).
Dideberg, O., et al., "Crystal data on progesterone (C21H3002), desoxycorticosterone (C21H3003), corticosterone (C21H3004) and aldosterone," Journal of Applied Crystallography 4:80, (1971).
Diramio, J.A., et al., "Poly(Ethylene Glycol) Methacrylate/Dimethacrylate Hydrogels for Controlled Release of Hydrophobic Drugs," Masters of Science Thesis, University of Georgia, Athens, Georgia, 131 pages (2002).
Diramio. "Polyethylene Glycol Methacrylate/Dimetacrylate Hydrogels for Controlled Release of Hydrophobic Drugs," The University of Georgia-Masters of Science Thesis, http://athenaeum.libs.uga.edu/bitstream/handle/10724/7820/diramio_jackie_a_200412_ms.pdf?sequence=1, 131 pages, (2004).
Drakulic, B.J., et al., "Role of Complexes formation Between Drugs and Penetration Enhancers in Transdermal Delivery," International journal of pharmaceutics 363(1-2):40-49, Elsevier/North-Holland Biomedical Press., Netherlands (2008).
Du, J.Y., et al., "Percutaneous Progesterone Delivery via Cream or Gel Application in Postmenopausal Women : A Randomized Cross-Over Study of Progesterone Levels in Serum , Whole Blood , Saliva , and Capillary Blood," Menopause 20(11):1169-1175, Lippincott-Raven Publishers, United States (2013).
Duclos, R., et al., "Polymorphism of Progesterone: Influence of the carrier and of the solid dispersion manufacturing process. A calorimetric and radiocrystallographic study," Journal of Thermal Analysis 37:1869-1875, John Wiley & Sons, England (1991).
Ebian, A.R., "Ebian Article: Polymorphism and solvation of ethinyl estradiol," Pharmaceutica Acta Helvetiae 54(4):111-114, (1979).

(56) References Cited

OTHER PUBLICATIONS

Eisenberger, A. and Westhoff, C., "Hormone Replacement Therapy and Venous Thromboembolism," The Journal of steroid biochemistry and molecular biology 142:76-82, Pergamon, England (2014).
Engelhardt, H., et al., "Conceptus influences the Distribution of Uterine Leukocytes During Early Porcine Pregnancy," Biology of Reproduction 66(6):1875-1880, Society for the Study of Reproduction, United States (2002).
Ettinger, B., et al., "Comparison of Endometrial Growth Produced by Unopposed Conjugated Estrogens or by Micronized Estradiol in Postmenopausal Women," American Journal of Obstetrics and Gynecology 176(1 Pt1):112-117, Elsevier, United States (1997).
Excipients for Pharmaceuticals, Sasol Olefins & Surfactants GMBH, 28 pages (2010).
Faassen, F., et al., "Physicochemical Properties and Transport of Steroids Across Caco-2 Cells," Pharmaceutical research 20(2):177-186, Kluwer Academic/Plenum Publishers, United States (2003).
"FDA, Draft Guidance on Progesterone, accessed at http://www.fda.gov/downloads/Drugs/GuidanceComplianceRegulatoryInformation/Guidances/UCM209294.pdf, accessed on (Recommended) Apr. 2010,(Revised) Feb. 2011,".
Ferrari, Roseli AP., et al., "Oxidative Stability of Biodiesel From Soybean Oil Fatty Acid Ethyl Esters," Scientia Agricola 62(3):291-95, Piracicaba, brazil (2005).
Filipsson,F., et al., "Concise International Chemical Assessment Document 5," Limonene, first draft, World Health Organization, Geneva, 36 pages (1998).
Final Office Action dated Jul. 16, 2013 for U.S. Appl. No. 13/684,002, filed Nov. 21, 2012.
Final Office Action dated Oct. 26, 2012for U.S. Appl. No. 12/561,515, filed Sep. 17, 2009.
Flyvholm, M.A. and Menne, T., "Sensitizing Risk of butylated Hydroxytoluene Based on Exposure and Effect Data," Contact Dermatitis 23(5):341-345, Wiley, England (1990).
Fotherby. K., "Bioavailability of Orally Administered Sex Steroids Used in Oral Contraception and Hormone Replacement Therapy," Contraception 54(2):59-69, Elsevier, United States (1996).
Franklin, R.D. and Kutteh, W.H., "Characterization of Immunoglobulins and Cytokines in Human Cervical Mucus : influence of Exogenous and Endogenous Hormones," Journal of Reproductive Immunology 42(2):93-106, Elsevier/North-Holland Biomedical Press, Ireland (1999).
Franz, T.J., et al., "Use of Excised Human Skin to Assess the Bioequivalence of Topical Products," Skin Pharmacology and Physiology 22(5):276-286, Karger, Switzerland (2009).
Freedman, R.R., "Menopausal Hot Flashes: Mechanisms, Endocrinology, Treatment," The Journal of steroid biochemistry and molecular biology 142:115-120, Pergamon, England (2014).
Fuchs, K.O., et al., "The Effects of an Estrogen and Glycolic Acid Cream on the Facial Skin of Postmenopausal Women: A Randomized Histologic Study," Aesthetic Dermatology 8(1):14-19, (2006).
Fuchs, K.O., et al., "The Effects of an Estrogen and Glycolic Acid Cream on the Facial Skin of Postmenopausal Women: A Randomized Histologic Study," Cutis 71(6):481-488, Frontline Medical Communications, United States (2003).
Fuchs, K.O., et al., "The Effects of an Estrogen and Glycolic Acid Cream on the Facial Skin of Postmenopausal Women: A Randomized Histologic Study," Pharmacology/Cosmetology 5(1), (2006).
Fugh-Berman, A. and Bythrow, J., "Bioidentical Hormones for Menopausal Hormone Therapy: Variation on a Theme," Journal of general internal medicine 22(7):1030-1034, Springer, United States (2007).
Furness, S., et al., "Hormone therapy in Postmenopausal Women and Risk of Endometrial Hyperplasia," The Cochrane Database Of Systematic Reviews 8:1-204, Wiley, England (2012).
Gafvert, E., et al., "Free Radicals in Antigen formation: Reduction of Contact Allergic Response to Hydroperoxides by Epidermal Treatment with Antioxidants," The British Journal of Dermatology 146(4):649-656, Blackwell Scientific Publications, England (2002).

Ganem-Quintanar., et al., "Evaluation of the transepidermal permeation of diethylene glycol monoethyl ether and skin water loss," International Journal of Pharmaceutics, 147(2):165-171, (1997) Abstract Only.
Gattefossé SAS, Regulatory Data Sheet, Gelot 64, 6 pages (2012).
Gattefossé SAS, Regulatory Data Sheet, Lauroglycol 90, 5 pages (2012).
Gattefosse, "Excipients for Safe and Effective Topical Delivery," http://drug-dev.com/Main/Back-Issues/Transdermal-Topical-Subcutaneous-NonInvasive-Deliv-5.aspx# (2012).
Gattefosse SAS, Material Safety Data Sheet, Gelot 64, 8 pages 2012.
Gillet, J.Y., et al., "induction of Amenorrhea During Hormone Replacement therapy : Optimal Micronized Progesterone Dose a Multicenter Study," Maturitas 19(2):103-115, Elsevier/North Holland Biomedical Press, Ireland (1994).
Giron, D., "Thermal analysis and calorimetric methods in the characterisation of polymorphs and solvates," Thermochimica Acta 248:1-59, Elsevier B.V., Netherlands (1995).
Giron-Forest, D., et al., "Thermal Analysis Methods for Pharmacopoeial Materials," Journal of pharmaceutical and biomedical analysis 7(12):1421-1433, Elsevier Science, England (1989).
Glaser, R.L., et al., "Pilot Study : Absorption and Efficacy of Multiple Hormones Delivered in a Single Cream Applied to the Mucous Membranes of the Labia and Vagina," Gynecologic and Obstetric Investigation 66(2):111-118,Basel, New York, Karger., Switzerland (2008).
Golatowski, C., et al., "Comparative Evaluation of Saliva Collection Methods for Proteome Analysis," International Journal of Clinical Chemistry 419:42-46,Elsevier., Netherlands (2013).
Graham, J.D. and Clarke, C.L., "Physiological Action of Progesterone in Target Tissues," Endocrine Reviews 18(4):502-519, Endocrine Society, United States (1997).
Groothuis, P.G., et al., "Estrogen and the Endometrium : Lessons Learned From Gene Expression Profiling in Rodents and Human," Human Reproduction Update 13(4):405-417, Published for the European Society of Human Reproduction and Embryology by Oxford University Press, England (2007).
Gunstone, Frank, D., et al., "Vegetable Oils in Food Technology: Composition, Properties and Uses," Blackwell Publishing, CRC Press, (2002).
Gurney, E.P., et al., "The Women"S Health initiative Trial and Related Studies: 10 Years Later: A Clinician"S View," The Journal of steroid biochemistry and molecular biology 142:42105, Pergamon, England (2014).
Hamid, K.A., et al., "The Effects of Common Solubilizing Agents on the intestinal Membrane Barrier Functions and Membrane Toxicity in Rats," International Journal Of Pharmaceutics 379(1):100-108,Amsterdam, Elsevier/North-Holland Biomedical Press., Netherlands (2009).
Hapgood, J.P., et al., "Potency of Progestogens Used in Hormonal Therapy: Toward Understanding Differential Actions," The Journal of steroid biochemistry and molecular biology 142:39-47, Pergamon, England (2014).
Hargrove, J.T., et al., "Menopausal Hormone Replacement Therapy with Continuous Daily Oral Micronized Estradiol and Progesterone," Obstetrics and gynecology 73(4):606-612, Lippincott Williams & Wilkins, United States (1989).
Haner B.A., and Norton, D.A., "Crystal data (I) for some pregnenes and pregnadienes," Acta Crystallographica 17:1610, (1964).
Hatton, J., et al., "Safety and Efficacy of a Lipid Emulsion Containing Medium-Chain Triglycerides," Clinical Pharmacy 9(5):366-371, American Society of Hospital Pharmacists, United States (1990).
He, F., et al., "Apoptotic Signaling Pathways in Uteri of Rats with Endometrial Hyperplasia induced by Ovariectomy Combined with Estrogen," Gynecologic and Obstetric Investigation 76(1):51-56,Karger., Switzerland (2013).
Helbling, I.M., et al., "The Optimization of an intravaginal Ring Releasing Progesterone Using a Mathematical Model," Pharmaceutical research 31(3):795-808, Kluwer Academic/Plenum Publishers, United States (2014).

(56) References Cited

OTHER PUBLICATIONS

Helmy, A., et al, "Estrogenic Effect of Soy Phytoestrogens on the Uterus of Ovariectomized Female Rats," Clinical Pharmacology & Biopharmaceutics, S2, 7 pages (2014).
Henderson, V.W., "Alzheimer"S Disease: Review of Hormone Therapy Trials and Implications for Treatment and Prevention After Menopause," The Journal of steroid biochemistry and molecular biology 142:99-106, Pergamon, England (2014).
Henriksen. Thormod, et al., "An ENDOR Sturdy of Radiation-Induced Molecular Damage to Progesterone," Journal of Magnetic Resonance 63(2):333-342, Elsevier Inc., United States (1985).
Hodis, H.N. and Mack, W.J., "Hormone Replacement Therapy and the association with Coronary Heart Disease and Overall Mortality: Clinical Application of the Timing Hypothesis," The Journal of steroid biochemistry and molecular biology 142:68-75, Pergamon, England (2014).
Hospital, M., et al., "X-Ray Crystallography of Estrogens and Their Binding to Receptor Sites," Molecular pharmacology 8(4):438-445, American Society for Pharmacology and Experimental Therapeutics, United States (1972).
Hostynek, J., et al., "Predictinga bsorptiono f fragrancec hemicalst hrough human skin," Journal of the Society of Cosmetic Chemists 46:221-229, (1995).
Hulsmann, S., et al., "Stability of Extruded 17 Beta-Estradiol Solid Dispersions," Pharmaceutical Development and Technology 6(2):223-229, Informa Healthcare, England (2001).
Hurn, P.D. and Macrae, I.M., "Estrogen as a Neuroprotectant in Stroke," Journal of Cerebral Blood Flow and Metabolism : Official Journal of the International Society of Cerebral Blood Flow and Metabolism 20(4):631-652, Nature Publishing Group, United States (2000).
Hyder, S.M., et al., "Synthetic Estrogen 17Alpha-Ethinyl Estradiol induces Pattern of Uterine Gene Expression Similar to Endogenous Estrogen 17Beta-Estradiol," The Journal of Pharmacology and Experimental Therapeutics 290(2):740-747, American Society for Pharmacology and Experimental Therapeutics, United States (1999).
Johanson, G., "Toxicity Review of Ethylene Glycol Monomethyl Ether and its Acetate Ester," Critical reviews in toxicology 30(3):307-345, Informa Healthcare, England (2000).
Johnson, S., Williams, and John, F.W. Keana , "Racemic Progesterone," Tetrahedron Letters 4(4):193-196, Pergamon Press Ltd., United Kingdom (1963).
Joshi, S.G., et al., "Detection and Synthesis of a Progestagen-Dependent Protein in Human Endometrium," Journal of Reproduction and Fertility 59(2):273-285, Portland Press, England (1980).
Kanno J., et al., "The Oecd Program to Validate the Rat Uterotrophic Bioassay to Screen Compounds for in Vivo Estrogenic Responses : Phase 1," Environmental Health Perspectives 109(8):785-794,N. C. National Institute of Environmental Health Sciences., United States (2001).
Karlberg, A.T., et al., "Air Oxidation of D-Limonene (the Citrus Solvent) Creates Potent Allergens," Contact Dermatitis 26(5):332-340, Wiley, England (1992).
Karlberg, A.T., et al., "influence of an Anti-Oxidant on the formation of Allergenic Compounds During Auto-Oxidation of D-Limonene," The Annals of Occupational Hygiene 38(2):199-207, Oxford University Press, England (1994).
Kaunitz, A.M. "Extended Duration Use of Menopausal Hormone therapy," Menopause 21(6):679-681, Lippincott-Raven Publishers, United States (2014).
Khalil, S.A.H., "Stability and Dissolution Rates of Corticosteroids in Polyethylene Glycol Solid Dispersions," Drug Development and Industrial Pharmacy 10(5):771-787, Marcel Dekker, New York (1984).
Kharode, Y., et al., "The Pairing of a Selective Estrogen Receptor Modulator, Bazedoxifene, with Conjugated Estrogens as a New Paradigm for the Treatment of Menopausal Symptoms and Osteoporosis Prevention," Endocrinology 149(12):6084-6091, Endocrine Society, United States (2008).
Kim, Y.W., et al., "Safety Evaluation and Risk Assessment of D-Limonene," Journal of Toxicology and Environmental Health. Part B, Critical Reviews 16(1):17-38, Informa Healthcare, England (2013).
Kincl, F.A., et al., "Increasing Oral Bioavailability of Progesterone by formulation," Journal of steroid biochemistry 9(1):83-84, Pergamon Press, England (1978).
Knuth., et al., "Hydrogel delivery systems for vaginal and oral applications: Formulation and biological considerations," Advanced Drug Delivery Reviews, 11(1-2):137-167, (1993) Abstract Only.
Koga, K., et al., "Enhancing Mechanism of Labrasol on intestinal Membrane Permeability of the Hydrophilic Drug Gentamicin Sulfate," European Journal of Pharmaceutics and Biopharmaceutics : Official Journal of Arbeitsgemeinschaft Fur Pharmazeutische Verfahrenstechnik E.V 64(1):82-91, Elsevier Science, Netherlands (2006).
Komm, B.S., et al., "Bazedoxifene Acetate : A Selective Estrogen Receptor Modulator with Improved Selectivity," Endocrinology 146(9):3999-4008, Endocrine Society, United States (2005).
Korkmaz, Filiz, "Biophysical Studies of Progesterone-Model Membrane Interactions," A Thesis Submitted to the Graduate School of Natural and Applied Sciences of the Middle East Technical University (2003).
Kotiyan, P.N. and Vavia, P.R., "Stability indicating Hptic Method for the Estimation of Estradiol," Journal of pharmaceutical and biomedical analysis 22(4):667-671, Elsevier Science, England (2000).
Krzyminiewski, R., et al., "EPR Study of the Stable Radical in a y-Irradialed Single Crystal of Progesterone," Journal of Magnetic Resonance 46:300-305, Acedemic Press, England (1982).
Kubli-Garfias, C., et al., "Ab initio calculations of the electronic structure of glucocorticoids," Journal of Molecular Structure, Theochem 454(2-3):267-275, Elsevier Science B.V., Netherlands (1998).
Kubli-Garfias, Carlos, "Ab initio study of the electronic structure of progesterone and related progestins," Journal of Molecular Structure, Theochem 425(1-2):171-179, Elsevier B.V., Netherlands (1998).
Kuhnert-Brandstaetier, M., Kofler, A., "Zur Unterscheidung von losungsmittelhaltigen pseudopolymorphen Kristallformen und polymorphen Modifikationen bei Steroidhormonen.II.," 1:127-139, Mikrochimica Acta (1968).
Kuhnert-Brandstaetier, M., Lnder, R., "Zur Hydratbildung bei Steroidhormonen," Sci. Pharm. 41(2):109-116, (1973).
Kuhnert-Brandstatier, M., "Thermo-microscopic and spectrophotometric: Determination of steroid hormones," Microchemical Journal 9:105-133, (1965).
Kumasaka, T., et al., "Effects of Various forms of Progestin on the Endometrium of the Estrogen-Primed , Ovariectomized Rat," Endocrine Journal 41(2):161-169, Japan Endocrine Society, Japan (1994).
Kuon, R.J. and Garfield, R.E., "Actions of Progestins for the inhibition of Cervical Ripening and Uterine Contractions to Prevent Preterm Birth," Facts, Views &Amp; Vision in Obgyn 4(2):110-119,Flemish Society of Obstetrics & Gynaecology, Belgium (2012).
Kuon, R.J., et al., "A Novel Optical Method to Assess Cervical Changes During Pregnancy and Use to Evaluate the Effects of Progestins on Term and Preterm Labor," American Journal of Obstetrics and Gynecology 205(1):82.e15-82.e20, Elsevier, United States (2011).
Kuon, R.J., et al., "Pharmacologic Actions of Progestins to inhibit Cervical Ripening and Prevent Delivery Depend on their Properties , the Route of Administration , and the Vehicle," American Journal of Obstetrics and Gynecology 202(5):455.e1-455.e9, Elsevier, United States (2010).
Labrie, et al., "Intravaginal prasterone (DHEA) provides local action without clinically significant changes in serum concentrations of estrogens or androgens," Journal of Steroid Biochemistry & Molecular Biology 138:359-367, Elsevier (2013).
Lacey, J.V. Jr., "The Whi Ten Year"S Later: An Epidemiologist"S View," The Journal of steroid biochemistry and molecular biology 142:12-15, Pergamon, England (2014).
Lahiani-Skiba, M., et al., "Solubility and Dissolution Rate of Progesterone-Cyclodextrin-Polymer Systems," Drug development and industrial pharmacy 32(9):1043-1058, Informa Healthcare, England (2006).

(56) References Cited

OTHER PUBLICATIONS

Lancaster, R.W., et al., "The Polymorphism of Progesterone: Stabilization of A "Disappearing" Polymorph by Co-Crystallization," Journal of pharmaceutical sciences 96(12):3419-3431, Wiley-Liss, United States (2007).

Land, Laura M., "The influence of water content of triglyceride oils on the solubility of steriods," Pharmaceutical Research 22(5):Springer Science+Business Media (2005).

Lanigan, R.S. and Yamarik, T.A., "Final Report on the Safety Assessment of Bht (1)," International Journal of Toxicology 21(2):19-94, Sage Publications, United States (2002).

Lapez-Belmonte, J., et al., "Comparative Uterine Effects on Ovariectomized Rats After Repeated Treatment with Different Vaginal Estrogen formulations," Maturitas 72(4):353-358, Elsevier/North Holland Biomedical Press, Ireland (2012).

Idder, Salima, et al., "Physicochemical properties of Progesterone," 1-26, American Chemical Society & U.S. National Library of Medicine (2014).

Leonetti, H.B., et al., "Topical Progesterone Cream Has an Antiproliferative Effect on Estrogen-Stimulated Endometrium," Fertility and sterility 79(1):221-222, Elsevier for the American Society for Reproductive Medicine, United States (2003).

Leonetti, H.B., et al., "Transdermal Progesterone Cream as an Alternative Progestin in Hormone therapy," Alternative Therapies in Health and Medicine 11(6):36-38, InnoVision Communications, United States (2005).

Lewis, J.G., et al., "Caution on the Use of Saliva Measurements to Monitor Absorption of Progesterone From Transdermal Creams in Postmenopausal Women," Maturitas 41(1):1-6, Elsevier/North Holland Biomedical Press, Ireland (2002).

Li, G.C., et al., "Solid-State Nmr Analysis of Steroidal Conformation of $17\hat{1}\pm$- and $17\hat{1}^2$-Estradiol in the Absence and Presence of Lipid Environment," Steroids 77(3):185-192, Elsevier, United States (2012).

Lobo, R.A., "foreword: Hormone Therapy Arms," The Journal of steroid biochemistry and molecular biology 142:3, Pergamon, England (2014).

Lucy., et al., "Gonadotropin-releasing hormone at estrus: luteinizing hormone, estradiol, and progesterone during the periestrual and postinsemination periods in dairy cattle," Bioi Reprod 35(2):300-11, (1986) Abstract Only.

Lvova, M.SH., et al., "Thermal Analysis in the Quality Control and Standardization of Some Drugs," Journal of Thermal Analysis 40:405-411, Wiley (1993).

Madishetti, S.K., et al., "Development of Domperidone Bilayered Matrix Type Transdermal Patches : Physicochemical , in Vitro and Ex Vivo Characterization," Journal of Faculty of Pharmacy 18(3):221-229, BioMed Central, England (2010).

Magness, R.R. and Ford, S.P., "Estrone, Estradiol-17 Beta and Progesterone Concentrations in Uterine Lymph and Systemic Blood Throughout the Porcine Estrous Cycle," Journal of animal science 57(2):449-455, American Society of Animal Science, United States (1983).

"Management of Symptomatic Vulvovaginal Atrophy: 2013 Position Statement of The North American Menopause Society," Menopause 20(9):888-902, Lippincott-Raven Publishers, United States (2013).

Mcguffy, Irena, "Softgel Technology as a Lipid-Based Delivery Tool for Bioavailability Enhancement," Catalent Pharma Solutions Somerset, NJ (2011).

"Merck Index, Estradiol, The Merck Index Online, Royal Society of Chemistry 2014," https://www.rsc.org/Merck-Index/monograph/mono1500003758/estradiol?q=unauthorize.

"Merck Index Online, Progesterone, Royal Society of Chemistry, accessed at https:I/www.rsc.org/Merck-IndeXImonograph/print/mono1500007889/progesterone?q=authorize, accessed on 2013 search Feb. 17, 2014,".

"Merck Index Online, Progesterone, Royal Society of Chemistry, accessed at https://www.rsc.org/Merck-Index/monograph/print/mono1500007889/progesterone?q=authorize, accessed at 2013, search Feb. 24, 2014 ,".

Mesley, R.J., "Clathrate formation From Steroids," Chemistry & industry 37:1594-1595, John Wiley & Sons Ltd., England (1965).

Miao, Wenbin, et al., Chemical Properties of Progesterone American Chemical Society & U.S. National Library of Medicine (2014).

Miles, R.A., et al., "Pharmacokinetics and Endometrial Tissue Levels of Progesterone After Administration by intramuscular and Vaginal Routes : A Comparative Study," Fertility and Sterility 62(3):485-490, Elsevier for the American Society for Reproductive Medicine, United States (1994).

Miller, J.A., et al., "Safety and Feasibility of Topical Application of Limonene as a Massage Oil to the Breast," Journal of Cancer Therapy 3(5A), Scientific Research Publishing, United States (2012).

Mueck, A.O., et al., "Genomic and Non-Genomic Actions of Progestogens in the Breast," The Journal of steroid biochemistry and molecular biology 142:62-67, Pergamon, England (2014).

Muramatsu, Mitsuo, "Thermodynamic Relationship between a- and B-Forms of Crystalline Progesterone," Journal of Pharmaceutical Sciences 68(2):175-178, American Pharmacists Association (1979).

Ng, Jo-Han., et al., "Advances in biodiesel fuel for application in compression ignition engines," Clean Technologies and Environmental Policy 12:459-493, Springer-Verlag (2010).

Nicklas, M., et al., "Preparation and Characterization of Marine Sponge Collagen Nanoparticles and Employment for the Transdermal Delivery of 17Beta-Estradiol-Hemihydrate," Drug development and industrial pharmacy 35(9):1035-1042, Informa Healthcare, England (2009).

Nilsson, U., et al., "Analysis of Contact Allergenic Compounds in Oxidized d-Limonene," Chromatographia 42:199-205, (1996).

Non Final Office Action dated Dec. 12, 2011 for U.S. Appl. No. 12/561,515, filed Sep. 17, 2009.

Non-Final Office Action dated Feb. 18, 2014 for U.S. Appl. No. 14/099,545, filed Dec. 6, 2013.

Non-Final Office Action dated Mar. 20, 2013 for U.S. Appl. No. 13/684,002, filed Nov. 21, 2012.

Notelovitz, M., et al., "initial 17Beta-Estradiol Dose for Treating Vasomotor Symptoms," Obstetrics and Gynecology 95(5):726-731, Lippincott Williams & Wilkins, United States (2000).

Notice of Allowance dated Dec. 6, 2013 for U.S. Appl. No. 3/684,002, filed Nov. 21, 2012.

Panay, N., et al., "The 2013 British Menopause Society & Women's Health Concern recommendations on hormone replacement therapy," Menopause International: The Integrated Journal of Postreproductive Health, published online May 23, 2013, Sage Publications. http://min.sagepub.com/content/early/2013/05/23/1754045313489645. 1.

Panchagnula, R. and Ritschel, W.A., "Development and Evaluation of an intracutaneous Depot formulation of Corticosteroids Using Transcutol as a Cosolvent: in-Vitro, Ex-Vivo and in-Vivo Rat Studies," The Journal of pharmacy and pharmacology 43(9):609-614, Wiley, England (1991).

Parasuraman, S., et al., "Blood Sample Collection in Small Laboratory Animals," Journal of Pharmacology Pharmacotherapeutics 1(2):87-93, Medknow Publications and Media, India (2010).

Park, J.S., et al., "Solvent Effects on Physicochemical Behavior of Estradiols Recrystallized for Transdermal Delivery," Archives of pharmacal research 31(1):111-116, Pharmaceutical Society of Korea., Korea (South) (2008).

Park, J.S., et al., "Use of Cp/Mas Solid-State Nmr for the Characterization of Solvate Molecules within Estradiol Crystal forms," European journal of pharmaceutics and biopharmaceutics 60(3):407-412, Elsevier Science, Netherlands (2005).

Parrish, D.A. and Pinkerton, A.A., "A New Estra-1,3,5(10)-Triene-3,17Beta-Diol Solvate: Estradiol-Methanol-Water (3/2/1)," Acta crystallographica. Section C, Crystal structure communications 59(Pt2):o80-82, Wiley-Blackwell, United States (2003).

Patel., et al., "Transdermal Drug Delivery System: A Review," The Pharma Innovation, The Pharma Journal 1(4), (2012).

Payne, R.S., et al., "Examples of Successful Crystal Structure Prediction: Polymorphs of Primidone and Progesterone," Interna-

(56) References Cited

OTHER PUBLICATIONS tional Journal of Pharmaceutics 177(2):231-245, Elsevier/North-Holland Biomedical Press., Netherlands (1999).
PCCA, Apothogram, PCCA, Houston, TX, (2014).
Persson, Linda C, et al., "Physicochemical Properties of Progesterone Selecte," 1-5, American Chemical Society & U.S. National Library of Medicine (2014).
Pfaus, J.G., et al., "Selective Facilitation of Sexual Solicitation in the Female Rat by a Melanocortin Receptor Agonist," Proceedings of the National Academy of Sciences of the United States of America 101(27):10201-10204, National Academy of Sciences, United States (2004).
Pheasant, Richard, "Polymorphism of 17-Ethinylestradiol," Schering Corporation, Bloomfield, NJ (1950).
Pickles, V.R. "Cutaneous Reactions to injection of Progesterone Solutions into the Skin," British Medical Journal 2(4780):373-374, British Medical Association, England (1952).
Pinkerton, J.V. and Thomas, S., "Use of Serms for Treatment in Postmenopausal Women," The Journal of Steroid Biochemistry and Molecular Biology 142:142-154, Pergamon, England (2014).
Pinkerton, J.V. "What are the Concerns About Custom-Compounded "Bioidentical" Hormone therapy?," Menopause 21(12):1298-1300, Lippincott-Raven Publishers, United States (2014).
Pisegna, Gisia L, "A High-pressure Vibrational Spectroscopic Study of Polymorphism in Steroids," Thesis, McGill University, Dept. of Chem:National Library of Canada (1999).
Prajapati, Hetal N., et al., "A comparative Evaluation of Mono-, Di- and Triglyceride of Medium Chain Fatty Acids by Lipid/Suffactan UWater," Springerlink.com, pp. 1-21, (2011).
Prausnitz, M.R. and Langer, R., "Transdermal Drug Delivery," Nature Biotechnology 26(11):1261-1268, Nature America Publishing, United States (2008).
Price, S.L., "The Computational Prediction of Pharmaceutical Crystal Structures and Polymorphism," Advanced drug delivery reviews 56(3):301-319, Elsevier Science Publishers, B.V., Netherlands (2004).
Product Safety Assessment, Diethylene Glycol Monoethyl Ether, The Dow Chemical Company Page, 5 Pages (2007).
Progynova TS 100, available online at file:l//C:!Users/Caii%20Family/Desktop/Progynova%20TS%20100%2012%20Patches_Pack%20%28Estradioi%20Hemihydrate%29.html, 2010.
Provider Data Sheet, "About Dried Blood Spot Testing," ZRT Laboratory, 3 pages (2014).
Rahn, D.D., et al., "Vaginal Estrogen for Genitourinary Syndrome of Menopause: A Systematic Review," Obstetrics and Gynecology 124(6):1147-1156, Lippincott Williams & Wilkins, United States (2014).
Reisman, S.A., et al., "Topical Application of the Synthetic Triterpenoid Rta 408 Protects Mice From Radiation-induced Dermatitis," Radiation Research 181(5):512-520, Radiation Research Society, United States (2014).
Restriction/Election Requirement dated Mar. 5, 2014 for U.S. Appl. No. 14/099,623, filed Dec. 6, 2013.
Restriction/Election Requirement dated Feb. 20, 2014 for U.S. Appl. No. 14/099,562, filed Dec. 6, 2013.
Rosilio, V., et al., "Physical Aging of Progesterone-Loaded Poly(D,L,-Lactide-Co-Glycolide) Microspheres," Pharmaceutical research 15(5):794-798, Kluwer Academic/Plenum Publishers, United States (1998).
Ross, D., et al., "Randomized , Double-Blind , Dose-Ranging Study of the Endometrial Effects of a Vaginal Progesterone Gel in Estrogen-Treated Postmenopausal Women," American Journal of Obstetrics and Gynecology 177(4):937-941, Elsevier, United States (1997).
Ruan, X. and Mueck, A.O., "Systemic Progesterone therapy—Oral, Vaginal , injections and Even Transdermal ?," Maturitas 79(3):248-255, Elsevier/North Holland Biomedical Press, Ireland (2014).
Salem, H.F. "Sustained-Release Progesterone Nanosuspension Following intramuscular injection in Ovariectomized Rats," International Journal of Nanomedicine 10:943-954,DOVE Medical Press, New Zealand (2010).

Salole, E.G., "The Physicochemical Properties of Oestradiol," Journal of Pharmaceutical and Biomedical Analysis 5(7):635-648, Elsevier Science, England (1987).
Salole, Eugene G., "Estradiol, Analyl ical Profiles of Drug Substances," vol. 15, pp. 283-318, (1986).
Santen, R.J., "Menopausal Hormone Therapy and Breast Cancer," The Journal of Steroid Biochemistry and Molecular Biology 142:52-61, Pergamon, England (2014).
Santen, R.J. "Vaginal Administration of Estradiol : Effects of Dose , Preparation and Timing on Plasma Estradiol Levels," The Journal of the International Menopause Society :1-14, Informa Healthcare, England (2014).
Sarkar, Basu, et al., "Chemical Stability of Progesterone in Compounded Topical Preparations using PLO Transdermal CreamTM and HRT CreamTM Base," Steroids and Hormonal Science 4:2, (2013).
Sarrel. and Philip., "The Mortality Toll of Estrogen Avoidance: An Analysis of Excess Deaths Among Hysterectomized Women Aged 50 to 59 Years," American Journal of Public Health, Research and Practice, pp. e1-e6, Published online ahead of print Jul. 18, 2013.
Satyanarayana, D, et al., "Aqueous Solubility Predictions of Aliphatic Alcohols, Alkyl Substituted Benzoates and Steroids," Asian Journal of Chemistry 9(3): 418-26, (1997).
Scavarelli, Rosa Maria, et al., Progesterone and Hydrate or Solvate, SciFinder, pp. 1-2, American Chemical Society (2014).
Schindler, A.E., "The "Newer" Progestogens and Postmenopausal Hormone Therapy (Hrt)," The Journal of Steroid Biochemistry and Molecular Biology 142:48-51, Pergamon, England (2014).
Schutte, S.C. and Taylor, R.N., "A Tissue-Engineered Human Endometrial Stroma That Responds to Cues for Secretory Differentiation , Decidualization , and Menstruation," Fertility and Sterility 97(4):997-1003, Elsevier for the American Society for Reproductive Medicine, United States (2012).
Schweikart, K.M., et al., "Comparative Uterotrophic Effects of Endoxifen and Tamoxifen in Ovariectomized Sprague-Dawley Rats," Toxicologic Pathology 42(8):1188-1196, Sage Publications, United States (2014).
SciFinder Scholar Prednisone Chemical Properties, SciFinde, pp. 1-7, National Library of Medicine (2014).
SciFinder Scholar Prednisone Physical Properties, SciFinder, pp. 1-10, Natioinal Library of Medicine (2014).
SciFinder Scholar Progesterone Experimental Properties, SciFinder, pp. 1-9, American Chemical Society (2014).
Serantoni, Foresti, et al., "4-Pregnen-3, 20-Dione (progesterone, form II)," Crystal Structure Communications 4(1):189-92, CAPLUS Database (1975).
Shao, R., et al., "Direct Effects of Metformin in the Endometrium : A Hypothetical Mechanism for the Treatment of Women with Pcos and Endometrial Carcinoma," Journal of Experimental & Clinical Cancer Research 33:41, BioMed Central, England (2014).
Sharma, H.C., et al., "Physical Properties of Progesterone Selected Refer, SciFinder," pp. 1-5, American Chemical Society & U.S. National Library of Medicine (2014).
Shrier, L.A., et al., "Mucosal Immunity of the Adolescent Female Genital Tract," The Journal of Adolescent Health 32(3):183-186, Elsevier, United States (2003).
Shufelt, C.L., et al., "Hormone Therapy Dose , formulation , Route of Delivery , and Risk of Cardiovascular Events in Women : Findings From the Women"S Health initiative Observational Study," Menopause 21(3):260-266, Lippincott-Raven Publishers, United States (2014).
Siew, A, et al.,"Bioavailability Enhancement with Lipid-Based Durg-Delivery Systems" Phamraceutical Technology 28,30-31, (2014).
Sigma-Aldrich, Progesterone-Water Soluble: powder, BioReagent, suitable for cell culture), MSDS available online: http://www.sigmaaldrich.com/catalog/producl/sigma/p7556.
Simon, J., et al., "Effective Treatment of Vaginal Atrophy with an Ultra-Low-Dose Estradiol Vaginal Tablet," Obstetrics and gynecology 112(5):1053-1060, Lippincott Williams & Wilkins, United States (2008).
Simon, J.A. "What If the Women'S Health initiative Had Used Transdermal Estradiol and Oral Progesterone instead?," Menopause 21(7):769-783, Lippincott-Raven Publishers, United States (2014).

(56) References Cited

OTHER PUBLICATIONS

Sitruk-Ware. and Regine., "Oral Micronized Progesterone—Bioavailability Pharmacokinetics, Pharmacological and Therapeutic Implications—A Review," Contraception 36(4):373-402, (1987).
Sitruk-Ware, R., "Progestogens in Hormonal Replacement Therapy: New Molecules, Risks, and Benefits," Menopause 9(1):6-15, Lippincott-Raven Publishers, United States (2002).
Smith and Nicholas., "Lower Risk of Cardiovascular Events in Postmenopausal Women Taking Oral Estradiol Compared with Oral Conjugated Equine Estrogens," JAMA Intern Med, pp. e1-e7, published online Sep. 30, 2013.
Smyth, H.F., et al., "A 2-Yr Study of Diethylene Glycol Monoethyl Ether in Rats," Food and Cosmetics Toxicology 2:641-642, Pergamon Press, England (1964).
Stanczyk, F.Z. and Bhavnani, B.R., "Current Views of Hormone Therapy for the Management and Treatment of Postmenopausal Women," The Journal of steroid biochemistry and molecular biology 142:1-2, Pergamon, England (2014).
Stanczyk, F.Z. and Bhavnani, B.R., "Use of Medroxyprogesterone Acetate for Hormone Therapy in Postmenopausal Women: Is It Safe?," The Journal of steroid biochemistry and molecular biology 142:30-38, Pergamon, England (2014).
Stanczyk, F.Z., et al., "Ethinyl Estradiol and $17\tilde{1}^2$-Estradiol in Combined Oral Contraceptives: Pharmacokinetics, Pharmacodynamics and Risk assessment," Contraception 87(6):706-727, Elsevier, United States (2013).
Stanczyk, F.Z., et al., "therapeutically Equivalent Pharmacokinetic Profile Across Three Application Sites for Ag200-15 , A Novel Low-Estrogen Dose Contraceptive Patch," Contraception 87(6):744-749, Elsevier, United States (2013).
Stein, Emily A., et al., "Progesterone, SciFinder Scholar Search" 1-46, American Chemical Society & U.S. National Library of Medicine, Feb. 24, 2014.
Stein, Emily A., et al., "Progesterone Physical Properties," 1-46, American Chemical Society & U.S. National Library of Medicine, Feb. 24, 2014.
Stein, Emily A., et al., "Progesterone Physical Properties," 1-46, American Chemical Society & U.S. National Library of Medicine, Mar. 3, 2014.
Strickley, R.G., "Solubilizing Excipients in Oral and injectable formulations," Pharmaceutical research 21(2):201-230, Kluwer Academic/Plenum Publishers, United States (2004).
Strocchi, Antonino, Fatty Acid Composition, and Triglyceride Structure of Corn Oil, Hydrogenated Corn Oil, and Corn Oil Margarine, Journal of Food Science 47, pp. 36-39, (1981).
Struhar, M., et al., "Preparation of the Estradiol Benzoate injection Suspension," Ceskoslovenska farmacie 27(6):245-249, Ceskoslovenska Lekarska Spolecnost, Czech Republic (1978).
Sullivan, D.W.JR., et al., "A review of the nonclinical safety of Transcutol®, a highly purified form of diethylene glycol monoethyl ether (DEGEE) used as a pharmaceutical excipient," Food and Chemical Toxicology 72:40-50, Elsevier Science Ltd, England (2014).
Sun, J. "D-Limonene : Safety and Clinical Applications," Alternative Medicine Review 12(3):259-264, Alternative Medicine Review, United States (2007).
Tahition Noni. "Body Balance Cream," http://products.lni.com/dominican_republic/sa_spanish/nonistore/ producl/3438/3416/, 1 page, undated.
Tait, A.D., "Characterization of the Products From the Oxidation of Progesterone with Osmium Tetroxide," Steroids 20(5):531-542, Elsevier, United States (1972).
Takacs, M., et al., "The Light Sensitivity of Corticosteroids in Crystalline form Photochemical Studies 59 (1)," Pharmaceutica acta Helvetiae 66(5-6):137-140, Schweizerische Apotheker-Verein, Switzerland (1991).
Tan, Melvin, S., et al., "A Sensitive Method for the Determination of Progesterone in Human Plasma by LC-MS-MS, M1025," Cedra Corporation, Austin.
Tang, F.Y., et al., "Effect of Estrogen and Progesterone on the Development of Endometrial Hyperplasia in the Fischer Rat," Biology of Reproduction 31(2):399-413, Society for the Study of Reproduction, United States (1984).
Tas, M., et al., "Comparison of Antiproliferative Effects of Metformine and Progesterone on Estrogen-induced Endometrial Hyperplasia in Rats," Gynecological Endocrinology 29(4):311-314, Informa Healthcare, England (2013).
Tella, S.H., Gallagher, J.C., "Prevention and treatment of postmenopausal osteoporosis," The Journal of Steroid Biochemistry and Molecular Biology 142:155-170, Elsevier Ltd., United Kingdom (2014).
Thomas, J., et al., "The Effect of Water Solubility of Solutes on Their Flux Through Human Skin in Vitro: An Extended Flynn Database Fitted to the Roberts-Sloan Equation," International Journal of Pharmaceutics 339(1-2):157-167, Elsevier/North-Holland Biomedical Press., Netherlands (2007).
Thomas, P. "Characteristics of Membrane Progestin Receptor Alpha (Mpralpha) and Progesterone Membrane Receptor Component 1 (Pgmrc1) and their Roles in Mediating Rapid Progestin Actions," Frontiers in Neuroendocrinology 29(2):292-312, Academic Press, United States (2008).
Tripathi, R., et al., "Study of Polymorphs of Progesterone by Novel Melt Sonocrystallization Technique: A Technical Note," AAPS PharmSciTech 11(3):1493-1498, Elsevier/North-Holland Biomedical Press., Netherlands (2010).
Trommer, H. and Neubert, R.H., "Overcoming the Stratum Corneum : the Modulation of Skin Penetration A Review," Skin Pharmacology and Physiology 19(2):106-121, Karger, Switzerland (2006).
Ueda, T., et al., "Topical and Transdermal Drug Products," Pharmacopeial Forum 35(3):750-764, (2009).
USP, 401 Fats and Fixed Oils, Chemical Tests, Second Suplementto USP36-NF 31, pp. 6141-6151, (2013).
USP, Lauroyl Polyoxylglycerides, Saftey Data Sheet, US, 5611 Version #02, pp. 1-9, (2013).
"USP Monographs: Progesterone. USP29, accessed at www.pharmacopeia.cn/v29240/usp29nf24sO_m69870.html, accessed on Feb. 25, 2014,".
USP, Official Monographs, Corn Oil, NF 31, pp. 1970-1971, (2013).
USP. Official Monographs, Lauroyl Polyoxylglycerides, NF 31, pp. 2064-2066, (2013).
USP, Official Monographs, Medium Chain Triglycerides, NF 31, pp. 2271-2272, (2013).
USP, Official Monographs, Mono- and Di-glycerides, NF 31, pp. 2101, (2013).
USP, USP Certificate-Corn Oil, Lot GOL404, Jul. 2013.
Utian, W.H., et al., "Relief of Vasomotor Symptoms and Vaginal Atrophy with Lower Doses of Conjugated Equine Estrogens and Medroxyprogesterone Acetate," Fertility and sterility 75(6):1065-1079, Elsevier for the American Society for Reproductive Medicine, United States (2001).
Voegtline, K.M. and Granger, D.A., "Dispatches From the interface of Salivary Bioscience and Neonatal Research," Frontiers in Endocrinology 5:25,Frontiers Research Foundation, Switzerland (2014).
Waddell, B.J. and Bruce, N.W., "The Metabolic Clearance of Progesterone in the Pregnant Rat : Absence of a Physiological Role for the Lung," Biology of Reproduction 40(6):1188-1193, Society for the Study of Reproduction, United States (1989).
Waddell, B.J. and Oleary, P.C., "Distribution and Metabolism of Topically Applied Progesterone in a Rat Model," The Journal of Steroid Biochemistry and Molecular Biology 80(4-5):449-455, Pergamon, England (2002).
Walter, L.M., et al., "The Role of Progesterone in Endometrial Angiogenesis in Pregnant and Ovariectomised Mice," Reproduction 129(6):765-777,Reproduction and Fertility by BioScientifica, England (2005).
Cole, W. and Julian, P.L., "A Study of the 22-Ketosteroids," Journal of the American Chemical Society 67(8):1369-1375, (1945).
Weber, E.J. "Corn Lipids," Cereal Chemistry Journal 55(5): 572-584, American Association of Cereal Chemists (1978).

(56) References Cited

OTHER PUBLICATIONS

Weber, M.T., et al., "Cognition and Mood in Perimenopause: A Systematic Review and Meta-Analysis," The Journal of Steroid Biochemistry and Molecular Biology 142:90-98, Pergamon, England (2014).

Whitehead, M.I., et al., "Absorption and Metabolism of Oral Progesterone," British medical journal 280(6217):825-827, British Medical Association, England (1980).

Duax, W.L., et al., "Conformation of Progesterone Side Chain: Conflict between X-ray Data and Force-Field Calculations," Journal of the American Chemical Society 103(22):6705-6712, (1981).

Wiranidchapong, Chutima et al., "Method of preparation does not affect the miscibility between steroid hormone and polymethacrylate," Thermochimica Acta 485(1-2):57-64, Elsevier B.V., Netherlands (2009).

Wood, C.E., et al., "Effects of estradiol with micronized progesterone or medroxyprogesterone acetate on risk markers for breast cancer in postmenopausal monkeys," Breast Cancer Research and Treatment 101:125-134, Springer Science+ Business Media B.V (2006), published online Jul. 14, 2006.

Wren, B.G., et al., "Effect of Sequential Transdermal Progesterone Cream on Endometrium , Bleeding Pattern , and Plasma Progesterone and Salivary Progesterone Levels in Postmenopausal Women," The Journal of the International Menopause Society 3(3):155-160, Informa Healthcare, England (2000).

Wu, X., et al., "Gene Expression Profiling of the Effects of Castration and Estrogen Treatment in the Rat Uterus," Biology of Reproduction 69(4):1308-1317, Society for the Study of Reproduction, United States (2003).

Yalkowsky, Samuel, H. , "Handbook of Acqueous Solubility Data," 1110-1111, CRC Press, United States .

Yalkowsky, S.H. and Valvani, S.C., "Solubility and Partitioning I: Solubility of Nonelectrolytes in Water," Journal of Pharmaceutical Sciences 69(8):912-922, Wiley-Liss, United States (1980).

Yue, W., et al., "Genotoxic Metabolites of Estradiol in Breast: Potential Mechanism of Estradiol induced Carcinogenesis," The Journal of Steroid Biochemistry and Molecular Biology 86(3-5):477-486, Pergamon, England (2003).

Zava, D. "Topical Progesterone Delivery and Levels in Serum, Saliva, Capillary Blood, and Tissues" Script:4-5.

Zava, D.T., et al., "Percutaneous absorption of progesterone," Maturitas 77:91-92, Elsevier/North Holland Biomedical Press, Ireland (2014).

Geelen, M.J.H., et al., "Dietary Medium-Chain Fatty Acids Raise and (n-3) Polyunsaturated Fatty Acids Lower Hepatic Triacylglycerol Synthesis in Rats," The Journal of Nutrition 125:2449-2456, American Institute of Nutrition, United States (1995).

Herman, A and Herman, A.P., "Essential oils and their constituents as skin penetration enhancer for transdermal drug delivery: A review," Journal of Pharmacy and Pharmacology 67(4):473-485, Royal Pharmaceutical Society, England (2014).

Manson, J.E., et al., "Menopausal Hormone Therapy and Health Outcomes During the Intervention and Extended Poststopping Phases of the Women's Health Initiative Randomized Trials," The Journal of the American Medical Association 310:1353-1368, American Medical Association, United States (2013).

Notice of Allowance, dated Dec. 10, 2014, in U.S. Appl. No. 14/099,562, Bernick, B.A., filed Dec. 6, 2013, 10 pages.

Notice of Allowance, dated Dec. 10, 2014, in U.S. Appl. No. 14/099,598, Bernick, B.A., filed Dec. 6, 2013, 8 pages.

Notice of Allowance, dated Dec. 15, 2014, in Un U.S. Appl. No. 14/099,623, Bernick, B.A., filed Dec. 6, 2013, 9 pages.

Notice of Allowance, dated Feb. 11, 2015, in U.S. Appl. No. 14/475,864, Bernick, B.A., filed Sep. 3, 2014, 9 pages.

Notice of Allowance, dated Feb. 13, 2015, in U.S. Appl. No. 14/475,814, Bernick, B.A., filed Sep. 3, 2014, 6 pages.

Notice of Allowance, dated Jan. 22, 2015, in U.S. Appl. No. 14/099,582, Bernick, B.A., filed Dec. 6, 2013, 5 pages.

Notice of Allowance, dated Jul. 14, 2014, in U.S. Appl. No. 14/099,545, Bernick, B.A., filed Dec. 6, 2013, 9 pages.

Notice of Allowance, dated Jul. 15, 2014, in U.S. Appl. No. 14/099,571, Bernick, B.A., filed Dec. 6, 2013, 11 pages.

Notice of Allowance, dated Nov. 26, 2014, in U.S. Appl. No. 14/099,612, Bernick, B.A., filed Dec. 6, 2013, 12 pages.

Notice of Allowance, dated Nov. 7, 2014, in U.S. Appl. No. 14/099,582, filed Dec. 6, 2013, 14 pages.

Office Action, dated Apr. 14, 2015, in U.S. Appl. No. 14/125,554, Bernick, B.A., filed Dec. 12, 2013, 9 pages.

Office Action, dated Apr. 7, 2015, in U.S. Appl. No. 14/624,051, Bernick B.A., filed Feb. 17, 2015, 10 pages.

Office Action, dated Dec. 8, 2014, in U.S. Appl. No. 14/106,655, Bernick, B.A., filed Dec. 13, 2013, 9 pages.

Office Action, dated Feb. 18, 2015, in U.S. Appl. No. 14/521,230, Bernick, B.A., filed Oct. 22, 2014, 8 pages.

Office Action, dated Jul. 18, 2014, in U.S. Appl. No. 14/099,623, Bernick, B.A., filed Dec. 6, 2013, 12 pages.

Office Action, dated Jul. 2, 2014, in U.S. Appl. No. 14/099,562, Bernick, B.A., filed Dec. 6, 2013, 9 pages.

Office Action, dated Jul. 3, 2014, in U.S. Appl. No. 14/099,598, Bernick, B.A., filed Dec. 6, 2013, 16 pages.

Office Action, dated Jul. 30, 2014, in U.S. Appl. No. 14/099,612, Bernick, B.A. filed Dec. 6, 2013, 12 pages.

Office Action, dated Jun. 17, 2014, in U.S. Appl. No. 14/099,582, Bernick, B.A. filed Dec. 6, 2013, 14 pages.

Office Action, dated Mar. 12, 2015, in U.S. Appl. No. 14/136,048, Bernick, B.A. filed Dec. 20, 2013, 24 pages.

Office Action, dated Mar. 27, 2014, in U.S. Appl. No. 14/099,562, Bernick, B.A. filed Dec. 6, 2013, 8 pages.

Office Action, dated Oct. 1, 2014, in U.S. Appl. No. 14/475,814, Bernick, B.A. filed Sep. 3, 2014, 6 pages.

Office Action, dated Oct. 2, 2014, in U.S. Appl. No. 14/475,864, Bernick, B.A., filed Sep. 3, 2014, 6 pages.

Portman, D., et al., "One-year treatment persistence with local estrogen therapy in postmenopausal women diagnosed as having vaginal atrophy," Menopause 22(11): 7 pages, The North American Menopause Society, United States (2015).

Rao, R. and Rao, S., "Intra Subject Variability of Progesterone 200 mg Soft Capsules in Indian Healthy Adult Postmenopausal Female Subjects under Fasting Conditions," Journal of Bioequivalence & Bioavailability 6(4):139-143, Open Access (2014).

Restriction Requirement, dated Apr. 14, 2015, in U.S. Appl. No. 13/843,428, Bernick, B.A., filed Mar. 15, 2013, 7 pages.

Restriction Requirement, dated Apr. 29, 2014, in U.S. Appl. No. 14/099,582, Bernick, B.A., filed Dec. 6, 2013, 9 pages.

Restriction Requirement, dated Dec. 5, 2014, in U.S. Appl. No. 14/125,554, Bernick, B.A., filed Dec. 12, 2013, 7 pages.

Restriction Requirement, dated Dec. 5, 2014, in U.S. Appl. No. 14/521,230, Bernick, B.A., filed Oct. 22, 2014, 9 pages.

Restriction Requirement, dated Jul. 3, 2014, in U.S. Appl. No. 14/106,655, Bernick, B.A., filed Dec. 13, 2013, 6 pages.

Restriction Requirement, dated Mar. 16, 2015, in U.S. Appl. No. 13/843,362, Bernick, B.A., filed Mar. 15, 2013, 7 pages.

Restriction Requirement, dated Mar. 20, 2014, in U.S. Appl. No. 14/099,612, Bernick, B.A., filed Dec. 6, 2013, 9 pages.

Restriction Requirement, dated Mar. 26, 2015, in U.S. Appl. No. 14/476,040, Bernick, B.A., filed Sep. 3, 2014, 7 pages.

Restriction Requirement, dated Mar. 28, 2014, in U.S. Appl. No. 14/099,571, Bernick, B.A., filed Dec. 6, 2013, 7 pages.

International Search Report and Written Opinion of International Application No. PCT/US2015/023041, Korean Intellectual Property Office, Republic of Korea, dated Jun. 30, 2015, 14 pages.

Sarpal, K., et al., "Self-Emulsifying Drug Delivery Systems: A Strategy to Improve Oral Bioavailability," *Current Research & Information on Pharmaceuticals Sciences* 11(3):42-49, NIPER, India (Jul.-Sep. 2010).

Rajeswara, Rao P., et al., "The Affect of Capmul, Labrafil and Transcutol on Progesterone 100 Mg Soft Capsules Bioavailability in Indian Healthy Adult Postmenopausal Female Subjects Under Fasting Conditions," Bioequivalence & Bioavailability: vol. 7(2): pp. 95-107 (2015).

Regidor, P.A., "Progesterone in Peri- and Postmenopause: A Review," *Geburtshilfe Frauenheilkd*, Nov. 2014 74 (11): 995-1002; 17 pages.

(56) References Cited

OTHER PUBLICATIONS

Notice of Allowance dated Sep. 11, 2013 for U.S. Appl. No. 12/561,515, filed Sep. 17, 2009.
NuGen, "What is NuGen HP Hair Growth System? ," http://www.skinenergizer.com/Nugen-HP-Hair-Grow1h-System-p/ senusystem.htm, 3 pages, undated.
NuGest 900™, http://www.lhehormoneshop.nel/nugest900.htm, 4 pages, undated.
O'Leary, P., et al., "Salivary, but Not Serum or Urinary Levels of Progesterone are Elevated After Topical Application of Progesterone Cream to Pre-and Postmenopausal Women," Clinical Endocrinology 53(5):615-620,Blackwell Scientific Publications, England (2000).
"Open Notebook, Science Solubility Challenge, Solubility of progesterone in organic solvents, accessed at http://lxsrv7.oru.edu/-alang/onsc/solubility/allsolvents.php?solute=progesterone, accessed on Jul. 16, 2013".
Opinion on Diethylene glycol monoethyl ether, Scientific Committee on Consumer Products, The SCCP adopted this opinion at its 10th plenary,27 pages (2006).
Outterson, K. "The Drug Quality and Security Act—Mind the Gaps," The New England Journal of Medicine 370(2):97-99,Massachusetts Medical Society., United States (2014).
Panay, N., et al., "The 2013 British Menopause Society & Women's Health Concern recommendations on hormone replacement therapy," DOI: 0.1177/1754045313489645, min.sagepub.com. Menopause International: The Integrated Journal of Post reproductive Health 0(0):1-10, (2013).
Panay, N., et al., "The 2013 British Menopause Society & Women's Health Concern Recommendations on Hormone Replacement Therapy," Menopause international 19(2):59-68, Sage, England (2013).

* cited by examiner

Mean ± SEM; n=8
* p=0.02 vs. Neg Control

Mean ± SD; n=8
* p=0.02 vs. Neg Control

FORMULATIONS FOR SOLUBILIZING HORMONES

CROSS-REFERENCES TO RELATED APPLICATIONS

This application claims priority to U.S. Provisional Pat. Appl. No. 62/196,021, filed Jul. 23, 2015, the entirety of which is incorporated herein by reference.

FIELD

This disclosure relates to the field of steroid hormones. Specifically, this disclosure provides compositions for improving the solubility of steroid hormones.

BACKGROUND

Steroid hormones, synthesized and secreted into the bloodstream by endocrine glands, are vital constituents for the proper functioning of the human body. Steroid hormones can be classified into five groups based on the receptors to which they bind, namely: glucocorticoids, mineralocorticoids, androgens, estrogens, and progestogens. It is known that steroid hormones aid in regulating metabolism, regulating water and salt function, regulating immune function, controlling inflammation, and developing sexual characteristics. Steroid hormones such as progesterone and estradiol have poor bioavailability and efficacy as these hormones are less soluble in water. Thus, these hormones need to be administered in a high dose, which can result in increased health risks.

Progesterone is a naturally occurring C-21 steroid hormone belonging to the progestogen class. It is produced by the ovaries (more precisely by the cells of the corpus luteum) during the post-ovulatory luteal phase and to a lesser degree by the adrenal glands and the placenta during the second part of pregnancy. In women, progesterone levels are relatively low during the pre-ovulatory phase of the menstrual cycle, rise after ovulation, and are elevated during the luteal phase. Progesterone is commonly referred to as the "hormone of pregnancy" as it plays an important role in fetal development. Insufficient secretion of progesterone in women can cause biological effects such as progestative effect, anti-androgen effect, and anti-estrogen effect. Further, progesterone insufficiency can lead to premenstrual syndromes and menstrual irregularities.

Progesterone and its analogues are used to support pregnancy in Assisted Reproductive Technology (ART) cycles, to control persistent ovulatory bleeding, to prepare the uterine lining in infertility therapy, and to support early pregnancy. Further, progesterone can be used for regularizing menstruation. Vaginally dosed progesterone is also being investigated for a potentially beneficial treatment in preventing preterm birth in women who are at the risk of preterm birth.

Progesterone does not dissolve in water and is poorly absorbed resulting in both intra- and inter-patient variability when orally administered. To overcome the drawbacks of poor bioavailability associated with natural progesterone, researchers have used various synthetic progesterone derivatives such as medroxyprogesterone, norethisterone, methylestrenolone, chlormadinone acetate, 6-dehydroretroprogesterone, and lynestrenol. But use of these derivatives are associated with side-effects not associated with natural progesterone.

U.S. Pat. Nos. 4,196,188; 5,140,021; 7,431,941; 7,829,115; and U.S. Patent Application Publication No. 2011/0135719 are hereby incorporated by reference.

SUMMARY

This disclosure provides compositions comprising a solubilized steroid hormone and at least one terpene. In certain embodiments, the steroid hormone can be a progestogen, such as progesterone. In other embodiments, the steroid hormone can be estrogen. And in still further embodiments, the steroid hormone can be a combination of estrogen and progesterone. In certain embodiments, the terpene can be a monocyclic terpene such as limonene.

This disclosure also provides methods of treating, inhibiting, or preventing a condition or disorder characterized by a steroid hormone deficiency. The methods comprise administering to a subject a therapeutically effective amount of at least one composition disclosed herein.

In certain embodiments, this disclosure provides a liquid composition comprising progesterone, estradiol, or a combination thereof, and a terpene.

In certain embodiments, the terpene is d-limonene.

In certain embodiments, the composition comprises progesterone.

In certain embodiments, the composition comprises progesterone and the terpene is d-limonene.

In certain embodiments, the liquid composition is encapsulated in a soft gelatin capsule.

In certain embodiments, the liquid composition further comprises an antioxidant.

In certain embodiments, the antioxidant is selected from the group consisting of α-tocopherol acetate, acetone sodium bisulfite, acetylcysteine, ascorbic acid, ascorbyl palmitate, butylated hydroxyanisole (BHA), butylated hydroxytoluene (BHT), cysteine, cysteine hydrochloride, α-tocopherol, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, tocopherol, and combinations thereof.

This disclosure also provides a method of treating amenorrhea or endometrial hyperplasia in a patient in need thereof comprising administering to the patient an effective amount of the liquid composition described herein.

In certain embodiments, the administering comprises orally administering the composition, sublingually administering the composition, topically administering the composition, vaginally administering the composition, rectally administering the composition, or a combination thereof.

In certain embodiments the administering comprises orally administering the liquid composition, vaginally administering the liquid composition, rectally administering the liquid composition, or a combination thereof.

In certain embodiments of the method described herein, the liquid composition is encapsulated in a soft gelatin capsule.

In certain embodiments of the method described herein, the liquid composition further comprises an antioxidant.

In certain embodiments, the antioxidant is selected from the group consisting of α-tocopherol acetate, acetone sodium bisulfite, acetylcysteine, ascorbic acid, ascorbyl palmitate, butylated hydroxyanisole (BHA), butylated hydroxytoluene (BHT), cysteine, cysteine hydrochloride, α-tocopherol, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, tocopherol, and combinations thereof.

In certain embodiments of the method described herein, the liquid composition comprises from about 25 mg of progesterone to about 500 mg of progesterone.

In some embodiments of the method described herein, the liquid composition comprises about 25, about 50, about 75, about 100, about 125, about 150, about 175, about 200, about 225, about 250, about 275, about 300, about 325, about 350, about 375, about 400, about 425, about 450, about 475, or about 500 mg of progesterone.

In certain embodiments of the liquid composition described herein, the composition comprises at least about 80% w/w d-limonene.

In certain embodiments, the liquid composition further comprises an antioxidant.

BRIEF DESCRIPTION OF THE DRAWINGS/FIGURES

The foregoing summary, as well as the following detailed description, will be better understood when read in conjunction with the appended figures. For the purpose of illustration, the figures may describe the use of specific embodiments. It should be understood, however, that this disclosure is not limited to the prices embodiments discussed or described in these figures.

DETAILED DESCRIPTION

Definitions

Figure 1:
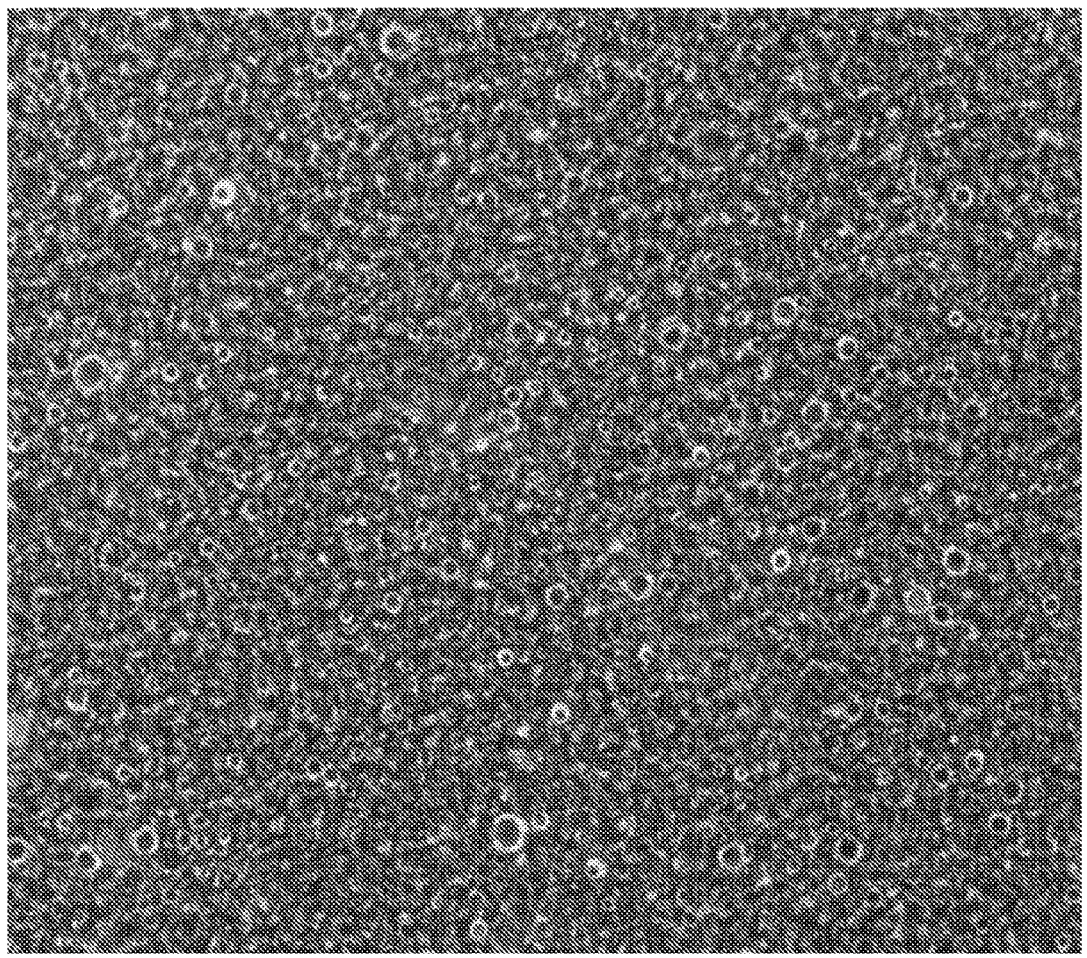
FIG. 1 shows Cream 1 as described herein viewed with a birefringence microscope using non-polarized light (10×40).

The singular forms "a," "an," and "the" include plural referents unless the context clearly dictates otherwise.

As used herein, the term "or" shall be understood to be defined as a logical disjunction (i.e., and/or) and shall not indicate an exclusive disjunction unless expressly indicated as such with the terms "either," "unless," "alternatively," and words of similar effect.

As used herein, the term "about" refers to ±5% of the specified value, unless otherwise specified.

As used herein, the terms "host," "subject," and "patient" refer to any animal, including humans.

The term "micronized" as used herein, refers to particles having an X50 particle size value below about 15 microns or having an X90 particle size value below about 25 microns. In some embodiments, a micronized particle can have an X90 particle size of less than 5 microns. The term "X50" means that one-half of the particles in a sample are smaller in diameter than a given number. For example, a micronized particle having an X50 of 5 microns means that, for a given sample of the micronized particle, one-half of the particles have a diameter of less than 5 microns. Similarly, the term "X90" means that ninety percent (90%) of the particles in a sample are smaller in diameter than a given number.

As used herein, the term "prevent" refers to the prophylactic treatment of a subject who is at risk of developing a condition (e.g., steroid hormone deficiency) resulting in a decrease in the probability that the subject will develop the condition.

The term "treat" as used herein refers to any type of treatment that imparts a benefit to a patient afflicted with a disorder, including, but not limited to, improving the patient's condition by reducing or inhibiting one or more symptoms of the disorder or delaying the progression of the disorder. In a particular embodiment, the treatment of a steroid hormone deficiency results in at least an increase in the level of the steroid hormone in the subject.

The phrase "therapeutically effective amount" refers to an amount of a composition or of a given steroid hormone suitable to treat a particular disorder or disease.

A "carrier" refers to, for example, a diluent, adjuvant, preservative (e.g., benzyl alcohol), antioxidant (e.g., ascorbic acid, sodium metabisulfite, etc.), solubilizer (e.g., polysorbate 80), emulsifier, buffer (e.g., Tris HCl, acetate, phosphate), water, aqueous solutions, oils, bulking substance (e.g., lactose, mannitol), cryo-/lyo-protectants, tonicity modifier, excipient, auxiliary agent or vehicle with which an active agent of the present invention can be administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

As used herein, the phrase "substantially pure" means that an identified component is at least about 90% pure by weight, in certain embodiments, at least about 95% pure by weight, and in still further embodiments, at least about 98% pure by weight.

As used herein, the phrase "steroid hormone" refers to endogenous female sex hormones including, but not limited to, progesterone, 17-hydroxyprogesterone, 5α-dihydroprogesterone, 11-deoxycorticosterone, estradiol, estriol, and estrone.

As used herein, the term "d-limonene" refers to (4R)-1-methyl-4-(1-methylethenyl)-cyclohexene (CAS No. 5989-27-5), which is also known by synonyms including (+)-4-isopropenyl-1-methylcyclohexe, (+)-p-mentha-1,8-diene, and (R)-(+)-Limonene.

The term "area under the curve" ("AUC") refers to the area under the curve defined by changes in the blood concentration of an active pharmaceutical ingredient (e.g., progesterone or estradiol), or a metabolite of the active pharmaceutical ingredient, over time following the administration of a dose of the active pharmaceutical ingredient. "$AUC_{0-\infty}$" is the area under the concentration-time curve extrapolated to infinity following the administration of a dose. "$AUC_{0-t}$" is the area under the concentration-time curve from time zero to time t following the administration of a dose, wherein t is the last time point with a measurable concentration.

The term "$C_{max}$" refers to the maximum value of blood concentration shown on the curve that represents changes in blood concentrations of an active pharmaceutical ingredient (e.g., progesterone or estradiol), or a metabolite of the active pharmaceutical ingredient, over time.

The term "$t_{max}$" refers to the earliest time at which the blood concentration of an active pharmaceutical ingredient (e.g., progesterone or estradiol), or a metabolite of the active pharmaceutical ingredient is at its maximum value.

The term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

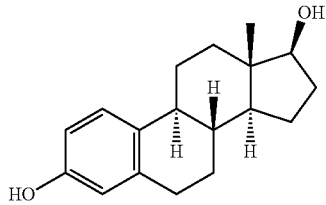

Estradiol is supplied in an anhydrous or hemi-hydrate form. For the purposes of this disclosure, the anhydrous form or the hemihydrate form can be substituted for the other by accounting for the water or lack of water according to well-known and understood techniques.

The term "progesterone" refers to pregn-4-ene-3,20-dione. Progesterone is also interchangeably called P4 and is found endogenously in the human body. As used herein, progesterone refers to the bio-identical or body-identical form of progesterone found in the human body and having the structure:

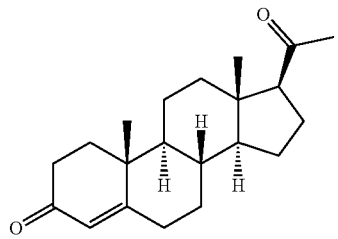

The term "medium chain" is used to describe the aliphatic chain length of fatty acid containing molecules. "Medium chain" specifically refers to fatty acids, fatty acid esters, or fatty acid derivatives that contain fatty acid aliphatic tails or carbon chains that contain, for example, 6 to 14 carbon atoms, 8 to 12 carbon atoms, or 8 to 10 carbon atoms.

The terms "medium chain fatty acid" and "medium chain fatty acid derivative" are used to describe fatty acids or fatty acid derivatives with aliphatic tails (i.e., carbon chains) having 6 to 14 carbon atoms. Fatty acids consist of an unbranched or branched aliphatic tail attached to a carboxylic acid functional group. Fatty acid derivatives include, for example, fatty acid esters and fatty acid containing molecules, including, without limitation, mono-, di- and triglycerides that include components derived from fatty acids. Fatty acid derivatives also include fatty acid esters of ethylene or propylene glycol. The aliphatic tails can be saturated or unsaturated (i.e., the latter having one or more double bonds between carbon atoms). In some embodiments, the aliphatic tails are saturated (i.e., no double bonds between carbon atoms). Medium chain fatty acids or medium chain fatty acid derivatives include those with aliphatic tails having 6-14 carbons, including those that are C6-C14, C6-C12, C8-C14, C8-C12, C6-C10, C8-C10, or others. Examples of medium chain fatty acids include, without limitation, caproic acid, caprylic acid, capric acid, lauric acid, myristic acid, and derivatives thereof. In certain embodiments, the medium chain fatty acids used to prepare the various medium chain oils described herein are C8, C10, or a combination thereof.

The term "oil," as used herein, refers to any pharmaceutically acceptable oil, especially medium chain oils, and specifically excluding peanut oil, that can suspend or solubilize bioidentical progesterone or estradiol, including starting materials or precursors thereof, including micronized progesterone and/or micronized estradiol as described herein.

The term "medium chain oil" refers to an oil wherein the composition of the fatty acid fraction of the oil is substantially medium chain (i.e., C6 to C14) fatty acids, i.e., the composition profile of fatty acids in the oil is substantially medium chain. As used herein, "substantially" means that between 20% and 100% (inclusive of the upper and lower limits) of the fatty acid fraction of the oil is made up of medium chain fatty acids, i.e., fatty acids with aliphatic tails (i.e., carbon chains) having 6 to 14 carbons. In some embodiments, about 25%, about 30%, about 35%, about 40%, about 45%, about 50%, about 55%, about 60%, about 65%, about 70%, about 75%, about 85%, about 90% or about 95% of the fatty acid fraction of the oil is made up of medium chain fatty acids. Those of skill in the art will readily appreciate that the terms "alkyl content" or "alkyl distribution" of an oil can be used in place of the term "fatty acid fraction" of an oil in characterizing a given oil or solubilizing agent, and these terms are used interchangeably herein. As such, medium chain oils suitable for use in the pharmaceutical compositions disclosed herein include medium chain oils wherein the fatty acid fraction of the oil is substantially medium chain fatty acids, or medium chain oils wherein the alkyl content or alkyl distribution of the oil is substantially medium chain alkyls e.g., C6-C14 alkyls, but also including, for example, C6-C12 alkyls, C8-C12 alkyls, and C8-C10 alkyls. It will be understood by those of skill in the art that the medium chain oils suitable for use in the pharmaceutical compositions disclosed herein are pharmaceutical grade (e.g., pharmaceutical grade medium chain oils). Examples of medium chain oils include, for example and without limitation, medium chain fatty acids, medium chain fatty acid esters of glycerol (e.g., for example, mono-, di-, and triglycerides), medium chain fatty acid esters of propylene glycol, medium chain fatty acid derivatives of polyethylene glycol, and combinations thereof.

The term "ECN" or "equivalent carbon number" means the sum of the number of carbon atoms in the fatty acid chains of an oil, and can be used to characterize an oil as, for example, a medium chain oil or a long-chain oil. For example, tripalmitin (tripalmitic glycerol), which is a simple triglyceride containing three fatty acid chains of 16 carbon atoms, has an ECN of 3×16=48. Conversely, a triglyceride with an ECN=40 may have "mixed" fatty acid chain lengths of 8, 16, and 16; 10, 14, and 16; 8, 14, and 18; etc. Naturally occurring oils are frequently "mixed" with respect to specific fatty acids, but tend not to contain both long chain fatty acids and medium chain fatty acids in the same glycerol backbone. Thus, triglycerides with ECN's of 21-42 typically contain predominately medium chain fatty acids; while triglycerides with ECN's of greater than 43 typically contain predominantly long chain fatty acids. For example, the ECN of corn oil triglyceride in the USP would be in the range of 51-54. Medium chain diglycerides with ECN's of 12-28 will often contain predominately medium chain fatty chains, while diglycerides with ECN's of 32 or greater will typically contain predominately long chain fatty acid tails. Monoglycerides will have an ECN that matches the chain length of the sole fatty acid chain. Thus, monoglyceride ECN's in the range of 6-14 contain mainly medium chain fatty acids, and monoglycerides with ECN's 16 or greater will contain mainly long chain fatty acids.

The average ECN of a medium chain triglyceride oil is typically 21-42. For example, as listed in the US Pharmacopeia (USP), medium chain triglycerides have the following composition as the exemplary oil set forth in the table below:

| Fatty-acid Tail Length | % of oil | Exemplary Oil |
|---|---|---|
| 6 | ≤2.0 | 2.0 |
| 8 | 50.0-80.0 | 70.0 |
| 10 | 20.0-50.0 | 25.0 |
| 12 | ≤3.0 | 2.0 |
| 14 | ≤1.0 | 1.0 | and would have an average ECN of $3*[(6*0.02)+(8*0.70)+(10*0.25)+(12*0.02)+(14*0.01)]=25.8$. The ECN of the exemplary medium chain triglycerides oil can also be expressed as a range (per the ranges set forth in the USP) of 24.9-27.0. For oils that have mixed mono-, di-, and triglycerides, or single and double fatty acid glycols, the ECN of the entire oil can be determined by calculating the ECN of each individual component (e.g., C8 monoglycerides, C8 diglycerides, C10 monoglycerides, and C10 diglycerides) and taking the sum of the relative percentage of the component multiplied by the ECN normalized to a monoglyceride for each component. For example, an oil having C8 and C10 mono- and diglycerides shown in the table below has an ECN of 8.3, and is thus a medium chain oil.

| Fatty-acid ChainLength | % of oil | ECN as % of oil (chain length) × (% in oil) | ECN as % of oil normalized to monoglyceride |
|---|---|---|---|
| C8 monoglyceride | 47 | 8 × 0.47 = 3.76 | 3.76 |
| C10 monoglyceride | 8 | 10 × 0.08 = 0.8 | 0.8 |
| C8 diglyceride | 38 | 2 × (8 × 0.38) = 6.08 | 6.08/2 = 3.04 |
| C10 diglyceride | 7 | 2 × (10 × 0.07) = 1.4 | 1.4/2 = 0.7 |
| OIL ECN (normalized to monoglycerides) | | | 8.3 |

Expressed differently, ECN can be calculated as each chain length in the composition multiplied by its relative percentage in the oil: $(8*0.85)+(10*0.15)=8.3$.

The term "polysorbate" refers to a compound having the structure:

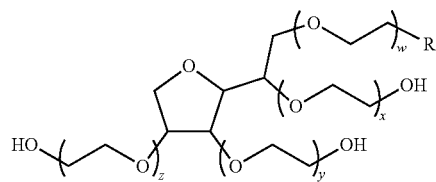

wherein w+x+y+z ranges from about 10 to about 50, and in particular embodiments, from about 10 to about 30, and wherein R is a C6-C18 fatty acid radical. Exemplary polysorbates within the scope of the present definition include, but are not limited to, polysorbate 20, polysorbate 40, polysorbate 60, polysorbate 65, and polysorbate 80.

This disclosure provides methods for improving the solubility of a steroid hormone such as progesterone, estradiol, or a combination of these steroid hormones. This disclosure also provides compositions comprising at least one steroid hormone and at least one solubilizing agent, as well as methods of preparing the same. The compositions provided by this disclosure can be in the form of a unit dosage product and can exhibit improved dissolution profiles, bioavailability, or higher stability relative to currently marketed products. The compositions provided by this disclosure can also be non-allergic or non-antigenic. This disclosure also encompasses use of a terpene such as limonene for improving the solubility of steroid hormones. This disclosure also provides methods of treating physiological conditions linked to an insufficiency of one or more steroid hormones, wherein the method comprises administering a composition disclosed herein to a subject in need thereof.

Without wishing to be bound by any particular theory, it is believed that the compositions and methods described herein address the problems associated with known steroid hormone formulations such as poor solubility, poor bioavailability, and poor stability. More specifically, it has now been discovered that terpenes are unexpectedly effective in enhancing the solubility of insoluble steroid hormones such as progesterone and likewise act as excellent penetration enhancers for these same compounds. In particular embodiments, the cyclic terpene d-limonene significantly enhances the solubility and penetration of steroid hormones such as progesterone, rendering the resultant steroid hormone composition more stable. The compositions can also have any combination of enhanced dissolution rates, penetration capabilities, absorption, and bioavailability. For example, d-limonene was found to have excellent solubilizing properties for progesterone, as shown in Table 1, below.

TABLE 1

| Solvent | Concentration of Progesterone (mg/g) for clear solution |
|---|---|
| d-Limonene | 204.0 |
| Absolute Ethanol | 57 | d-Limonene is a colorless, liquid hydrocarbon. d-Limonene is classified as a cyclic terpene and is a major constituent in various citrus fruits such as orange, lemon, mandarin, lime, and grapefruit. d-limonene can be obtained, for example, from citrus fruits by centrifugal separation and steam distillation methods or can be purchased from one or more commercial suppliers.

In certain embodiments, this disclosure provides compositions comprising at least one steroid hormone and at least one terpene. In certain embodiments, the terpene can be d-limonene and the steroid hormone can be progesterone, estradiol, or a combination thereof. In certain embodiments, the composition can further comprise at least one pharmaceutically acceptable carrier. In certain embodiments, in addition to or in place of the carrier, the compositions disclosed herein can also comprise at least one additional additive, including, without limitation, co-solvents, thickening agents, triglycerides, or suspending agents. In other embodiments, however, the formulation can be completely or substantially free of these additives. In certain embodiments, the compositions disclosed herein can be substantially or completely peanut oil free.

In certain embodiments, the compositions disclosed herein can comprise from about 0.05% to about 50% w/w; about 0.1% to about 40% w/w; or about 0.5% to about 25% w/w of the steroid hormone. In certain embodiments, the composition can have from about 0.05% w/w steroid hormone to about 20% w/w steroid hormone. In certain embodiments, the steroid hormone can be progesterone. In other embodiments, the steroid hormone can be a mixture of progesterone and estradiol. In certain embodiments, the compositions can comprise up to about 10% w/w progesterone, up to about 11% w/w progesterone, up to about 12% w/w progesterone, up to about 13% w/w progesterone, up to about 14% w/w progesterone, up to about 15% w/w progesterone, up to about 16% w/w progesterone, or up to about 17% w/w progesterone. In other embodiments, the compositions can comprise about 10% w/w progesterone, about 11% w/w progesterone, about 12% w/w progesterone, about 13% w/w progesterone, about 14% w/w progesterone, about 15% w/w progesterone, about 16% w/w progesterone, or about 17% w/w progesterone.

Although the steroid hormone used to formulate the composition can have any particle size, such as, for example only, an average particle size of less than about 100 microns. In certain embodiments, the steroid hormone can be micronized. Without wishing to be bound by any particular theory, it is believed that steroid hormones having a smaller average particle size will be more soluble in the composition, thus enabling a reduction in the quantity of steroid hormone in the composition necessary to achieve the desired efficacy.

Terpenes are the primary constituents of the essential oils of many types of plants and flowers and are typically formed directly from one or more isoprene ($C_5H_8$) units. Terpenes can be naturally occurring or prepared synthetically. Terpenes can be obtained from their natural source, for example, isolated from a natural oil such as citrus oil or orange oil, and optionally purified to be substantially pure, or synthesized chemically. In certain embodiments, the terpene can be a terpenoid. Examples of terpenes are provided, for example, in Dev et al., "CRC Handbook of Terpenoids: Acyclic, Monocyclic, Bicyclic, Tricyclic, and Tetracyclic Terpenoids" (1989) CRC Press Inc.; Hanson, J. R., Annu. Rep. Prog. Chem., Sect. B: Org. Chem., (1985) 82, 353-375; and Degenhardt et al., Phytochemistry (2009) 70:1621-1637. The terpene can be linear or cyclic (including aromatic). A cyclic terpene can be a monocyclic terpene or a bicyclic terpene compound. In a particular embodiment, the cyclic terpene can be a monocyclic terpene. In certain embodiments, the cyclic terpene can be non-aromatic. Examples of cyclic terpenes include, without limitation, limonene (as d-limonene, l-Limonene, or a mixture thereof), phellandrene (alpha or beta), camphor, menthol, menthene, carvone, terpinene (alpha, beta, or gamma), terpineol (alpha, beta, or gamma), alpha-ionone, thujone, and derivatives thereof. In certain embodiments, the cyclic terpene is limonene, menthene, menthol, phellandrene, terpinene, or terpineol. In other embodiments, the terpene is d-limonene.

In certain embodiments, the compositions disclosed herein can comprise from about 0.5% to about 95.5% w/w; about 0.5% to about 50% w/w; about 1% to about 25% w/w; or about 1% to about 10% w/w of terpene. In particular embodiments, the composition can comprise at least about 80% w/w terpene and in further embodiments, about 81% w/w terpene, about 82% w/w terpene, about 83% w/w terpene, about 84% w/w terpene, about 85% w/w terpene, about 86% w/w terpene, about 87% w/w terpene, about 88% w/w terpene, about 89% w/w terpene, about 90% w/w terpene, about 91% w/w terpene, about 92% w/w terpene, about 93% w/w terpene, about 94% w/w terpene, about 95% w/w terpene, about 96% w/w terpene, about 97% w/w terpene, about 98% w/w terpene, or about 99% w/w terpene. In particular embodiments, the composition can comprise from about 80% w/w terpene to about 99% w/w terpene, and in other embodiments, from about 80% w/w terpene to about 85% w/w terpene, or from about 80% w/w terpene to about 83% w/w terpene.

In certain embodiments, the terpene is d-limonene. In particular embodiments, the composition can comprise at least about 80% w/w d-limonene and in further embodiments, about 81% w/w d-limonene, about 82% w/w d-limonene, about 83% w/w d-limonene, about 84% w/w d-limonene, about 85% w/w d-limonene, about 86% w/w d-limonene, about 87% w/w d-limonene, about 88% w/w d-limonene, about 89% w/w d-limonene, about 90% w/w d-limonene, about 91% w/w d-limonene, about 92% w/w d-limonene, about 93% w/w d-limonene, about 94% w/w d-limonene, about 95% w/w d-limonene, about 96% w/w d-limonene, about 97% w/w d-limonene, about 98% w/w d-limonene, or about 99% w/w d-limonene. In particular embodiments, the composition can comprise from about 80% w/w d-limonene to about 99% w/w d-limonene, and in other embodiments, from about 80% w/w d-limonene to about 85% w/w d-limonene, or from about 80% w/w d-limonene to about 83% w/w d-limonene.

In other embodiments, the compositions disclosed herein can comprise a terpene, such as, but not limited to, d-limonene, in an amount sufficient to enhance penetration of the steroid hormone. In such embodiments, the composition can comprise less than about 80% w/w based on the total weight of the composition. In other embodiments, the composition comprises about 5% to about 75% w/w terpene, about 5% to about 70% w/w terpene, about 5% to about 65% w/w terpene, about 5% to about 60% w/w terpene, about 5% to about 55% w/w terpene, about 5% to about 50% w/w terpene, about 5% to about 45% w/w terpene, about 5% to about 40% w/w terpene, about 5% to about 35% w/w terpene, about 5% to about 30% w/w terpene, about 5% to about 25% w/w terpene, about 5% to about 15% w/w terpene, or about 5% to about 10% w/w terpene. In these embodiments, the remainder of the composition can comprise one or more pharmaceutically acceptable solvents suitable for suspending or dissolving at least a portion of the steroid hormone present in the composition. Suitable pharmaceutically acceptable solvents for suspending or dissolving a steroid hormone are known to those of ordinary skill in the art and include, but are not limited to, medium chain oils and pharmaceutically acceptable alcohols.

In certain embodiments, this disclosure provides a micelle-forming pharmaceutical composition providing enhanced oral bioavailability of a steroid hormone, such as progesterone, wherein the pharmaceutical composition can comprise a steroid hormone, such as progesterone, a polysorbate, a medium chain oil, and a terpene such as d-limonene.

In certain embodiments, the medium chain oil in the pharmaceutical composition can comprise at least about 50 weight percent of a medium chain monoglyceride. In certain embodiments, the medium chain monoglyceride and progesterone can be present at a weight ratio of about 8:1 to about 15:1, about 9:1 to about 15:1, about 9:1 to about 14:1, about 9:1 to about 13:1, about 9:1 to about 12:1, about 9:1 to about 11:1, or about 10:1. In particular embodiments, the medium chain monoglyceride and progesterone can be present in a ratio of about 10:1.

In certain embodiments, the polysorbate can comprise from about 1 weight percent to about 15 weight percent of the pharmaceutical composition and in particular embodiments, can be about 1 weight percent, about 2 weight percent, about 3 weight percent, about 4 weight percent, about 5 weight percent, about 6 weight percent, about 7 weight percent, about 8 weight percent, about 9 weight percent, about 10 weight percent, about 11 weight percent, about 12 weight percent, about 13 weight percent, about 14 weight percent, or about 15 weight percent of the pharmaceutical composition. In particular embodiments, the polysorbate can be about 5 weight percent or about 7 weight percent of the pharmaceutical composition.

In certain embodiments, the steroid hormone and the polysorbate present in the pharmaceutical composition are present in a weight ratio of about 1:2 to about 2:1.

In certain embodiments, the polysorbate can be selected from the group consisting of polysorbate 20, polysorbate 40, polysorbate 60, polysorbate 65, and polysorbate 80. These polysorbates are commercially available and well known to those of skill in the art. In certain embodiments, the polysorbate can be polysorbate 80. In even more particular embodiments, the polysorbate 80 can comprise about 5 weight percent or about 7 weight percent of the pharmaceutical composition.

In certain embodiments, the medium chain oil can comprise from about 50 weight percent to about 90 weight percent of the pharmaceutical composition. In particular embodiments, the medium chain oil can comprise from about 60 weight percent to about 90 weight percent, from about 65 weight percent to about 90 weight percent, from about 70 weight percent to about 90 weight percent, from about 75 weight percent to about 90 weight percent, or from about 75 weight percent to about 85 weight percent. In particular embodiments, the medium chain oil can comprise about 80 weight percent or about 85 weight percent of the pharmaceutical composition.

In certain embodiments, the medium chain oil can comprise a single medium chain oil component. In other embodiments, the medium chain oil can comprise a first medium chain oil component and a second medium chain oil component. In still further embodiments, the medium chain oil can comprise a first medium chain oil component, a second medium chain oil component, and a third medium chain oil component. In still further embodiments, the medium chain oil can comprise first, second, third and fourth; first, second, third, fourth, and fifth; or first, second, third, fourth, fifth, and sixth medium chain oil components.

In certain embodiments, the medium chain oil components themselves can be multi-component oils. For example, certain medium chain oils comprise a mixture of mono and diglycerides or a mixture of mono-, di-, and triglycerides, etc.

In particular embodiments, the medium chain oil can comprise a first medium chain oil component and a second medium chain oil component, with the first medium chain oil component comprising from about 30 weight percent to about 98 weight percent of the medium chain oil. In other embodiments, the first medium chain oil component can comprise from about 40 weight percent to about 95 weight percent of the medium chain oil. In still further embodiments, the first medium chain oil component can comprise from about 50 weight percent to about 90 weight percent of the medium chain oil.

In certain embodiments, the medium chain oil can comprise at least about 50 weight percent of a medium chain monoglyceride. In particular embodiments, the medium chain oil can comprise at least about at least about 55 weight percent of a medium chain monoglyceride, at least about at least about 60 weight percent of a medium chain monoglyceride, at least about 65 weight percent of a medium chain monoglyceride, at least about 70 weight percent of a medium chain monoglyceride, at least about 71 weight percent of a medium chain monoglyceride, at least about 72 weight percent of a medium chain monoglyceride, at least about 73 weight percent of a medium chain monoglyceride, at least about 74 weight percent of a medium chain monoglyceride, at least about 75 weight percent of a medium chain monoglyceride, at least about 76 weight percent of a medium chain monoglyceride, at least about 77 weight percent of a medium chain monoglyceride, at least about 78 weight percent of a medium chain monoglyceride, at least about 79 weight percent of a medium chain monoglyceride, at least about 80 weight percent of a medium chain monoglyceride, at least about 81 weight percent of a medium chain monoglyceride, at least about 82 weight percent of a medium chain monoglyceride, at least about 83 weight percent of a medium chain monoglyceride, at least about 84 weight percent of a medium chain monoglyceride, at least about 85 weight percent of a medium chain monoglyceride, at least about 86 weight percent of a medium chain monoglyceride, at least about 87 weight percent of a medium chain monoglyceride, at least about 88 weight percent of a medium chain monoglyceride, at least about 89 weight percent of a medium chain monoglyceride, or at least about 90 weight percent of a medium chain monoglyceride. In certain embodiments, the medium chain oil can comprise at least about 85 weight percent of a medium chain monoglyceride and in an even further embodiment, the medium chain oil can comprise at least about 90 weight percent of a medium chain monoglyceride.

The medium chain monoglyceride can be, predominantly, a single medium chain monoglyceride, such as glyceryl monocaproate, glyceryl monocaprylate, glyceryl monocaprate, glyceryl monolaurate, or glyceryl monomyristate. These monoglycerides are well known to those of ordinary skill in the art and are available in various commercial embodiments, including from ABITEC Corp, a division of Associated British Food, PLC, as CAPMUL 708G, CAPMUL 808G, CAPMUL MCM C8, and CAPMUL MCM C10. In particular embodiments, the medium chain monoglyceride can be, predominantly, a single medium chain monoglyceride such as glyceryl monocaproate, glyceryl monocaprylate, or glyceryl monocaprate. In specific embodiments, the medium chain monoglyceride can be, predominantly, glyceryl monocaprylate, commercially available as CAPMUL 708G.

In other embodiments, the medium chain monoglyceride can comprise a mixture of medium chain monoglycerides, such as a combination of two or more of glyceryl monocaproate, glyceryl monocaprylate, glyceryl monocaprate, glyceryl monolaurate, or glyceryl monomyristate. In particular embodiments, the mixture of medium chain monoglycerides can be a mixture of glyceryl monocaprylate and glyceryl monocaprate. In embodiments such as this, the glyceryl monocaprylate can comprise at least about 80 weight percent, at least about 85 weight percent, at least about 86 weight percent, at least about 87 weight percent, at least about 88 weight percent, at least about 88 weight percent, at least about 89 weight percent, or at least about 90 weight percent of the mixture of monoglycerides.

In certain embodiment, in addition to comprising a medium chain monoglyceride, the medium chain oil can further comprise one or more medium chain diglycerides. The one or more medium chain diglycerides can be simple diglycerides, such as glyceryl dicaproate, glyceryl dicaprylate, glyceryl dicaprate, glyceryl dilaurate, or glyceryl dimyristate. Alternatively, the one or more medium chain diglycerides can be mixed or complex diglycerides such as glyceryl caproate/caprylate, glyceryl caproate/caprate, glyceryl caproate/laurate, glyceryl caproate/myristate, glyceryl caprylate/caprate, glyceryl caprylate/laurate, glyceryl caprylate/myristate, glyceryl caprate/laurate, glyceryl caprate/myristate, or glyceryl laurate/myristate. In specific embodiments, the one or more medium chain diglycerides can be glyceryl caprylate/caprate. Exemplary commercially available medium chain diglycerides include, but are not limited to, CAPMUL 471, CAPMUL MCM, CAPMUL MCM NF, CAPMUL MCM EP, and IMWITOR 742. The CAPMULs are commercially available from ABITEC Corp.

The one or more medium chain diglycerides can comprise up to about 10 weight percent of the medium chain oil or alternatively from about 5 to about 10 weight percent of the pharmaceutical composition. In particular embodiments, the one or more medium chain diglycerides can comprise about 5 weight percent, about 6 weight percent, about 7 weight percent, about 8 weight percent, about 9 weight percent, or about 10 weight percent of the pharmaceutical composition. In specific embodiments, the one or more medium chain diglycerides can comprise about from about 8 to about 9 weight percent of the pharmaceutical composition, such as about 8 weight percent, about 8.1 weight percent, about 8.2 weight percent, about 8.3 weight percent, about 8.4 weight percent, about 8.5 weight percent, about 8.6 weight percent, about 8.7 weight percent, about 8.8 weight percent, about 8.9 weight percent, or about 9 weight percent of the pharmaceutical composition.

In certain embodiments, the one or more medium chain diglycerides can be glyceryl caprylate/caprate and the pharmaceutical composition can comprise about 8 weight percent to about 9 weight percent of this component. A commercially available component suitable for use in the pharmaceutical composition is CAPMUL MCM NF.

The quantity of terpene present in the micelle-forming compositions can range from about 1 weight percent to about 5 weight percent. In other embodiments, the quantity of terpene in the composition can be about 1 weight percent, about 2 weight percent, about 3 weight percent, about 4 weight percent, or about 5 weight percent. In other embodiments, the quantity of terpene present in the micelle-forming composition can be about 3.5 weight percent, about 3.6 weight percent, about 3.7 weight percent, about 3.8 weight percent, about 3.9 weight percent, about 4 weight percent, about 4.1 weight percent, about 4.2 weight percent, about 4.3 weight percent, about 4.4 weight percent, or about 4.5 weight percent. In particular embodiments, the quantity of terpene present in the micelle-forming compositions can be about 4.2 weight percent.

Because of the manner in which they are prepared, medium chain oils often contain some amount of material that is greater in length than C14. That said, this fraction is typically small and does not affect the overall performance of a given medium chain oil. As such, and in certain embodiments, the amount of material greater than C14 in a given medium chain oil comprises less than 20 weight percent, less than 15 weight percent, less than 5 weight percent, less than 2.5 weight percent, less than 1 weight percent, less than 0.5 weight percent, or less than 0.1 weight percent of a given medium chain oil.

Similarly, monoglycerides and diglycerides often contain di- and triglyceride components in the case of a monoglyceride or mono- and triglycerides in the case of diglycerides. The quantity of these components in a given mono- or diglyceride can vary, but is typically less than 20 weight percent, less than 15 weight percent, less than 5 weight percent, less than 2.5 weight percent, less than 1 weight percent, less than 0.5 weight percent, or less than 0.1 weight percent of the mono- or diglyceride. In all cases, the average ECN will be in the range of 12-28 for diglycerides and 6-14 for monoglycerides.

In addition to the components noted above, in certain embodiments, the pharmaceutical composition can optionally further include a polyoxyethylene hydrogenated castor oil. In particular embodiments, the polyoxyethylene hydrogenated castor oil can be referred to as a "PEG (or polyoxyl) X Hydrogenated Castor Oil," wherein X refers to the amount of pegylation. In particular embodiments, X can be a number from 1 to 100 and in certain embodiments, can be 7, 40, 40-45, or 60. Exemplary commercially available PEG/polyoxyl X hydrogenated castor oils include CREMOPHOR EL, CREMOPHOR RH40 (available commercially from BASF as polyoxyl 40 hydrogenated castor oil (also known as KOLLIPHOR RH 40)), ETOCAS 40, CRODURET 7, CRODURET 40, CRODURET 50, CRODURET 60, and KOLLIPHOR HS 15. In particular embodiments, the polyoxyethylene hydrogenated castor oil can be polyoxyl 40 hydrogenated castor oil (KOLLIPHOR RH 40).

When present, the polyoxyethylene hydrogenated castor oil can comprise from about 1 to about 10 weight percent of the pharmaceutical composition. In particular embodiments, the polyoxyethylene hydrogenated castor oil can comprise from about 2 to about 9 weight percent of the pharmaceutical composition, from about 3 to about 7 weight percent of the pharmaceutical composition, from about 4 to about 6 weight percent of the pharmaceutical composition, or about 4 to about 5 weight percent of the pharmaceutical composition. In particular embodiments, the polyoxyethylene hydrogenated castor oil can comprise about 4 weight percent of the pharmaceutical composition, about 4.1 weight percent of the pharmaceutical composition, about 4.2 weight percent of the pharmaceutical composition, about 4.3 weight percent of the pharmaceutical composition, about 4.4 weight percent of the pharmaceutical composition, about 4.5 weight percent of the pharmaceutical composition, about 4.6 weight percent of the pharmaceutical composition, about 4.7 weight percent of the pharmaceutical composition, about 4.8 weight percent of the pharmaceutical composition, or about 4.9 weight percent of the pharmaceutical composition.

In other embodiments, the pharmaceutical composition can optionally include a d-α-tocopherol polyethylene glycol succinate (TPGS) derivative having the formula:

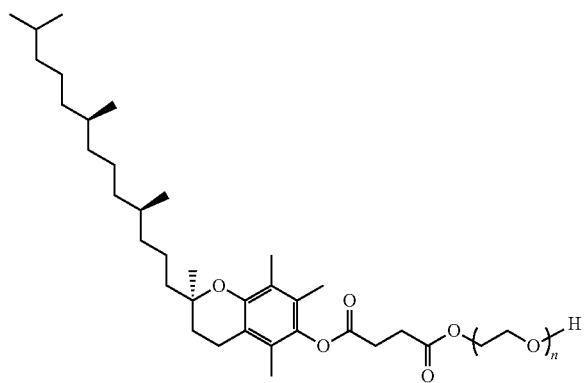

wherein n can range from 1 to about 100, and in particular embodiments, from about 1 to about 50 or about 1 to about 25. In particular embodiments, the D-α-Tocopherol polyethylene glycol succinate derivative can be d-α-tocopherol polyethylene glycol 1000 succinate, also referred to as TPGS-1000 (n 22).

The d-α-tocopherol polyethylene glycol succinate derivative, when present, can comprise from about 0.1 weight percent to about 5 weight percent of the pharmaceutical composition and in particular embodiments about 1 weight percent, about 1.5 weight percent, about 1.75 weight percent, about 2 weight percent, about 2.1 weight percent, about 2.2 weight percent, about 2.3 weight percent, about 2.4 weight percent, about 2.5 weight percent, about 2.75 weight percent, about 3 weight percent, about 3.25 weight percent, about 3.5 weight percent, about 3.75 weight percent, about 4 weight percent, about 4.25 weight percent, about 4.5 weight percent, or about 4.75 weight percent of the pharmaceutical composition. In certain embodiments, the d-α-tocopherol polyethylene glycol succinate derivative can comprise about 2.3 weight percent of the pharmaceutical composition. In other embodiments, the pharmaceutical composition can comprise TPGS-1000 at about 2.3 weight percent.

Generally speaking, and in certain embodiments, when the pharmaceutical composition includes a d-α-tocopherol polyethylene glycol succinate derivative, the pharmaceutical composition does not include a polyoxyethylene hydrogenated castor oil. Similarly, and in certain embodiments, when the pharmaceutical composition includes a polyoxyethylene hydrogenated castor oil, the pharmaceutical composition does not include a d-α-tocopherol polyethylene glycol succinate derivative.

Micelle formation for micelle-forming compositions can be observed by adding these compositions to water or other aqueous-based fluid such as simulated gastric fluid (SGF). The size or size distribution of the micelles resulting from mixing the pharmaceutical compositions with water or SGF can be measured using photon correlation spectroscopy. In certain embodiments, the particles can have a size distribution ranging from about 1 nm to about 1400 nm in water, or from about 130 nm to about 465 nm in water, or from about 100 nm to about 210 nm in water.

In certain embodiments, the micelles can have a zeta potential (mV) ranging from about −10 to about −30 mV. In certain embodiments, the zeta potential of the micelles can be about −10 mV, about −11 mV, about −12 mV, about −13 mV, about −14 mV, about −15 mV, about −16 mV, about −17 mV, about −18 mV, about −19 mV, about −20 mV, about −21 mV, about −22 mV, about −23 mV, about −24 mV, about −25 mV, about −26 mV, about −27 mV, about −28 mV, about −29 mV, or about −30 mV. In certain embodiments, the zeta potential can be about −16 to about −17 mV. In other embodiments, the zeta potential can be about −18 to about −19 mV. In still other embodiments, the zeta potential can be about −20 to about −21 mV.

As stated earlier, this disclosure encompasses methods of treating any condition or disease associated with an absolute or relative deficiency of a steroid hormone. The methods comprise administering at least one composition disclosed herein to the subject in need thereof. For example, a composition comprising progesterone as the steroid hormone can be administered to a subject in order to treat ovulatory bleeding, infertility associated with low progesterone, or early pregnancy complications associated with low progesterone.

In certain embodiments, this disclosure provides compositions comprising at least one steroid hormone and at least one terpene and, optionally, at least one pharmaceutically acceptable carrier, for example, one suitable for oral administration. Such compositions can be administered, in a therapeutically effective amount, to a patient in need thereof for the treatment of a disorder associated with a steroid hormone deficiency. This disclosure also encompasses kits comprising at least one composition disclosed herein, for example, a composition comprising at least one steroid hormone, at least one terpene and, optionally, at least one pharmaceutically acceptable carrier, for example one suitable for oral administration. The kits can comprise multiple dosage units or instruction material for using the compositions. The multiple dosage units can be contained within a container such as a bottle or blister pack.

The agents and compositions of this disclosure can be administered by any suitable route. In certain embodiments, the composition can be administered orally. In general, the optional pharmaceutically acceptable carrier can be selected to be appropriate for the desired route of administration of the pharmaceutical composition. Suitable pharmaceutically acceptable carriers for various routes of administration are known in the art. Except insofar as any of these pharmaceutically acceptable carriers are incompatible with the compositions disclosed herein, use of a given carrier in the pharmaceutical compositions disclosed herein is contemplated. Examples of pharmaceutically acceptable carriers include, without limitation, diluents, preservatives, solubilizers, emulsifiers, adjuvants or excipients.

In certain embodiments, the compositions disclosed herein can also include a pharmaceutically acceptable pH buffering agent; an additive such as a detergent; a solubilizing agent such as polysorbate 80; a preservative such as benzyl alcohol or other known preservatives; or a bulking substance such as lactose or mannitol. The pharmaceutical composition of this disclosure can be prepared, for example, in liquid form.

In certain embodiments, the composition can further include an antioxidant such as α-tocopherol acetate, acetone sodium bisulfite, acetylcysteine, ascorbic acid, ascorbyl palmitate, butylated hydroxyanisole (BHA), butylated hydroxytoluene (BHT), cysteine, cysteine hydrochloride, α-tocopherol, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, tocopherol, or any combination thereof.

Without wishing to be bound by any particular theory, it is believed that antioxidants can be useful in the compositions of this disclosure because terpenes can be easily oxidized, thereby potentially reducing the solubility of the steroid hormone in the composition, increasing irritation due to the presence of the oxidation products, or some combination thereof. In certain embodiments, for example, d-limonene can be oxidized to as many as five different products upon exposure to oxygen in the absence of an antioxidant. The d-limonene oxidation products (R)-(−)-carvone and the cis and trans isomers of (+)-limonene oxide are known potent sensitizers.

Thus, in certain embodiments, the antioxidant can be present in the composition up to about 5 weight percent, and in certain embodiments, up to about 4 weight percent, up to about 3 weight percent, up to about 2 weight percent, up to about 1 weight percent, up to about 0.5 weight percent, up to about 0.25 weight percent, up to about 0.125 weight percent, or about 0.1 weight percent. In certain embodiments, the antioxidant can be present from about 0.05 weight percent to about 0.15 weight percent. In still other embodiments, the antioxidant can be present at 0.1 weight percent. In certain embodiments, the antioxidant is BHT. And in still further embodiments, the BHT is present in the composition at from about 0.05 to about 0.15 weight percent. In other embodiments, the BHT is present at about 0.1 weight percent.

The agents and compositions of this disclosure can be administered by any suitable route. In certain embodiments, the composition can be administered via injection (either intramuscular or intravenous), orally, sublingually, rectally, intravaginally, or topically and can be in the form of a liquid, a cream, a lotion, a gel, an ointment, a foam, syrup, elixir, or any other non-solid dosage form in which the steroid hormone is completely or substantially dissolved and which is appropriate for the given route of administration. Thus, and by way of example only, a liquid formulation could be given via injection, orally, sublingually, topically, rectally, or intravaginally, while it is contemplated that, in certain embodiments, foams, creams, lotions, gels, and ointments can be administered topically or intravaginally.

In certain embodiments, the compositions of this disclosure can be administered orally, sublingually, topically, rectally, intravaginally, or any combination thereof, in the complete or substantial absence of further additives. That is, and by way of example only, a composition comprising the steroid hormone and the terpene in the presence of less than 5 weight percent, and in certain embodiments, less than 2.5 weight percent, or less than 1 weight percent of other components (including, but not limited to, preservatives, antioxidants, etc.) based on the total weight of the composition, can be directly administered to a patient in need thereof. In such embodiment, the composition can be given as a solution to swallow or applied sublingually. In other embodiments, the composition can be applied directly to the skin or be administered via patch or other appropriate delivery device in order to permit transdermal or intradermal absorption of the steroid hormone. Suitable transdermal patches for delivery of liquid formulations are known to those of ordinary skill in the art. See, for example, U.S. Pat. No. 5,591,767 and PCT International Application WO 2013/072763, each of which is incorporated herein by reference in its entirety. In other embodiments, the liquid can be introduced into the vagina or rectum via an appropriate delivery device (for example, a syringe) to allow for the direct transmucosal absorption of the steroid hormone from the colon, vaginal walls, or cervix.

Alternatively, the composition can be encapsulated and administered orally, sublingually, vaginally, rectally, or any combination thereof. In certain embodiments, the composition can be encapsulated in a gelatin capsule, or other similar encapsulated dosage form known to those of skill in the art. The gelatin capsule can be a soft gelatin capsule or a hard gelatin capsule. The hard gelatin capsule can be a two-piece, standard gelatin capsule which typically includes a first capsule half and a second capsule half. The soft gelatin capsule can be a two-piece capsule wherein two portions are sealed together or a one-piece, hermetically sealed capsule.

In certain embodiments, the soft gelatin capsule can be a one-piece, hermetically sealed gelatin based capsule which can be made by techniques known to those skilled in the art. In certain embodiments, the gelatin used to form the soft gelatin capsule can include water, gelatin, and a plasticizer to control the softness and flexibility of the capsule. Other additives for use in the gelatin suitable for preparing the soft gelatin capsule, include but are not limited to, flavorants, colorants, and opacifiers.

Soft gelatin capsules can be produced in a known manner, including with a rotary die process in which a molten mass of a gelatin containing the appropriate or necessary additives, is fed from a reservoir onto drums to form two spaced sheets or ribbons of gelatin in a semi-molten state. These ribbons are fed around rollers and brought together at convergent angle into the nip of a pair of roller dies that include opposed die cavities. A liquid fill formulation, such as the compositions of this disclosure, can then be fed into the wedge-shaped joinder of the ribbons. The gelatin ribbons are continuously conveyed between the dies, with portions of the fill formulation being trapped between the sheets inside the die cavities. The sheets are then pressed together, and severed around each die so that opposed edges of the sheet flow together to form a continuous gelatin sheath around the entrapped liquid composition. The part of the gelatin sheet that is severed from the segments forming the capsules can then be collected for recycling or can be discarded. The resulting soft capsules can then be dried and packaged.

Various gelatin formulations known in the prior art can be used to encapsulate the compositions of this disclosure. For example, suitable gelatin capsules can be prepared from a gelatin mixture comprising from about 30% w/w to about 85% w/w gelatin and in certain embodiments, about 30% w/w to about 50% w/w; about 15% w/w to about 40% w/w of one or more plasticizer; and from 25% w/w to about 50% w/w of water. In certain embodiments, the gelatin will have a bloom in the rage of about 150 to about 275, and can be Type A or B gelatins or a mixture thereof. In certain embodiments, the gelatin used can comprise hydrolyzed gelatin to prevent cross-linking. The amount of hydrolyzed gelatin can range from about 0.1% w/w of the gelatin in the capsule to 100% w/w of the gelatin in the capsule, including all intervening amounts and ranges. Gelatin suitable for encapsulating the compositions of this disclosure can be derived from any source, including cows, pigs, fish, and vegetables.

Examples of suitable Type A gelatin include without limitation acid bone gelatin. Examples of suitable Type B gelatin include without limitation lime bone gelatin.

Suitable gelatin plasticizers are well known to those of ordinary skill in the art and include, but are not limited to, polyhydric alcohols such as sorbitol, glycerin, mannitol, xylitol, maltitol, and sorbitan; dialkylphthalates; lower alkyl citrates wherein the lower alkyl has 1-6 carbon atoms; glycols and polyglycols including polyethylene glycols with a molecular weight range of about 200 to about 2,000, methoxyl-propylene-glycol, and 1,2-propylene glycol; esters of polyhydroxy-alcohols such as mono-, di-, and tri-acetate of glycerol; ricinoleic acid and esters thereof; and mixtures of the above. The gelatin formulation can also contain other ingredients including, but not limited to, taste modifiers, coloring agents, and moisture retaining agents.

Pharmaceutical compositions containing a compound disclosed herein as the active ingredient in intimate admixture with an optional pharmaceutical carrier can be prepared according to conventional pharmaceutical compounding techniques. The carrier can take a wide variety of forms depending on the form of preparation desired for administration for example, parenterally or subcutaneous. Compositions for oral administration can comprise thickeners, flavorings, diluents, emulsifiers, dispersing aids, or binders.

The pharmaceutical compositions described herein can be formulated in dosage unit form for ease of administration and dose uniformity. A dosage unit, as used herein, refers to a physically discrete unit of the pharmaceutical composition appropriate for the patient undergoing treatment. Each dosage can contain a quantity of active ingredient calculated to produce the desired effect in association with an optional pharmaceutical carrier. Dosage units can be proportionately increased or decreased based on the weight of the patient. Appropriate concentrations for alleviation of a particular pathological condition can be determined by dosage concentration curve calculations. Appropriate dosage unit can also be determined by assessing the efficacy of the treatment.

The appropriate dosage unit for the administration of the compositions disclosed herein can be determined by evaluating the toxicity or efficacy of the compositions in in vitro models or animal models. Toxicity and efficacy of the particular compositions described herein can be determined by standard pharmaceutical procedures. The data obtained from these studies can be used in formulating a range of dosage for use in human. Dosage amount and interval can be adjusted individually to levels of the active ingredient which are sufficient to deliver an effective amount. Appropriate dosage unit can also be determined by assessing the efficacy of the agent in combination with or in reference to other standard drugs. The dosage units of the compositions can be determined individually or in combination with each treatment according to the effect desired or detected.

The pharmaceutical compositions provided by this disclosure can be administered at appropriate intervals, for example, once or multiple times per day (e.g., once a day, twice a day, three times a day, four times a day, etc.); once or multiple times every other day (e.g. once a day every other day, twice a day every other day, three times a day every other day, four times a day every other day, etc.); once or multiple times every three days (e.g. once a day every three days, twice a day every three days, three times a day every three days, four times a day every three days, etc.); at least one, two or three times a week; weekly; or less frequently until the condition being treated is reduced or alleviated. In certain embodiments, the dosage can delivered to provide an initial loading dose and then be reduced to a maintenance level, if necessary or desirable. The amount of steroid hormone to be administered as well as the loading period can be determined by a physician of ordinary skill in the art as well as the condition of the patient and the disease or condition to be treated. Although the compositions described here can be given at any time during the day, in certain embodiments, the composition can be administered in the evening. If administered orally, the composition can be administered with food or in the complete or substantial absence of food. In further embodiments, the composition can be orally administered about 1, about 2, about 3, about 4, or about 5 hours after a last meal.

In certain embodiments, the steroid hormone can be can be administered in the range of about 0.1 mg to about 1 g; about 1 mg to about 600 mg; or about 10 mg to about 500 mg. In certain embodiments, the steroid hormone is progesterone. In some embodiments, the progesterone can be administered to a subject in need thereof in a composition as described herein in an amount in the range of about 25 mg to about 500 mg, and in certain embodiments, about 30 mg, about 35 mg, about 40 mg, about 45 mg, about 50 mg, about 55 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, or any range encompassing any of the noted values.

In further embodiments, the compositions of this disclosure can be used to treat any condition susceptible to treatment with a steroid hormone. In certain embodiments, the condition can be amenorrhea. In other embodiments, the condition can be endometrial hyperplasia. Treatment of these conditions can be provided through any of the routes described herein and can be undertaken using the composition in unencapsulated form, encapsulated form, or some combination thereof.

EXAMPLES

Example 1: Microscopic Characterization of Progesterone Compositions

Figure 2:
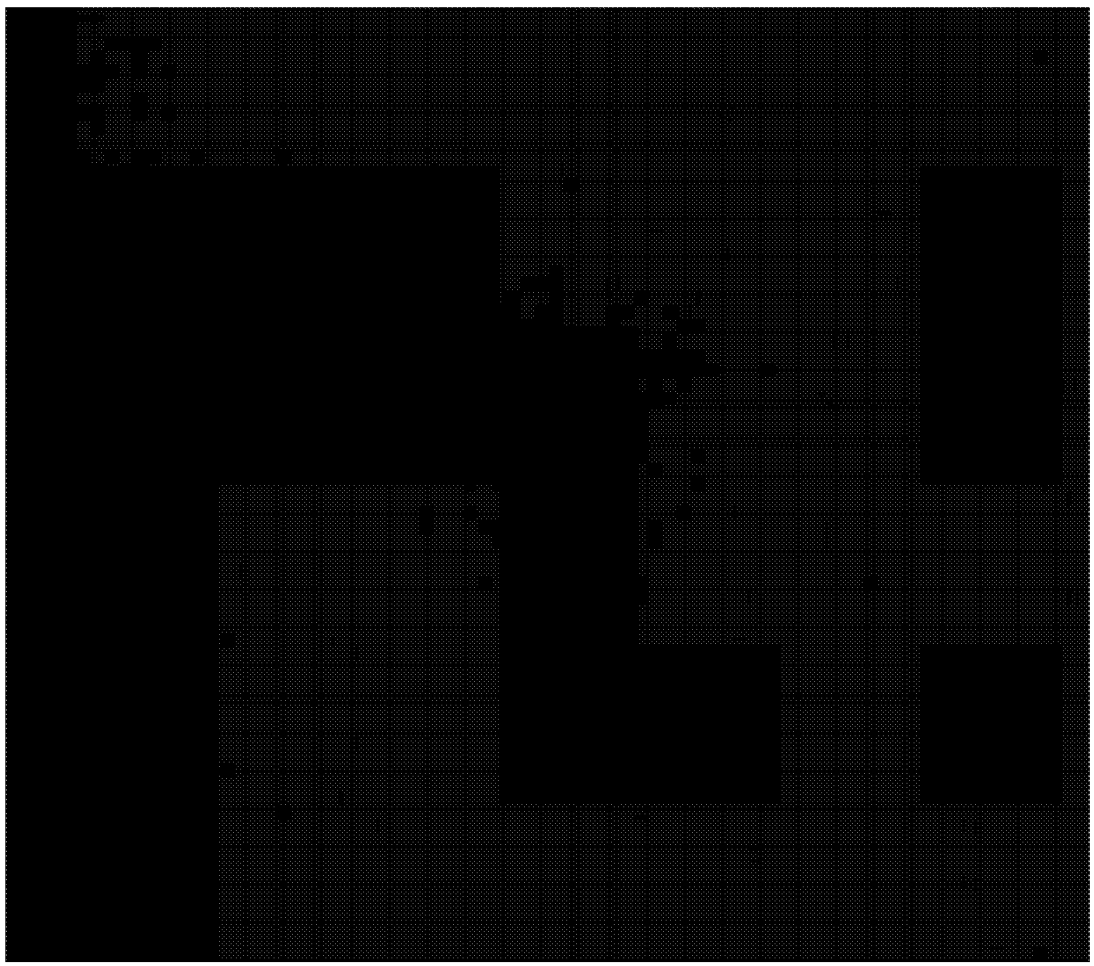
FIG. 2 shows Cream 1 as described herein viewed with a birefringence microscope using polarized light (10×40).
Figure 3:
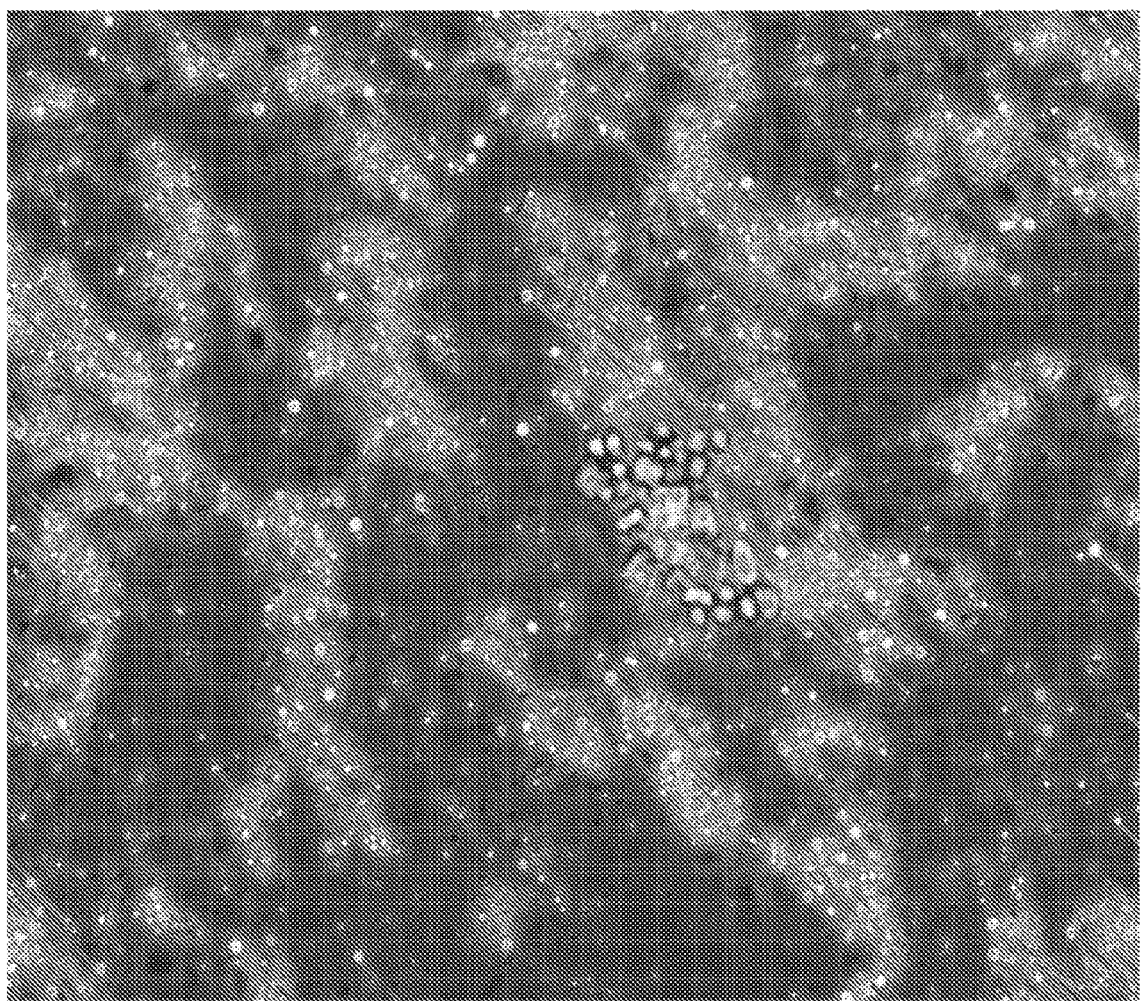
FIG. 3 shows Cream 2 as described herein viewed with a birefringence microscope using non-polarized light (10×40).
Figure 4:
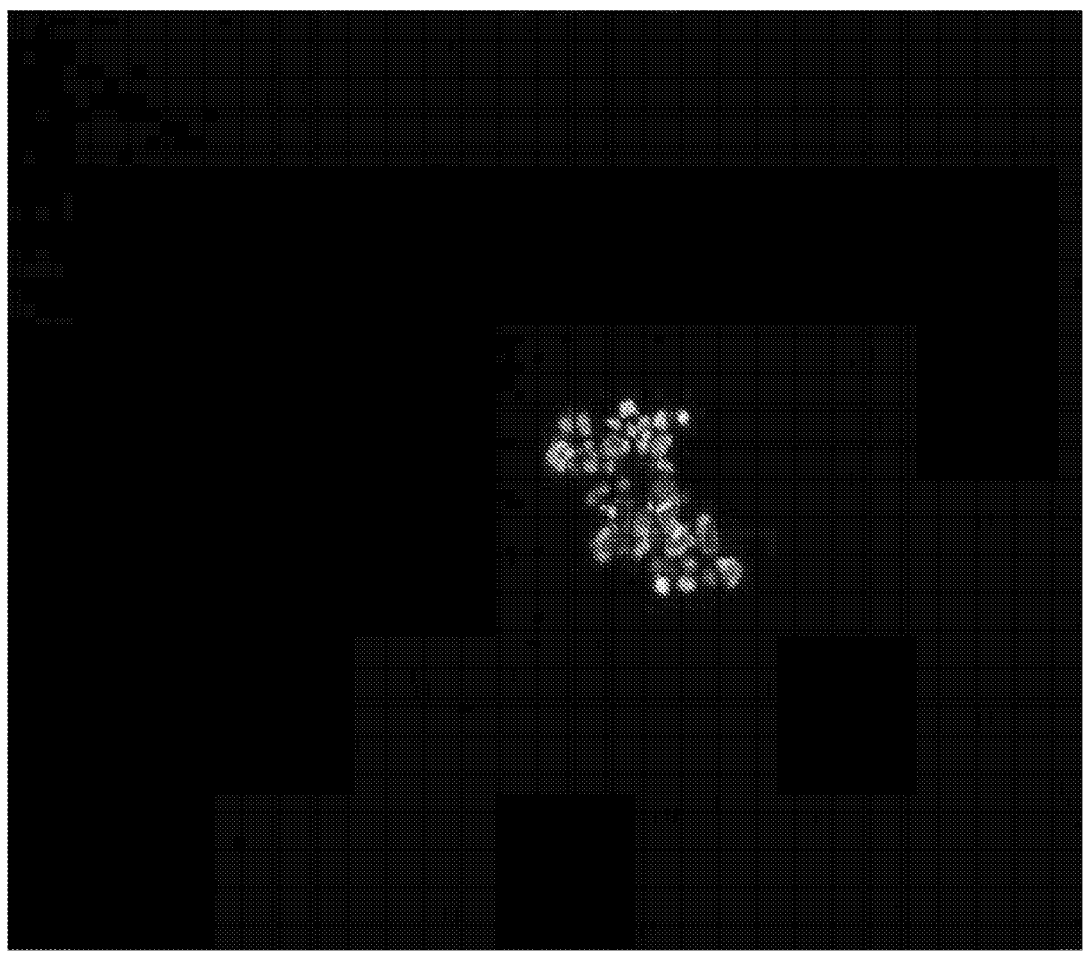
FIG. 4 shows Cream 2 as described herein viewed with a birefringence microscope using polarized light (10×40).

Creams 1 and 2, described in Table 2, below, were prepared according to standard techniques. The compositions differed only in the presence or absence of d-limonene. The creams were examined using a birefringence microscope to determine the presence or absence of progesterone crystals. Pure progesterone crystals (confirmed via IR) were observed in Cream 2, (FIGS. 3 and 4) but no crystals were observed in Cream 1 (FIGS. 1 and 2).

TABLE 2

| Ingredients | Cream 1 % w/w | Cream 1 Qty/Batch | Cream 2 % w/w | Cream 2 Qty/Batch |
|---|---|---|---|---|
| Progesterone Micronized, USP | 2.5% | 25.0 g | 2.5% | 25.0 g |
| Medium Chain Triglycerides, NF (Miglyol 812) | 15.0% | 150.0 g | 15.0% | 150.0 g |
| d-Limonene | 5.0% | 50.0 g | N/A | N/A |
| Diethylene Glycol Mono Ethyl Ether EP/NF (Transcutol P) | 3.0% | 30.0 g | 3.0% | 30.0 g |
| Propylene Glycol Monolaurate (Type II) EP/NF, (Lauroglycol 90) | 5.0% | 50.0 g | 5.0% | 50.0 g |
| Mixture of Glycerol monostearate EP/NF and PEG-75 stearate NF/JPE, (Gelot 64) | 7.0% | 70.0 g | 7.0% | 70.0 g |
| Mixture of Cetyl Alcohol EP/NF and Ethoxylated Fatty Alcohols (Ceteth-20, Steareth-20) EP/NF, (Emulcire 61 WL 2659) | 3.5% | 35.0 g | 3.5% | 35.0 g |
| Carbopol 980 NF Polymer | 0.2% | 2.0 g | 0.2% | 2.0 g |
| Liquid Soy Lecithin | 3.0% | 30.0 g | 3.0% | 30.0 g |
| Propylene Glycol, USP | 4.0% | 40.0 g | 4.0% | 40.0 g |
| Methyl Paraben, NF | 0.2% | 2.0 g | 0.2% | 2.0 g |
| Propyl Paraben, NF, EP, BP, JP | 0.02% | 0.2 g | 0.02% | 0.2 g |
| Citric Acid Monohydrate, Granular, USP | 0.47% | 4.70 g | 0.53% | 5.30 g |
| Dibasic Sodium Phosphate, Dried, USP | 0.82% | 8.20 g | 0.92% | 9.20 g |
| Purified Water, USP | QS | 502.90 | QS | 551.30 |
| TOTAL | 100% | 1000.0 g | 100% | 1000.0 g |

This data demonstrates that d-limonene can be an effective progesterone solubilizing agent in complex formulations.

Example 2: Combined Progesterone/Estradiol Formulation

Cream 1 in Table 2 was combined with estradiol in the proportions specified in Table 3, below. TRANSCUTOL P was used to solubilize estradiol.

TABLE 3

| Ingredients | % w/w | Qty./Batch |
|---|---|---|
| Progesterone 2.5% Cream (Cream 1) | 99.595 | 497.975 g |
| Micronized Estradiol Hemihydrate, USP | 0.005% | 0.025 g |
| Transcutol P[(1)] | 0.4% | 2.0 g |
| TOTAL | 100% | 500.00 g |

Addition of estradiol and TRANSCUTOL P did not induce progesterone crystallization.

Example 3: Transdermal Delivery of Progesterone Opposes the Effects of Estradiol in Female Rats Transdermally delivered progesterone blocked growth-related estrogenic effects on the endometrium and vagina in ovariectomized rats. More specifically, when Cream 1 in Table 2 (including 0.1% w/w butylated hydroxytoluene) was applied topically to a rat model, progesterone successfully penetrated the skin of the rat model to an extent that resulted in clinically-relevant cellular changes on reproductive organs.

Thirty-two 8-week-old female Crl:CD® rats underwent ovariectomy 2 weeks prior to the start of the study. Rats were then randomly assigned to 4 groups of 8 rats each and dosed according to the schedule in Table 4. Control animals were dosed with saline or vehicle as noted. Two hours after the final dose on Day 8, the rats were humanely euthanized and the rats' vaginas and the distal portions of the rats' uterine horns were fixed and processed for histology and computer-aided morphometry.

TABLE 4

| Group | Treatment | Route | Treatment Day | Dose Level | Dose Volume | Number of Animals Day 1 | Number of Animals Day 8 |
|---|---|---|---|---|---|---|---|
| 1 (Control) | 17-β-Estradiol vehicle (Saline) | SQ | 1-8 | 0 | 5 (mL/kg) | 8 | 8 |
|  | Transdermal Progesterone vehicle | Dermal | 4-8 | 0 | 125 µL/day | 8 | 8 |
| 2 | 17-β-Estradiol | SQ | 1-8 | 3 µg/kg/Day | 5 (mL/kg) | 8 | 8 |
|  | Transdermal Progesterone vehicle | Dermal | 4-8 | 0 | 125 µL/day | 8 | 8 |

TABLE 4-continued

| Group | Treatment | Route | Treatment Day | Dose Level | Dose Volume | Number of Animals Day 1 | Number of Animals Day 8 |
|---|---|---|---|---|---|---|---|
| 3 | 17-β-Estradiol | SQ | 1-8 | 3 μg/kg/day | 5 (mL/kg) | 8 | 8 |
|   | Progesterone | SQ | 4-8 | 10 mg/kg/day | 5 (mL/kg) | 8 | 8 |
| 4 | 17-β-Estradiol | SQ | 1-8 | 3 μg/kg/day | 5 (mL/kg) | 8 | 8 |
|   | Transdermal Progesterone | Dermal | 4-8 | 3.125 mg/day | 125 μL/day | 8 | 8 |

As expected with this model, ovariectomy without hormone replacement resulted in significant atrophy of the uterus while unopposed estradiol treatment lead to hypertrophy as demonstrated by organ weight measurements and histology.

Figure 5:
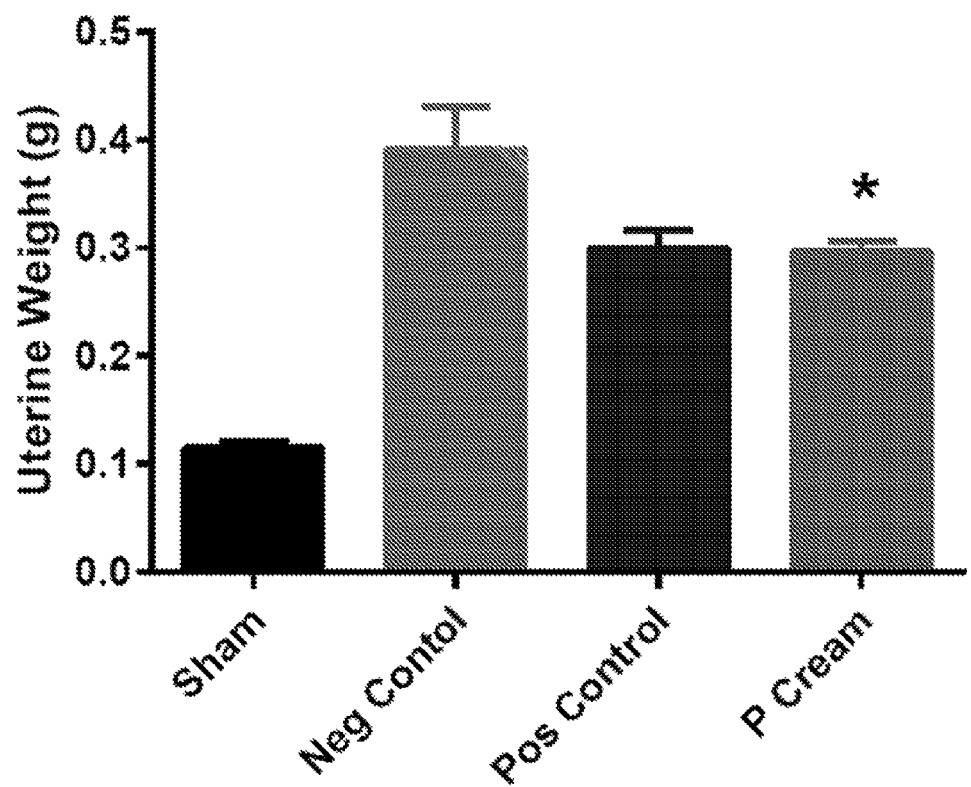
FIGS. 5 and 6 show uterine weight data collected for rats treated with estradiol or estradiol/progesterone after ovariectomy.
Figure 6:
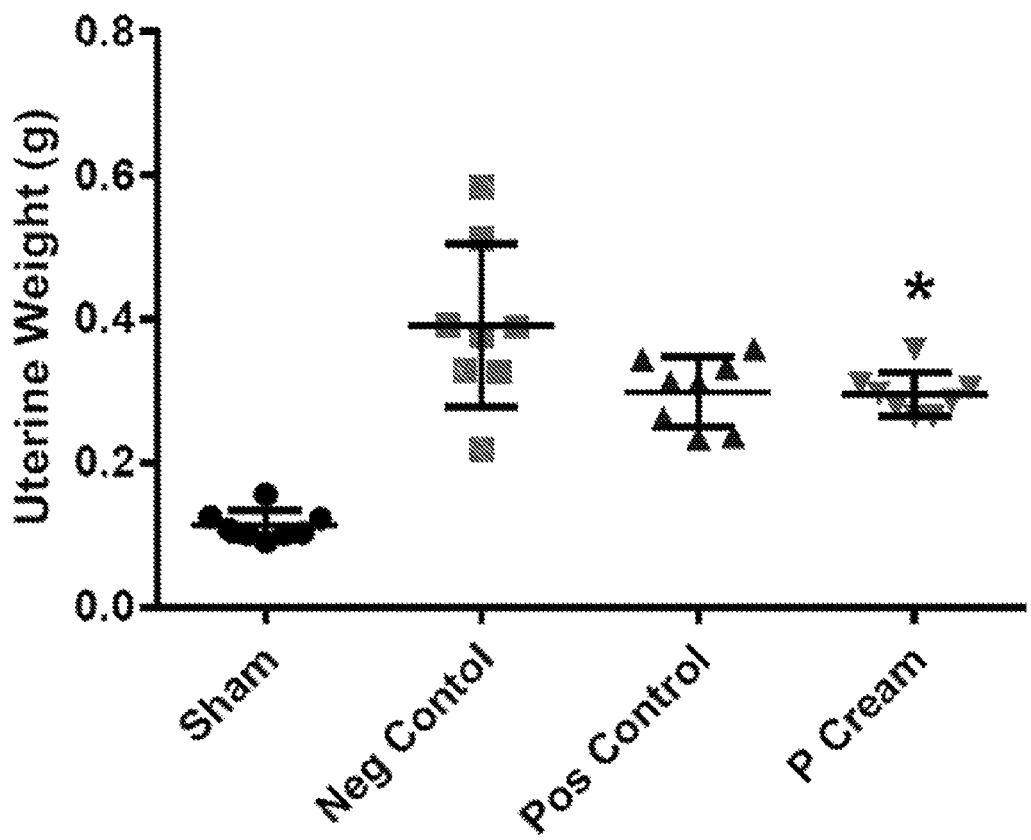
Figure 7:
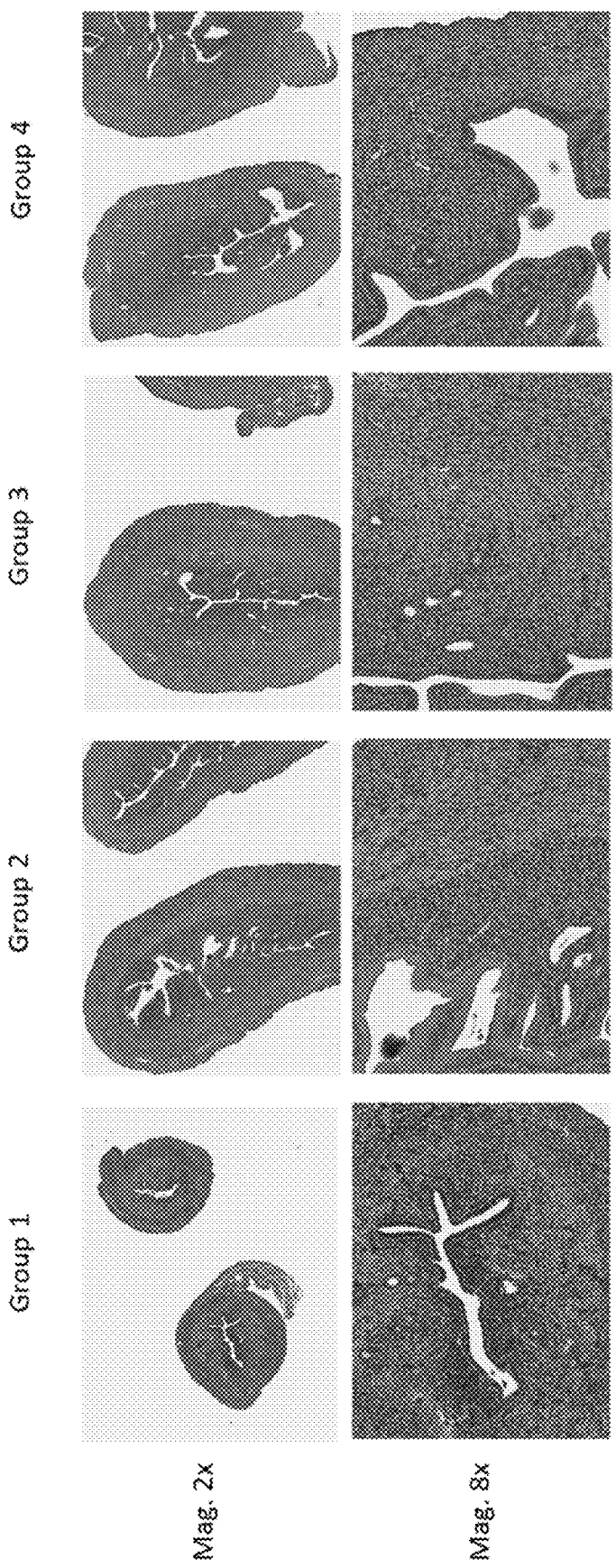
FIG. 7 shows uterine histologic specimens (stained with hematoxylin and eosin) collected from rats treated with estradiol or estradiol/progesterone after ovariectomy.
Figure 8:
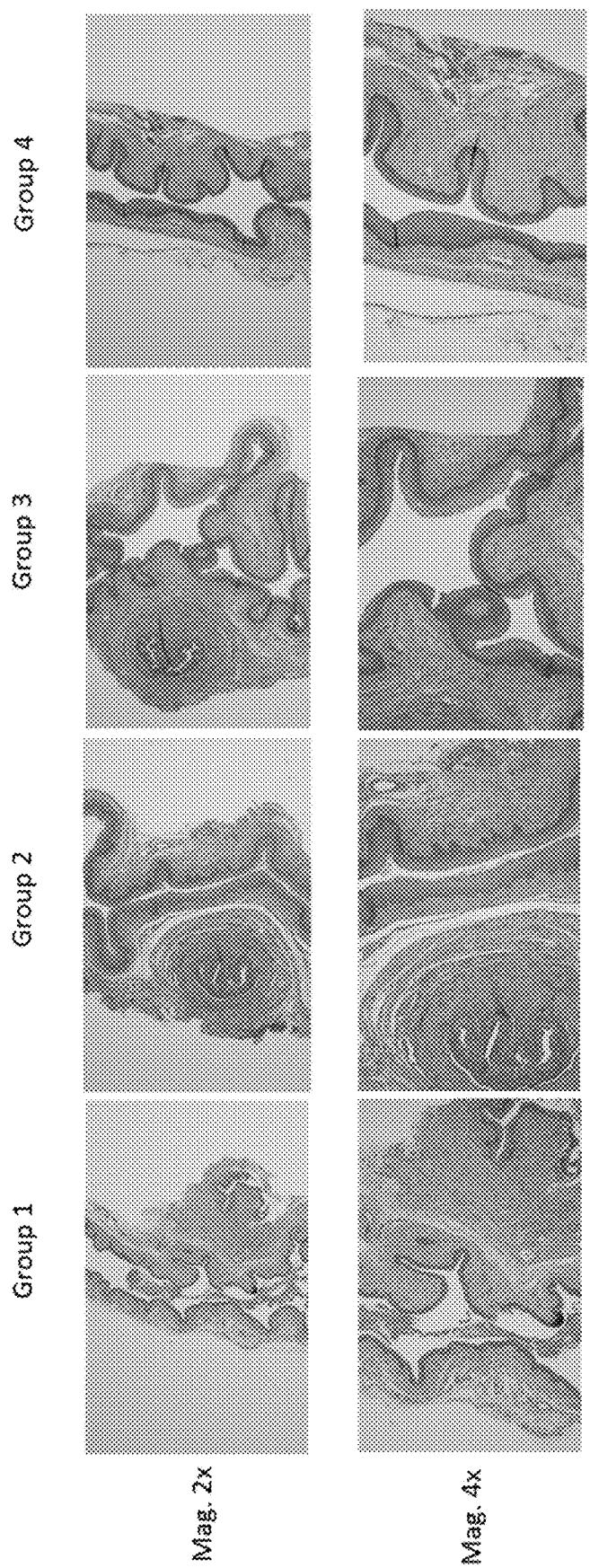
FIG. 8 shows vaginal histologic specimens (stained with hematoxylin and eosin) collected from rats treated with estradiol or estradiol/progesterone after ovariectomy.

Significantly reduced uterine weight was observed in both groups receiving progesterone. See, FIGS. 5 and 6. The histological images of the uterus (FIG. 7) were consistent with the changes in uterine weights, and the overall size of the vaginal histology images (FIG. 8) were also consistent with the treatments. In addition, several estrogen-specific cellular aspects seen in the uterus (e.g., columnar luminal epithelium, eosinophilic endometrium) and vagina (e.g., keratinized epithelium, rete pegs) were not detected in group receiving progesterone subcutaneously ("SC") or transdermally. See, Table 5.

Example 4: Measurement of Hormone Levels in Human Subjects after Application of Transdermal Progesterone/Estradiol Compositions Seven male subjects were administered 1 gram of the cream formulation described in Example 2. Subjects received 25 mg of progesterone and 50 μg of estradiol. Hormone levels were tested in blood serum, saliva, and fingertip capillary blood at 1, 2, and 8 hours after administration. Testing was conducted using known methods. The change in hormone levels over each subject's baseline level, measured prior to cream administration, was determined for each time point.

Figure 9:
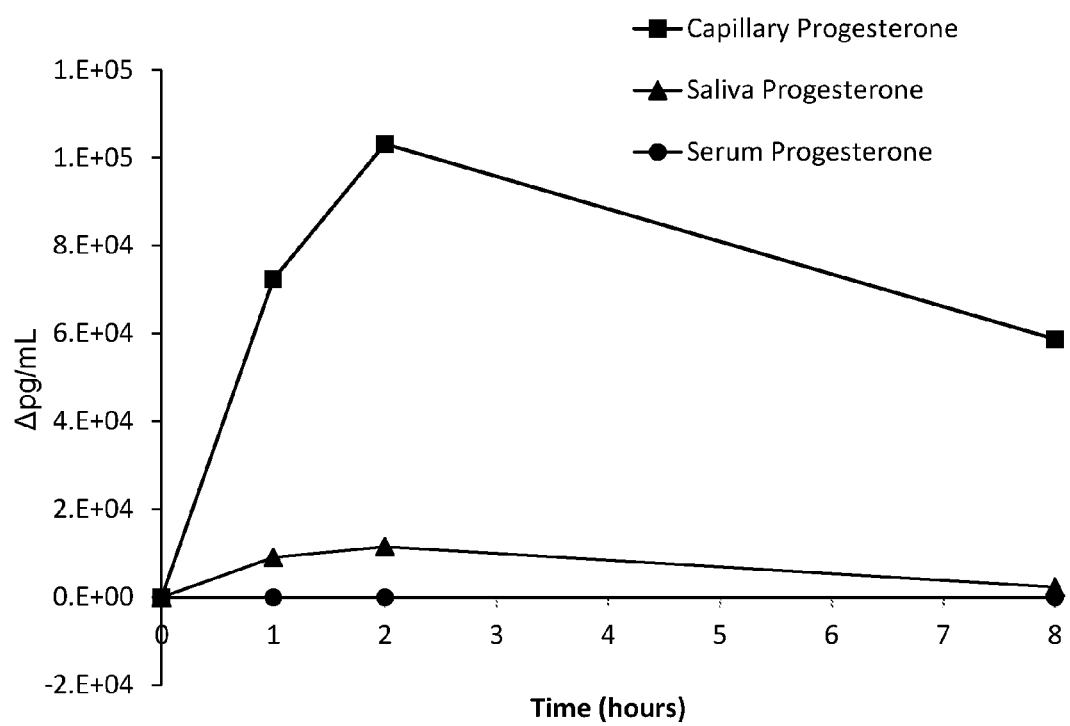
FIG. 9 shows the change in progesterone levels following administration of an exemplary progesterone/estradiol cream in human subjects. Changes over baseline progesterone levels as determined from fingertip capillary blood, saliva, and serum samples are shown.
Figure 10:
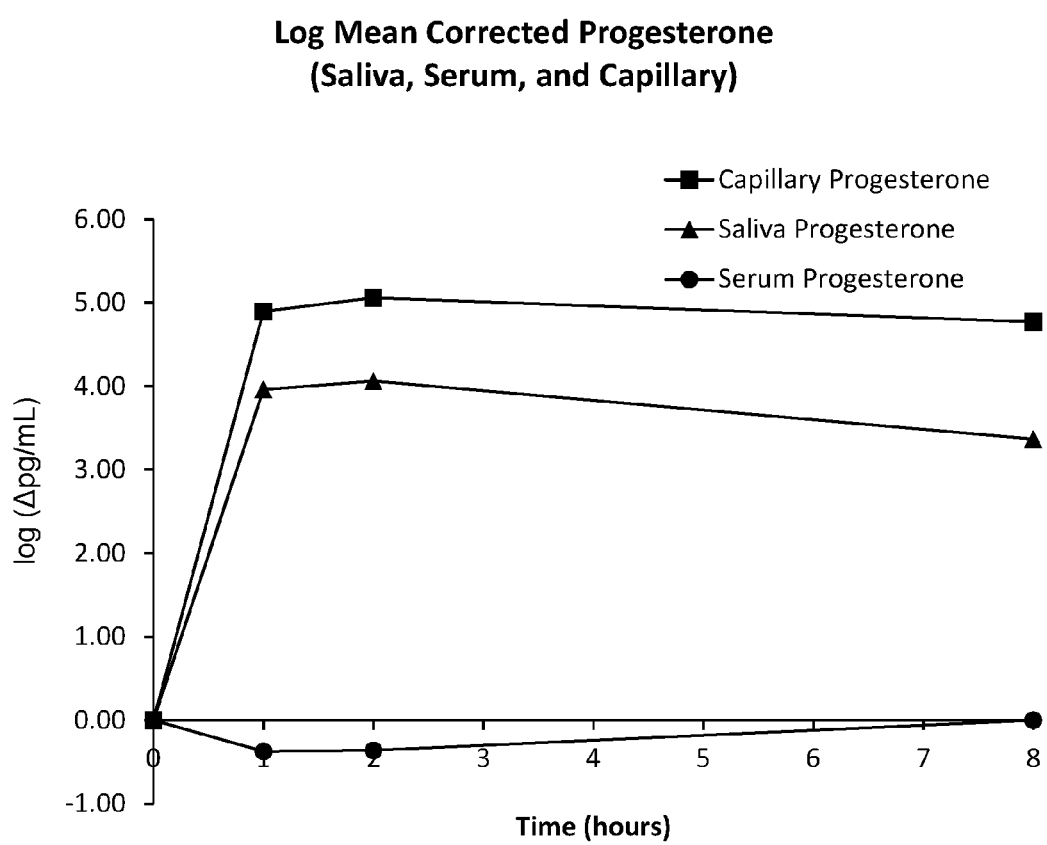
FIG. 10 shows the data of FIG. 9 plotted on a log scale.

Changes in progesterone levels in serum, saliva, and capillary blood are shown in FIGS. 9 and 10, and changes in estradiol levels in serum, saliva, and capillary blood are

TABLE 5

| Endpoint | 0 μg/kg (SC Vehicle)/0 mg/kg (Dermal Prog) LSMean | LSM s.e. | 3 μg/kg (SC EST)/0 mg/kg (Dermal Prog) LSMean | LSM s.e. | 3 μg/kg (SC Est)/10 mg/kg (SC Prog) LSMean | LSM s.e. | 3 μg/kg (SC Est)/3.125 mg/kg (Dermal Prog) LSMean | LSM s.e. |
|---|---|---|---|---|---|---|---|---|
| Endometrial Height (μm) | 236 | 20 | 418[b] | 20 | 436[b] | 31.1 | 407[b] | 13.5 |
| Luminal Epithelial Cell Height (μm) | 13.8 | 0.753 | 47.8[b] | 1.29 | 31.9[b,d] | 1.2 | 34.3[b,d] | 1.69 |
| Endometrial Gland Size (μm²) | 1930 | 343 | 4540[b] | 343 | 4390[b] | 343 | 4150[b] | 343 |
| Endometrial Gland Density (cells/mm²) | 22.0 | 1.65 | 7.09[b] | 0.456 | 10.3[b,d] | 0.572 | 13.3[b,d,f] | 0.694 |
| Number of Mitotic Figures | 57.7 | 6.75 | 921[b] | 98.2 | 595[b,d] | 63.5 | 728[b] | 77.7 |

LSMean—Least squares mean;
LSM s.e.—Least squares mean standard error
[b]Significantly different from 0 μg/kg (SC Vehicle)/0 mg/kg (Dermal Prog); (p < 0.01)
[d]Significantly different from 3 μg/kg (SC EST)/0 mg/kg (Dermal Prog); (p < 0.01)
[f]Significantly different from 3 μg/kg (SC Est)/10 mg/kg (SC Prog); (p < 0.01)

Figure 11:
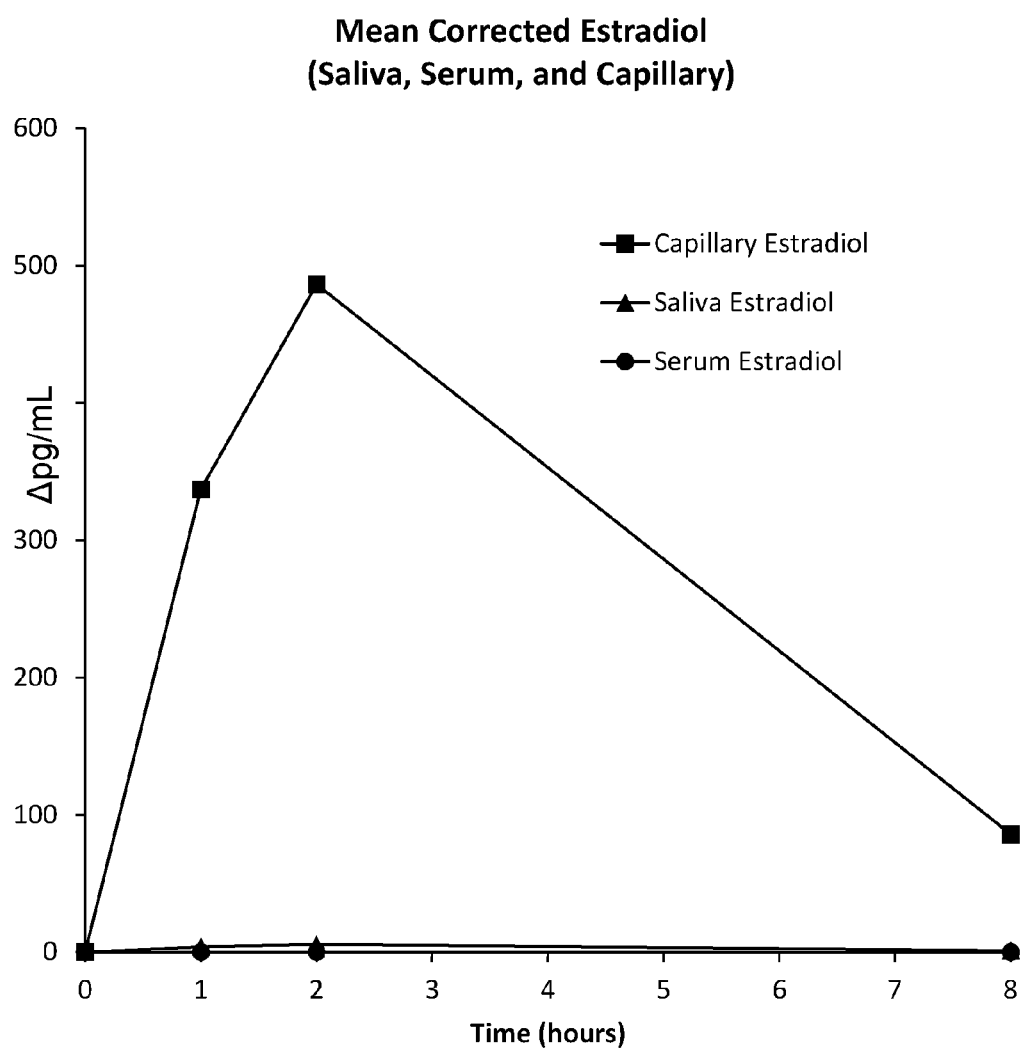
FIG. 11 shows the change in estradiol levels following administration of an exemplary progesterone/estradiol cream in human subjects. Changes over baseline estradiol levels as determined from fingertip capillary blood, saliva, and serum samples are shown.
Figure 12:
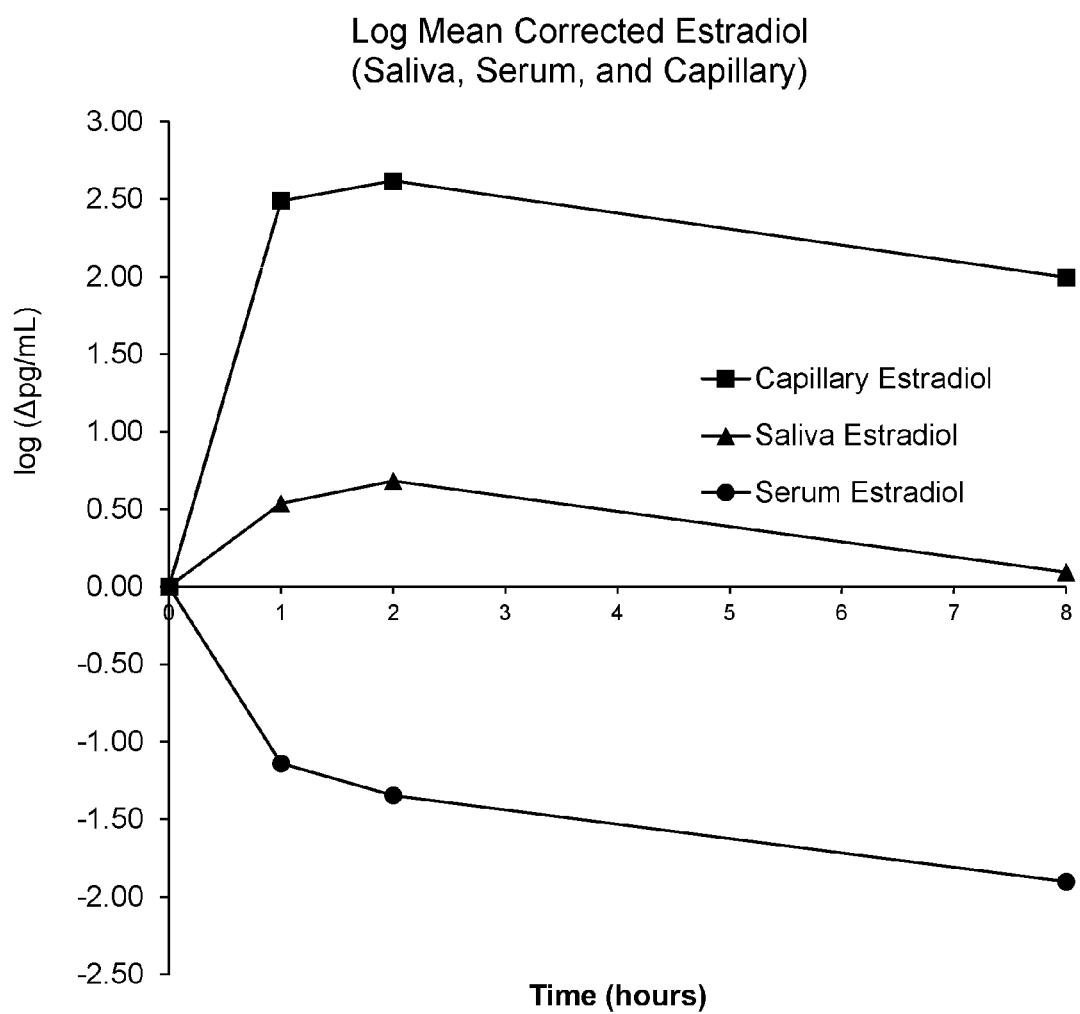
FIG. 12 shows the data of FIG. 11 plotted on a log scale.

Dosing with progesterone, both SC and transdermally, resulted in a significant reduction of luminal epithelial cell height compared to unopposed estradiol. A significant increase in endometrial gland density was observed for both progesterone-dosed groups compared to unopposed estradiol and additionally with transdermal as compared to SC progesterone.

shown in FIGS. 11 and 12. No significant changes in hormone levels were seen in the serum samples following administration. However, large increases in progesterone concentration above baseline were observed for capillary blood and saliva samples as shown in FIGS. 9 and 10. Increases in estradiol concentration above baseline were also observed for capillary blood and saliva samples as shown in FIGS. 11 and 12. The high flux exhibited by the cream formulations and the large increases in hormone levels upon application of the creams indicates that d-limonene is both an excellent solubilizer and penetration enhancer.

Example 5: Measurement of Hormone Levels in Human Subjects after Application of Transdermal Progesterone Composition Further testing was conducted to compare Creams 1 and 2 in Example 1. Saliva samples were obtained at $t_0$ and then 1 g of either cream was administered to the upper arm of each of five subjects. Saliva samples were collected at 2, 4, 6, and 8 hours and analyzed for progesterone content. Results are summarized in Table 6, demonstrating that compositions with and without d-limonene provided delivery of progesterone.

TABLE 6

| Subject | 1 | 2 | 3 | 4 | 5 |
|---|---|---|---|---|---|
| | AUC (ng * hr/mL) | | | | |
| Cream 2 | 116,704 | 11,902 | 5,232 | 212,693 | 898,402 |
| Cream 1 | 61,377 | 14,958 | 2,871 | 50,943 | 166,897 |

Example 6: Progesterone Softgel Formulation

An appropriate volume of a solution not exceeding 200 mg/g progesterone in d-limonene is prepared. The solution is then used as the fill material to produce soft gelatin capsules having 5, 10, 15, 20, 25, 30, 35, 40, 45, 50, 55, 60, 65, 70, 75, 80, 85, 90, 95, 100, 125, 150, 175, 200, 250, or 300 mg of progesterone, as desired.

Example 7: Micelle Formulations Comprising d-Limonene

Pharmaceutical compositions having the ingredients shown in Table 7 were prepared by combining the noted ingredients using standard preparatory techniques.

TABLE 7

| Pharma. Composition/ Component | A | B |
|---|---|---|
| Solubilized Progesterone Formulations (all values presented in mg/g) | | |
| CAPMUL 708G | 723.01 | 723.01 |
| CAPMUL MCM, NF | 80.33 | 80.33 |
| Ultra High Purity d-limonene | 42.28 | 42.28 |
| BHT | 0.28 | 0.28 |
| Progesterone | 60.13 | 60.13 |
| Polysorbate 80 | 70.47 | 46.98 |
| TPGS 1000 | 23.49 | — |
| KOLLIPHOR RH 40 | — | 46.98 |

Example 8: Oral Bioavailability in Rats

Oral bioavailability of the pharmaceutical compositions from Example 7 were assessed in male Sprague-Dawley rats. According to the protocol, 30 male rats were divided into 6 groups of 5 rats each. The rats were then treated with one of the pharmaceutical compositions discussed in Example 7 or PROMETRIUM according to the schedule shown in Table 8.

TABLE 8

| Study Day | Event |
|---|---|
| −4 | Animals were transferred to surgery facility and were group/gang housed. |
| −3 | Animals were observed. |
| −2 | Animals were observed. |
| −1 | Animals were fitted with jugular vein catheters (vaporized isoflurane anesthesia) and treated with analgesics. The animals were fasted for 12 hours starting at 8:00 PM. |
| 0 | Gavage capsules were filled with 20 µL of compound per capsule. Baseline plasma samples were collected, the animals received compound via capsule gavage, and additional plasma samples were taken at 10, 20, 40, 60, 90, 120, 180, and 240 minutes post dosing. Frozen plasma samples were shipped on dry ice for analysis. |

Although PROMETRIUM was dosed in a capsule filled with 20 µL of the PROMETRIUM formulation, the PROMETRIUM capsule contained at least 6 times as much progesterone (400 mg/g formulation) as the test pharmaceutical compositions (60 mg/g composition) due to the way in which PROMETRIUM is formulated.

The means of the PK parameters observed (+/−standard deviation) are shown in Table 9.

TABLE 9

| | A | B | PROMETRIUM |
|---|---|---|---|
| Non-Normalized Progesterone PK Data | | | |
| Dose (mg/kg) | 3.7 | 3.7 | 25 |
| $C_{max}$ (ng/mL) | 13 ± 9 | 24.7 ± 11.2 | 6.9 ± 4.0 |
| $t_{max}$ (hr) | 0.167 ± 0.167 | 0.4 ± 0.346 | 2.2 ± 1.609 |
| $AUC_{0-t}$ (ng · hr/mL) | 12.5 ± 9.2 | 26.2 ± 11.9 | 15.1 ± 8.4 |
| $AUC_{0-\infty}$ (ng · hr/mL) | 14.1 ± 11.1 | 27.1 ± 11.7 | 18.9 ± 13.6 |

All publications and patent documents referenced in this application are incorporated herein by reference in their entirety.

While embodiments have been described and specifically exemplified above, it is not intended that the invention be limited to such embodiments. Various modifications can be made thereto without departing from the scope and spirit of the present invention, as set forth in the following claims.

What is claimed is:

1. A liquid composition comprising about 100 mg progesterone- and d-limonene; wherein the progesterone and d-limonene are present in a weight ratio that does not exceed 1 part progesterone to 4.9 parts d-limonene, further wherein the liquid composition is encapsulated in a soft gelatin capsule suitable for oral administration; and wherein the progesterone is micronized.

2. The liquid composition of claim 1, further comprising an antioxidant.

3. The liquid composition of claim 2, wherein the antioxidant is selected from the group consisting of α-tocopherol acetate, acetone sodium bisulfite, acetyl cysteine, ascorbic acid, ascorbyl palmitate, butylated hydroxyanisole (BHA), butylated hydroxytoluene (BHT), cysteine, cysteine hydrochloride, α-tocopherol, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, tocopherol, and combinations thereof.

4. The liquid composition of claim 1, wherein the composition comprises at least about 80% w/w d-limonene.

5. The liquid composition of claim 4, further comprising an antioxidant.

6. The liquid composition of claim 1 further comprising estradiol.

* * * * *